US012643868B2

(12) United States Patent
Heindl et al.

(10) Patent No.: US 12,643,868 B2
(45) Date of Patent: Jun. 2, 2026

(54) REAGENT FOR MASS SPECTROMETRY

(71) Applicant: Roche Diagnostics Operations, Inc., Indianapolis, IN (US)

(72) Inventors: Dieter Heindl, Munich (DE); Hans-Peter Josel, Weilheim (DE); Uwe Kobold, Weilheim (DE); Christoph Seidel, Weilheim (DE); Martin Rempt, Penzberg (DE); Andreas Leinenbach, Oberhausen (DE); Giuseppe Prencipe, Penzberg (DE); Silvia Baecher, Munich (DE); Simon Ferdinand Loibl, Wolfratshausen (DE); Anna-Skrollan Geiermann, Munich (DE); Jelena Milic, Penzberg (DE); Nicole Pirkl, Penzberg (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 134 days.

(21) Appl. No.: 18/500,149

(22) Filed: Nov. 2, 2023

(65) Prior Publication Data

US 2024/0092742 A1 Mar. 21, 2024

Related U.S. Application Data

(60) Division of application No. 17/155,020, filed on Jan. 21, 2021, now Pat. No. 11,845,733, which is a continuation of application No. PCT/EP2019/069731, filed on Jul. 23, 2019.

(30) Foreign Application Priority Data

Jul. 24, 2018 (EP) .................................... 18185356

(51) Int. Cl.

| | |
|---|---|
| ***C07D 249/06*** | (2006.01) |
| ***C07D 203/04*** | (2006.01) |
| ***C07D 249/04*** | (2006.01) |
| ***C07D 257/04*** | (2006.01) |
| ***C07D 401/04*** | (2006.01) |
| ***C07D 401/14*** | (2006.01) |
| ***C07D 403/04*** | (2006.01) |
| ***C07D 403/06*** | (2006.01) |
| ***C07D 471/04*** | (2006.01) |
| *G01N 30/72* | (2006.01) |

(52) U.S. Cl.

CPC ......... *C07D 249/06* (2013.01); *C07D 203/04* (2013.01); *C07D 249/04* (2013.01); *C07D 257/04* (2013.01); *C07D 401/04* (2013.01); *C07D 401/14* (2013.01); *C07D 403/04* (2013.01); *C07D 403/06* (2013.01); *C07D 471/04* (2013.01); *G01N 30/72* (2013.01)

(58) Field of Classification Search

CPC .. C07D 249/06; C07D 203/04; C07D 249/04; C07D 257/04; C07D 401/04; C07D 401/14; C07D 403/04; C07D 403/06; C07D 471/04; G01N 30/72; G01N 30/7233

See application file for complete search history.

(56) References Cited

U.S. PATENT DOCUMENTS

| | | | | |
|---|---|---|---|---|
| 5,910,419 A * | 6/1999 | Johnson | ............... | G01N 33/946 435/7.1 |
| 9,874,575 B2 * | 1/2018 | Dey | ....................... | G01N 33/58 |
| 2004/0157344 A1 | 8/2004 | Wang et al. | | |

FOREIGN PATENT DOCUMENTS

| | | |
|---|---|---|
| WO | 2004070352 A2 | 8/2004 |
| WO | 2010141075 A1 | 12/2010 |
| WO | 2011059457 A1 | 5/2011 |
| WO | 2011091436 A1 | 7/2011 |
| WO | 2013171567 A1 | 11/2013 |
| WO | 2018141821 A1 | 8/2018 |

OTHER PUBLICATIONS

ISA / EP, International Search Report issued in corresponding Application No. PCT/EP2019/069731, dated Aug. 23, 2019, 4 pp.
ISA / EP. Written Opinion issued in corresponding Application No. PCT/EP2019/069731, dated Aug. 23, 2019, 6 pp.
International Bureau of Wipo, International Preliminary Report on Patentability issued in corresponding Application No. PCT/EP2019/069731, dated Feb. 4, 2021, 8 pp.
Adamczyk et al., O-(Acridinium)hydroxylamine (AHA): a reagent for the preparation of chemiluinescent acridinium pxime (AO)-steroid conjugates; Steroids, 2000, vol. 65, pp. 387-394.
Ban et al., Tyrosine Bioconjugation through Aqueous Ene-Type Reactions: A Click-Like Reaction for Tyrosine; Journal of the American Chemical Society, 2010, vol. 132, pp. 1523-1525.
Francavilla et al., Quaternary ammonium N,N-dichloramines as topical, antimicrobial agents; Bioorganic & Medicinal Chemistry Letters; Vo. 19, 2009, pp. 2731-2734.
Haslop et al., Fully automated radiosynthesis of [1-2-[18F] fluorethyl), 1H[1,2,3]triazole 4-ethylene] triphenylphosphonium bromide as a potential positron emission tomography tracer for imaging apoptosis; Journal of Labelled Compounds and Radiopharmaceuticals, 2013, vol. 56, No. 6, pp. 313-316.
Higashi et al., Chemical derivatization for enhancing sensitivity during LC/ESI-MS/MS quantification of steroids in biological samples: a review, Journal of Steroid Biochemistry & Molecular Biology, 2016, vol. 162, pp. 57-69.
Higashi et al., Isotope-coded ES I-enhancing derivatization reagents for differential analysis, quantification and profiling of metabolites in biological samples by LC/MS: A review, Journal of Pharmaceutical and Biomedical Analysis, 2016, vol. 130, pp. 181-193.

(Continued)

*Primary Examiner* — Shafiqul Haq
(74) *Attorney, Agent, or Firm* — Taft Stettinius & Hollister LLP

(57) ABSTRACT

The present invention relates to reagents which are suitable to be used in mass spectrometry as well as methods of mass spectrometric determination of analyte molecules using said reagents.

9 Claims, 5 Drawing Sheets

(56) References Cited

OTHER PUBLICATIONS

Figure 2:
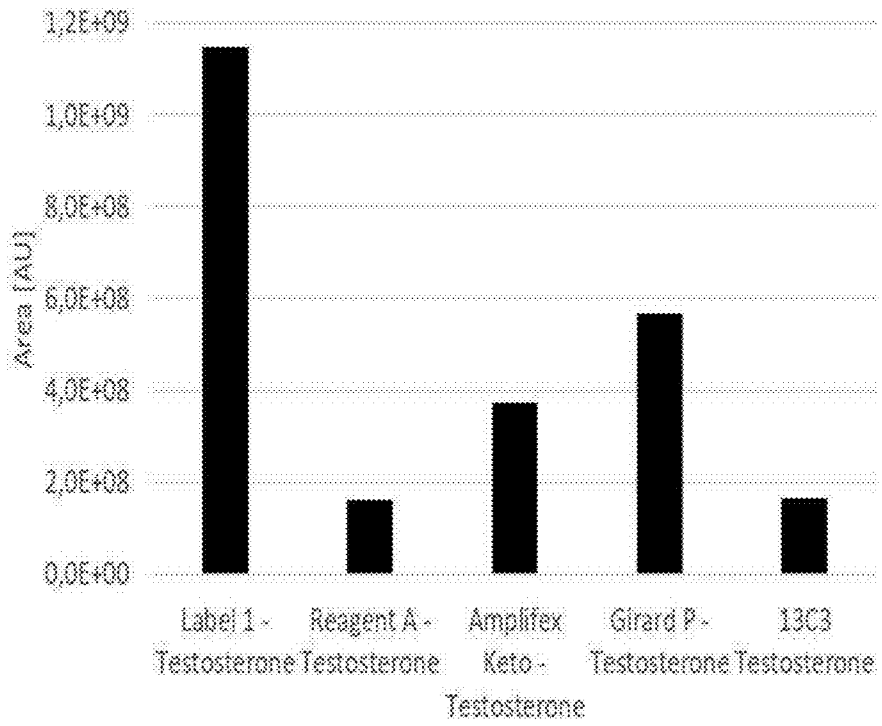

Lattova et al., The Usefulness of Hydrazine Derivatives for Mass Spectrometric Analysis of Carbohydrates; Mass Spectrometry Reviews; 2013, vol. 32, pp. 366-385.
Peters et al., Inhibition of purine biosynthesis by analogues of 4(5)-aminoimidazole-5(4)-carboxamide; Canadian Journal of Physiology and Pharmacology, 1968, vol. 46, No. 2, pp. 195-200.
Ramimoff et al., René et al., 5-Formyl- and 5-Carboxydeoxycytidines Do Not Cause Accumulation of Harmful Repair intermediates in Stem Cells, Journal of the American Chemical Society, 2017, vol. 139, pp. 10359-10364.

* cited by examiner

FIG. 1A - 1C
FIG. 1A
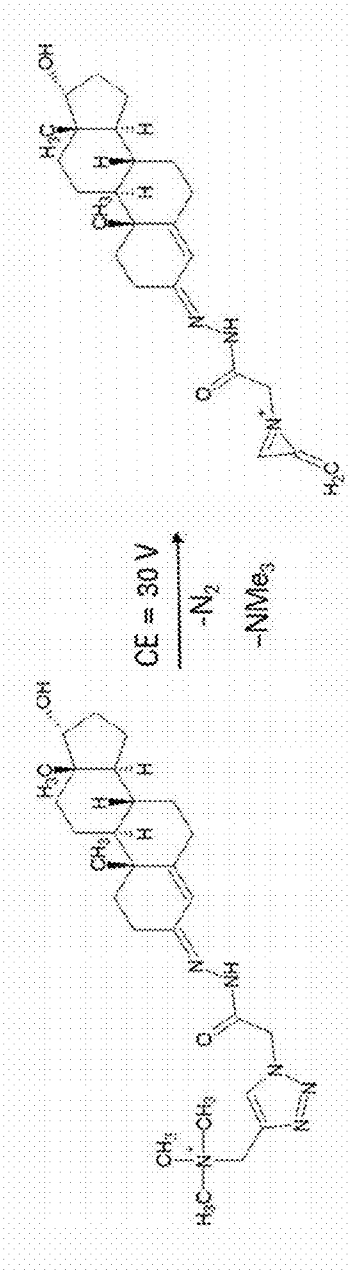
FIG. 1B
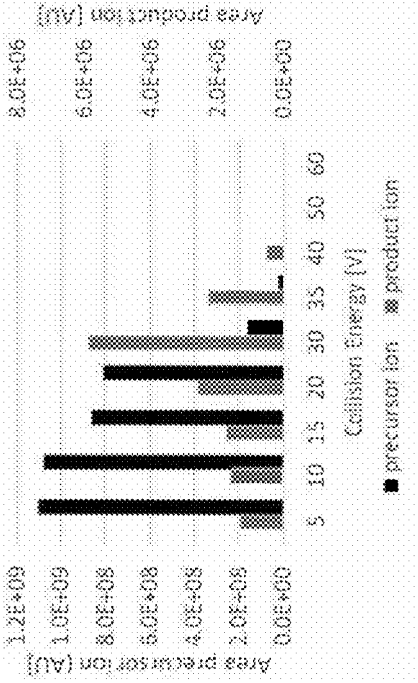
FIG. 1C
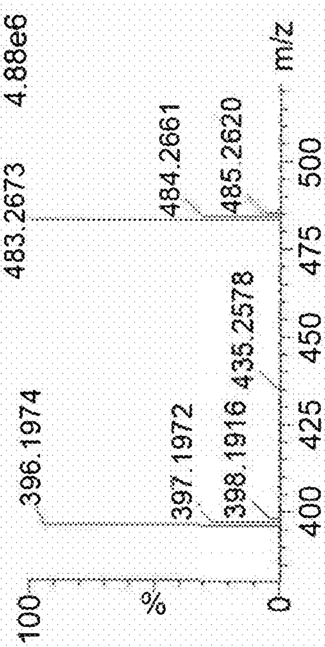

FIGS. 3A - 3B
FIG. 3A
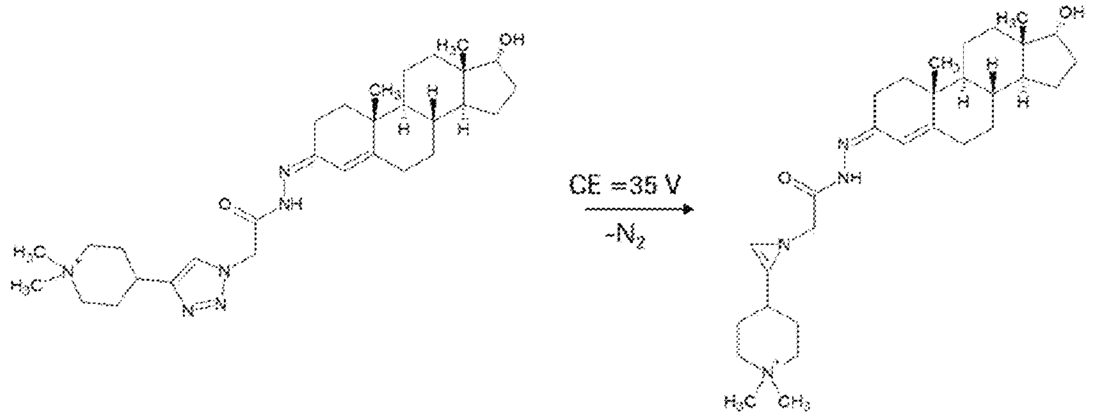
FIG. 3B
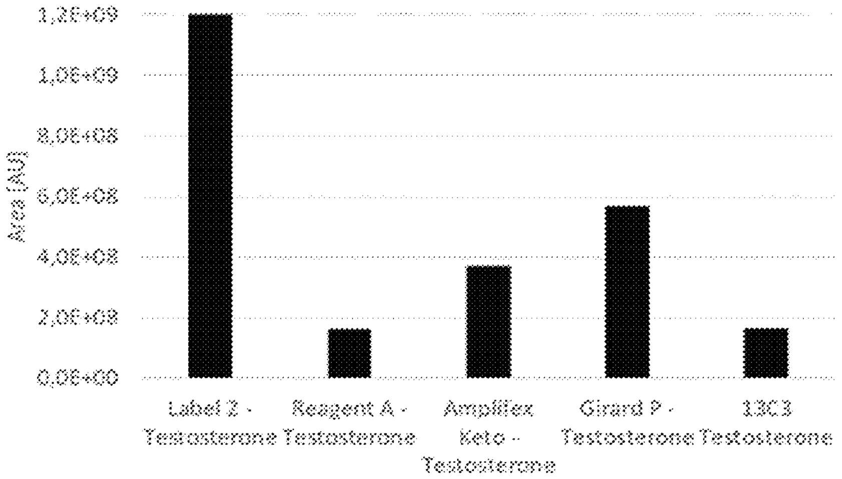

FIGS. 4A - 4B
FIG. 4A
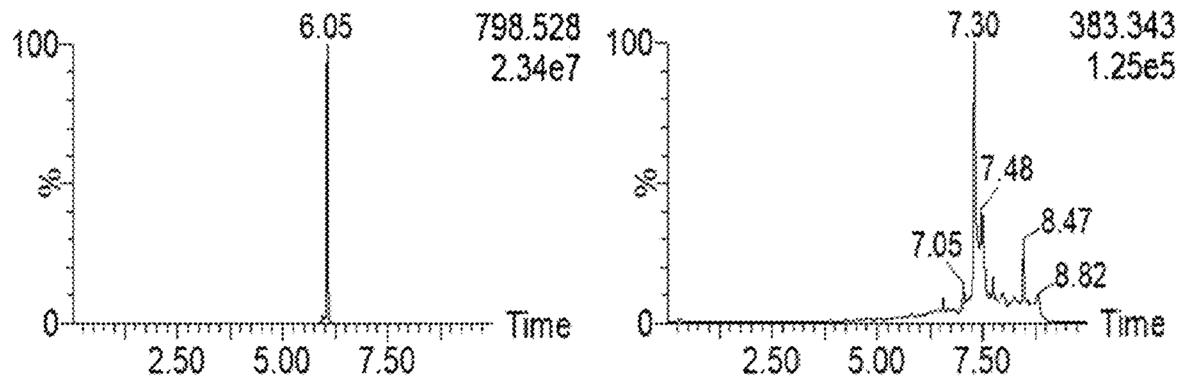
FIG. 4B
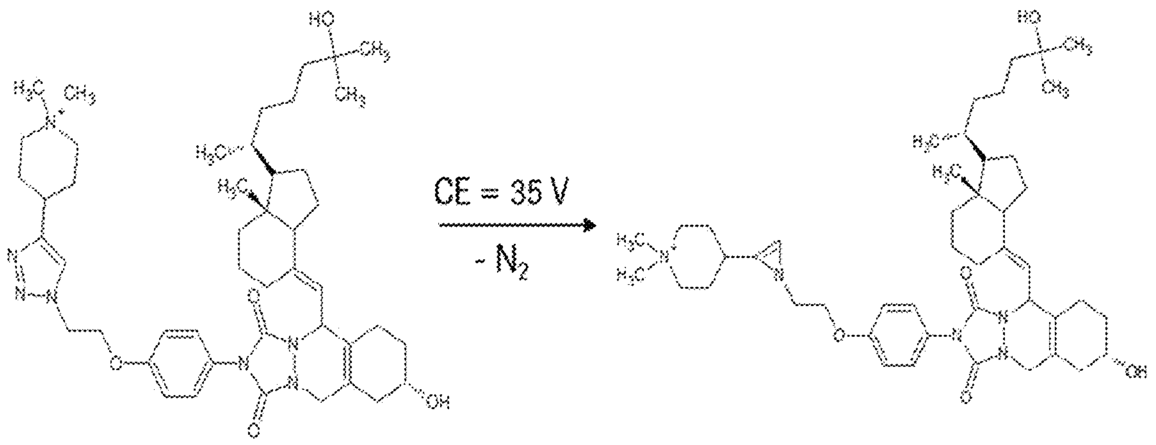

REAGENT FOR MASS SPECTROMETRY

CROSS-REFERENCE TO RELATED APPLICATIONS

This application is a divisional of U.S. patent application Ser. No. 17/155,020, filed Jan. 21, 2021, which is a continuation of International Patent Application No. PCT/EP2019/069731 filed Jul. 23, 2019, and claims priority to European Patent Application No. 18185356.5 filed Jul. 24, 2018, the disclosures of which are hereby incorporated by reference in their entirety.

FIELD OF THE INVENTION

The present invention relates to reagents which are suitable to be used in mass spectrometry as well as methods of mass spectrometric determination of analyte molecules using said reagents.

BACKGROUND OF THE INVENTION

Mass spectrometry (MS) is a widely used technique for the qualitative and quantitative analysis of chemical substances ranging from small molecules to macromolecules. In general, it is a very sensitive and specific method, allowing even for the analysis of complex biological, e.g. environmental or clinical samples. However, for several analytes, especially if analyzed from complex biological matrices such as serum, sensitivity of the measurement remains an issue.

Often MS is combined with chromatographic techniques, particularly gas and liquid chromatography such as e.g. HPLC. Here, the analyzed molecule of interest is separated chromatographically and is individually subjected to mass spectrometric analysis (Higashi et al. (2016) J. of Pharmaceutical and Biomedical Analysis 130 p. 181-190).

There is, however, still a need of increasing the sensitivity of MS analysis methods, particularly for the analysis of analytes that have a low abundance or when only little materials (such as biopsy tissues) are available.

In the art, several derivatization reagents are known which aim to improve the sensitivity of the measurement for these analytes. Amongst others, reagents comprising charged units and neutral loss units which are combined in a single functional unit (e.g. WO 2011/091436). Other reagents comprising separate units are structurally relatively large which effects the general workflow of sample preparation and the MS measurement (Rahimoff et al. (2017) J. Am. Chem. Soc. 139(30), p. 10359-10364). Known derivatization reagents are for example Cookson-type reagents, Amplifex Diene, Amplifex Keto, Girard T, Girard P. All of these bear disadvantages due to often insufficient labelling efficiencies, generation of structural isomers due to coupling chemistry, non-optimal ionization efficiencies, disadvantages for chromatographic separation after coupling, non-optima fragmentation behaviour due to many fragmentation pathways and need for high collision energies.

There is thus an urgent need in the art for a derivatization reagents which allows for a sensitive detection of analytes from complex biological matrices as well as exhibiting a chemical structure which does not negatively influence the MS measurement workflow. This is of particular importance in a random-access, high-throughput MS set up, wherein several different analytes exhibiting different chemical properties have to be measured in a short amount of time.

The present invention relates to a novel reagent which allows for a sensitive determination of analyte molecules such as steroids, proteins, and other types of analytes, in biological samples. The reagent is designed in a modular manner to allow the individual adaption for specific needs arising in the measurement of certain analytes or for specific workflow adaptations. Furthermore, the reagents are designed in manner to be as small as possible to interfere as little as possible with the measurement workflow, in particular to interfere as little as possible with the chromatographic enrichment and separation processes which are performed prior to the actual MS measurement.

SUMMARY OF THE INVENTION

In a first aspect, the present invention relates to compounds of formula A:

X-L1-Y-L2-Z wherein

X is a reactive unit, which is in particular capable of forming a covalent bond with an analyte molecule, L1 and L2 are independently of each other substituted or non-substituted linker, in particular linear linker, Y is a neutral loss unit, Z is a charged unit comprising at least one permanently charged moiety, including any salt thereof.

In a second aspect, the present invention relates to a composition comprising the compound of the first aspect of the present invention.

In a third aspect, the present invention relates to a kit comprising the compound of the first aspect or the composition of the second aspect of the present invention.

In a fourth aspect, the present invention relates to a covalent adduct comprising an analyte molecule and the compound of the first aspect of the present invention, in particular to a covalent adduct formed by chemical reaction of an analyte molecule and the compound of the first aspect of the present invention.

In a fifth aspect, the present invention relates to the use of the compound of the first aspect of the present invention, or the composition of the second aspect of the present invention, or the kit of the third aspect of the present invention for the mass spectrometric determination of an analyte molecule.

In a sixth aspect, the present invention relates to a method for the mass spectrometric determination of an analyte molecule comprising the steps:

(a) reacting the analyte molecule with the compound of the first aspect of the present invention, whereby a covalent adduct of the analyte molecule and the compound of formula A is formed, and (b) subjecting the covalent adduct from step (a) to a mass spectrometric analysis.

LIST OF FIGURES

FIG. 1A-1C: Label 1-Testosterone derivative: (FIG. 1A) MS fragmentation of Label 1-Testosterone derivative: concerted neutral loss of the trimethylamine and $N_2$ from the triazole group (Δ 87 Da); (FIG. 1B) Peak area of parent ion (left axis, black bars) and daughter ion (right axis, grey bars) of Label 1-Testosterone derivative at different collision energies; (FIG. 1C) MS spectrum of Label 1-Testosterone at a collision energy of 30 V. Precursor ion m/z 483.2673, product ion m/z 396.1974.

FIG. 2: Comparison to other Reagents: Peak areas of parent ions at maximal intensities of Label 1-Testosterone, Reagent A-Testosterone, Amplifex Keto-Testosterone, Girard P-Testosterone and free $^{13}C_3$-Testosterone at 0.1 µg/mL.

FIG. 3A & 3B: Label 2-Testosterone derivative: (FIG. 3A) MS fragmentation of Label 2-Testosterone derivative: neutral loss of $N_2$ from the triazole group (Δ 28 Da); (FIG. 3B) Peak areas of parent ions at maximal intensities of Label 2-Testosterone, Reagent A-Testosterone, Amplifex Keto-Testosterone, Girard P-Testosterone and free $^{13}C_3$-Testosterone at 0.1 g/mL.

FIG. 4A & 4B: Label 2-25(011) Vitamin D3 derivative: (FIG. 4A) LC chromatograms of labeled 25-OH-Vitamin D3 (left) and free 25-OH-Vitamin D3 (right), (FIG. 4B) MS fragmentation of labeled 25-OH-Vitamin D3: neutral loss of $N_2$ from the triazole group (Δ 28 Da).

Figure 5:
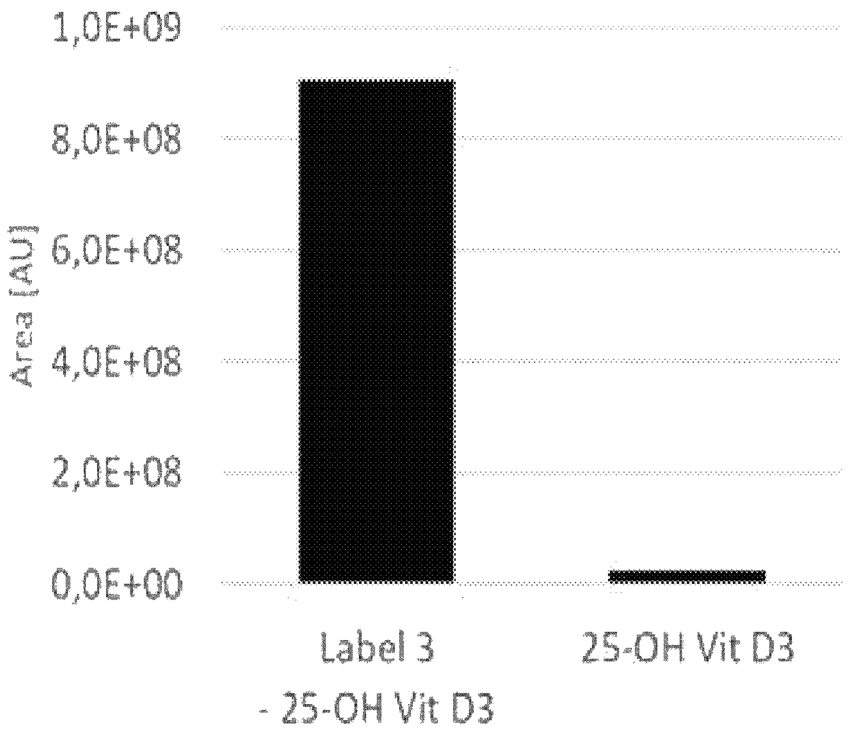

FIG. 5: Comparison to non derivatized 25-(OH)Vitamin D3: Peak areas of parent ions at maximal intensities of labeled 25-OH-Vitamin D3 derivative and free 25-OH-Vitamin D3 at 0.1 g/mL.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The various described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Percentages, concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "4% to 20%" should be interpreted to include not only the explicitly recited values of 4% to 20%, but to also include individual values and sub-ranges within the indicated range. Thus, included in this numerical range are individual values such as 4, 5, 6, 7, 8, 9, 10, . . . 18, 19, 20% and sub-ranges such as from 4-10%, 5-15%, 10-20%, etc. This same principle applies to ranges reciting minimal or maximal values. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

The term "Mass Spectrometry" ("Mass Spec" or "MS") relates to an analytical technology used to identify compounds by their mass. MS is a methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). The term "ionization" or "ionizing" refers to the process of generating an analyte ion having a net electrical charge equal to one or more electron units. Negative ions are those having a net negative charge of one or more electron units, while positive ions are those having a net positive charge of one or more electron units. The MS method may be performed either in "negative ion mode", wherein negative ions are generated and detected, or in "positive ion mode" wherein positive ions are generated and detected.

"Tandem mass spectrometry" or "MS/MS" involves multiple steps of mass spectrometry selection, wherein fragmentation of the analyte occurs in between the stages. In a tandem mass spectrometer, ions are formed in the ion source and separated by mass-to-charge ratio in the first stage of mass spectrometry (MS1). Ions of a particular mass-to-charge ratio (precursor ions or parent ion) are selected and fragment ions (or daughter ions) are created by collision-induced dissociation, ion-molecule reaction, or photodissociation. The resulting ions are then separated and detected in a second stage of mass spectrometry (MS2).

Most sample workflows in MS further include sample preparation and/or enrichment steps, wherein e.g. the analyte(s) of interest are separated from the matrix using e.g.

gas or liquid chromatography. Typically, for the mass spectrometry measurement, the following three steps are performed:

1. a sample comprising an analyte of interest is ionized, usually by adduct formation with cations, often by protonation to cations. Ionization source include but are not limited to electrospray ionization (ESI) and atmospheric pressure chemical ionization (APCI).
2. the ions are sorted and separated according to their mass and charge. High-field asymmetric-waveform ion-mobility spectrometry (FAIMS) may be used as ion filter.
3. the separated ions are then detected, e.g. in multiple reaction mode (MRM), and the results are displayed on a chart.

The term “electrospray ionization” or “ESI,” refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

The term “atmospheric pressure chemical ionization” or “APCI,” refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_1$ gas may be used to improve removal of solvent. The gas-phase ionization in APCI can be more effective than ESI for analyzing less-polar entity.

“Multiple reaction mode” or “MRM” is a detection mode for a MS instrument in which a precursor ion and one or more fragment ions arc selectively detected.

“Tandem mass spectrometry” or “MS/MS” involves multiple steps of mass spectrometry selection, wherein fragmentation of the analyte occurs in between the stages. In a tandem mass spectrometer, ions are formed in the ion source and separated by mass-to-charge ratio in the first stage of mass spectrometry (MS1). Ions of a particular mass-to-charge ratio (precursor ions or parent ion) are selected and fragment ions (or daughter ions) are created by collision-induced dissociation, ion-molecule reaction, or photodissociation. The resulting ions are then separated and detected in a second stage of mass spectrometry (MS2).

Since a mass spectrometer separates and detects ions of slightly different masses, it easily distinguishes different isotopes of a given element. Mass spectrometry is thus, an important method for the accurate mass determination and characterization of analytes, including but not limited to low-molecular weight analytes, peptides, polypeptides or proteins. Its applications include the identification of proteins and their post-translational modifications, the elucidation of protein complexes, their subunits and functional interactions, as well as the global measurement of proteins in proteomics. De novo sequencing of peptides or proteins by mass spectrometry can typically be performed without prior knowledge of the amino acid sequence.

Mass spectrometric determination may be combined with additional analytical methods including chromatographic methods such as gas chromatography (GC), liquid chromatography (LC), particularly HPLC, and/or ion mobility-based separation techniques.

In the context of the present disclosure, the term “analyte”, “analyte molecule”, or “analyte(s) of interest” are used interchangeably referring the chemical specis to be analysed via mass spectrometry. Chemical specis suitable to be analysed via mass spectrometry, i.e. analytes, can be any kind of molecule present in a living organism, include but are not limited to nucleic acid (e.g. DNA, mRNA, miRNA, rRNA etc.), amino acids, peptides, proteins (e.g. cell surface receptor, cytosolic protein etc.), metabolite or hormones (e.g. testosterone, estrogen, estradiol, etc.), fatty acids, lipids, carbohydrates, steroids, ketosteroids, secosteroids (e.g. Vitamin D), molecules characteristic of a certain modification of another molecule (e.g. sugar moieties or phosphoryl residues on proteins, methyl-residues on genomic DNA) or a substance that has been internalized by the organism (e.g. therapeutic drugs, drugs of abuse, toxin, etc.) or a metabolite of such a substance. Such analyte may serve as a biomarker. In the context of present invention, the term “biomarker” refers to a substance within a biological system that is used as an indicator of a biological state of said system.

The term “limit of detection” or “LOD” is the lowest concentration of an analyte that the bioanalytical procedure can reliably differentiate the analyte from background noise.

The term “limit of quantification”, “limit of quantitation” or “LOQ” refers to the lowest amount of an analyte in a sample that can be quantitatively determined with acceptable precision and accuracy, with a relative standard deviation (RSD %) of 20% and an accuracy of 80% to 120%.

Analytes may be present in a sample of interest, e.g. a biological or clinical sample. The term “sample” or “sample of interest” are used interchangeably herein, referring to a part or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as blood, serum, plasma, synovial fluid, spinal fluid, urine, saliva, and lymphatic fluid, or solid samples such as dried blood spots and tissue extracts. Further examples of samples are cell cultures or tissue cultures.

In the context of the present disclosure, the sample may be derived from an “individual” or “subject”. Typically, the subject is a mammal. Mammals include, but are not limited to, domesticated animals (e.g., cows, sheep, cats, dogs, and horses), primates (e.g., humans and non-human primates such as monkeys), rabbits, and rodents (e.g., mice and rats).

Before being analysed via Mass Spectrometry, a sample may be pre-treated in a sample- and/or analyte specific manner. In the context of the present disclosure, the term “pre-treatment” refers to any measures required to allow for the subsequent analysis of a desired analyte via Mass Spectrometry. Pre-treatment measures typically include but are not limited to the elution of solid samples (e.g. elution of dried blood spots), addition of hemolizing reagent (HR) to whole blood samples, and the addition of enzymatic reagents to urine samples. Also the addition of internal standards (ISTD) is considered as pre-treatment of the sample.

The term “hemolysis reagent (HR) refers to reagents which lyse cells present in a sample, in the context of this invention hemolysis reagents in particular refer to reagents which lyse the cell present in a blood sample including but not limited to the erythrocytes present in whole blood samples. A well known hemolysis reagent is water ($H_2O$). Further examples of hemolysis reagents include but are not limited to deionized water, liquids with high osmolarity (e.g. 8M urea), ionic liquids, and different detergents.

Typically, an internal standard (ISTD) is a known amount of a substance which exhibits similar properties as the analyte of interest when subjected to the mass spectrometric detection workflow (i.e. including any pre-treatment, enrichment and actual detection step). Although the ISTD exhibits similar properties as the analyte of interest, it is still clearly distinguishable from the analyte of interest. Exemplified, during chromatographic separation, such as gas or liquid chromatography, the ISTD has about the same retention time as the analyte of interest from the sample. Thus, both the analyte and the ISTD enter the mass spectrometer at the same time. The ISTD however, exhibits a different molecular mass than the analyte of interest from the sample. This allows a mass spectrometric distinction between ions from the ISTD and ions from the analyte by means of their different mass/charge (m/z) ratios. Both are subject to fragmentation and provide daughter ions. These daughter ions can be distinguished by means of their m/z ratios from each other and from the respective parent ions. Consequently, a separate determination and quantification of the signals from the ISTD and the analyte can be performed. Since the ISTD has been added in known amounts, the signal intensity of the analyte from the sample can be attributed to a specific quantitative amount of the analyte. Thus, the addition of an ISTD allows for a relative comparison of the amount of analyte detected, and enables unambiguous identification and quantification of the analyte(s) of interest present in the sample when the analyte(s) reach the mass spectrometer. Typically, but not necessarily, the ISTD is an isotopically labeled variant (comprising e.g. $^{2}H$, $^{13}C$, or $^{15}N$ etc. label) of the analyte of interest.

In addition to the pre-treatment, the sample may also be subjected to one or more enrichment steps. In the context of the present disclosure, the term "first enrichment process" or "first enrichment workflow" refers to an enrichment process which occurs subsequent to the pre-treatment of the sample and provides a sample comprising an enriched analyte relative to the initial sample. The first enrichment workflow may comprise chemical precipitation (e.g. using acetonitrile) or the use of a solid phase. Suitable solid phases include but are not limited to Solid Phase Extraction (SPE) cartridges, and beads. Beads may be non-magnetic, magnetic, or paramagnetic. Beads may be coated differently to be specific for the analyte of interest. The coating may differ depending on the use intended, i.e. on the intended capture molecule. It is well-known to the skilled person which coating is suitable for which analyte. The beads may be made of various different materials. The beads may have various sizes and comprise a surface with or without pores.

In the context of the present disclosure the term "second enrichment process" or "second enrichment workflow" refers to an enrichment process which occurs subsequent to the pre-treatment and the first enrichment process of the sample and provides a sample comprising an enriched analyte relative to the initial sample and the sample after the first enrichment process.

The term "chromatography" refers to a process in which a chemical mixture carried by a liquid or gas is separated into components as a result of differential distribution of the chemical entities as they flow around or over a stationary liquid or solid phase.

The term "liquid chromatographie" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Methods in which the stationary phase is more polar than the mobile phase (e.g., toluene as the mobile phase, silica as the stationary phase) are termed normal phase liquid chromatography (NPLC) and methods in which the stationary phase is less polar than the mobile phase (e.g., water-methanol mixture as the mobile phase and C18 (octadecylsilyl) as the stationary phase) is termed reversed phase liquid chromatography. (RPLC).

"High performance liquid chromatography" or "HPLC" refers to a method of liquid chromatography in which the degree of separation is increased by forcing the mobile phase under pressure through a stationary phase, typically a densely packed column. Typically, the column is packed with a stationary phase composed of irregularly or spherically shaped particles, a porous monolithic layer, or a porous membrane. HPLC is historically divided into two different sub-classes based on the polarity of the mobile and stationary phases. Methods in which the stationary phase is more polar than the mobile phase (e.g., toluene as the mobile phase, silica as the stationary phase) are termed normal phase liquid chromatography (NPLC) and the opposite (e.g., water-methanol mixture as the mobile phase and C18 (octadecylsilyl) as the stationary phase) is termed reversed phase liquid chromatography (RPLC). Micro LC refers to a HPLC method using a column having a norrow inner column diameter, typically below 1 mm, e.g. about 0.5 mm. "Ultra high performance liquid chromatography" or "UHPLC" refers to a HPLC method using a pressure of 120 MPa (17,405 lbf/in2), or about 1200 atmospheres. Rapid LC refers to an LC method using a column having an inner diameter as mentioned above, with a short length<2 cm, e.g. 1 cm, applying a flow rate as mentioned above and with a pressure as mentioned above (Micro LC, UHPLC). The short Rapid LC protocol includes a trapping/wash/elution step using a single analytical column and realizes LC in a very short time<1 min.

Further well-known LC modi include Hydrophilic interaction chromatography (HILIC), size-exclusion LC, ion exchange LC, and affinity LC.

LC separation may be single-channel LC or multi-channel LC comprising a plurality of LC channels arranged in parallel. In LC analytes may be separated according to their polarity or log P value, size or affinity, as generally known to the skilled person.

In the context of the present invention, the term "compound" refers to a chemical substance having a specific chemical structure. Said compound may comprise one or more functional units. Each unit may fulfil a different functionality, or two or more functional units may fulfil the same function. Functional units include but are not limited to reactive units, charged units, and neutral loss units.

The term "neutral loss unit" refers to a unit, which is able to loose a entity having no charge, i.e. which is able to release a neutral entity. Typical, the neutral entity comprises a single atom or a plurality of atoms. A neutral loss unit may be neutral, positively, or negatively charged. A neutral loss unit is, under conditions of MS, e.g. when subjected to collision-induced dissociation (CID), for example in triple quadrupole MS, capable of fragmentation, whereby at least one neutral entity is released. After release of the neutral entity, the remainder of the neutral loss unit remains its original charge. Accordingly, in case the neutral loss unit is not charged it remains neutral after the loss of the neutral entity. In case the neutral loss unit is positively charged it remains positive after the loss of the neutral entity. In case the neutral loss unit is negatively charged it remains negative after the loss of the neutral entity. Typically, but not necessarily, one neutral entity is released. However, also more than one neutral entity may be released. This may occurs in a single fragmentation event (i.e. two or more neutral entities entity are released simultaneously) or in two or more subsequent fragmentation events (one neutral entity is released first and the one or more further neutral entities are released subsequentially).

The term "fragmentation" refers to the dissociation of a single molecule into two or more separate molecules. As used herein, the term fragmentation refers to a specific fragmentation event, wherein the breaking point in the parent molecule at which the fragmentation event takes place is well defined, and wherein the two or more daughter molecules resulting from the fragmentation event are well characterised. It is well-known to the skilled person how to determine the breaking point of a parent molecule as well as the two or more resulting daughter molecules. The resulting daughter molecules may be stable or may dissociate in subsequent fragmentation events. Exemplified, in case a parent molecule undergoing fragmentation comprises a triazol or tetrazol unit, the skilled person is able to determine based on the overall structure of the molecule where the triazol or tetrazol unit will fragment to release an N2 entity, i.e the resulting daughter molecules would be an N2 molecule and a parent molecule lacking N2 (still comprising the remainder of the triazol or tetrazol unit). Fragmentation may occur via collision-induced dissociation (CID), electron-capture dissociation (ECD), electron-transfer dissociation (ETD), negative electron-transfer dissociation (NETD), electron-detachment dissociation (EDD), photodissociation, particularly infrared multiphoton dissociation (IRMPD) and blackbody infrared radiative dissociation (BIRD), surface-induced dissociation (SID), Higher-energy C-trap dissociation (HCD), charge remote fragmentation.

The term "reactive unit" refers to a unit able to react with another molecule, i.e. which is able to form covalent bond with another molecule, such as an analyte of interest. Typically, such covalent bond is formed with a chemical group present in the other molecule. Accordingly, upon chemical reaction, the reactive unit of the compound forms a covalent bond with a suitable chemical group present in the analyte molecule. As this chemical group present in the analyte molecule, fulfils the function of reacting with the reactive unit of the compound, the chemical group present in the analyte molecule is also referred to as the "functional group" of the analyte. The formation of the covalent bond occurs in each case in a chemical reaction, wherein the new covalent bond is formed between atoms of the reactive group and the functional groups of the analyte. It is well known to the person skilled in the art that in forming the covalent bond between the reactive group and the functional groups of the analyte, atoms are lost during this chemical reaction.

The term "charged unit" refers to a unit of a compound which comprises a charged moiety. The charge may be permanent or may alter depending on the surrounding conditions. Typically, the charge is positive or negative. In case the charged unit comprises at least one permanently charged moiety, it is considered that the charge does not alter based on the surrounding conditions, e.g. the change of the pH value does not lead to a change in the charge of the permanently charged unit.

The different functional units of a compound may be connected via linker. The term linker refers to branched or unbranched chemical structures, typically comprising substituted or unsubstituted alkyl units, and may optionally also include one or more heteroatoms. A linker connects different functional units within a compound. Typically, an unbranched linker connect two functional units in one compound, i.e. an unbranched liker may also be referred to as a bi-functional linker or as a linear linker. A branched linker may connect three, four, five, or more functional units, depending on how may branches said linker comprises.

In the context of the present disclosure, the term "adduct" refers to the product produced by the reaction of a compound with an analyte molecule. This reaction leads to the formation of a covalent bond between the compound and the analyte. Accordingly, the term adduct refers to the covalently bound reaction product formed by the reaction of the compound with the analyte molecule.

A "kit" is any manufacture (e.g. a package or container) comprising at least one reagent, e.g., a medicament for treatment of a disorder, or a probe for specifically detecting a biomarker gene or protein of the invention. The kit is preferably promoted, distributed, or sold as a unit for performing the methods of the present invention. Typically, a kit may further comprise carrier means being compartmentalized to receive in close confinement one or more container means such as vials, tubes, and the like In particular, each of the container means comprises one of the separate elements to be used in the method of the first aspect. Kits may further comprise one or more other containers comprising further materials including but not limited to buffers, diluents, filters, needles, syringes, and package inserts with instructions for use. A label may be present on the container to indicate that the composition is used for a specific application, and may also indicate directions for either in vivo or in vitro use. The computer program code may be provided on a data storage medium or device such as a optical storage medium (e.g., a Compact Disc) or directly on a computer or data processing device. Moreover, the kit may, comprise standard amounts for the biomarkers as described elsewhere herein for calibration purposes.

A "package insert" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments, etc.

Embodiments

In a first aspect, the present invention relates to compounds of formula A:

X-L1-Y-L2-Z wherein

X is a reactive unit, which is in particular capable of forming a covalent bond with an analyte molecule L1 and L2 are independently of each other substituted or non-substituted linker, in particular linear linker, Y is a neutral loss unit, Z is a charged unit comprising at least one permanently charged moiety, in particular comprising one permanently charged moiety, including any salt thereof.

In embodiments of the first aspect of the present invention, the compound of formula A according to the present invention comprises a reactive unit X which is capable of reacting with an analyte molecule. The reactive unit X is capable of reacting with an analyte molecule such that a covalent bond between the compound of formula A and the analyte molecule is formed. In embodiments of the first aspect of the present invention, the reactive unit X forms a covalent bond with the compound of formula A. In particular, the covalent bond is formed between the reactive unit X of compound of formula A and a functional group present in the analyte molecule.

Depending on the functional groups present in the analyte molecule to be determined, the skilled person will select an appropriate reactive unit X for compound of formula A. It is within common knowledge to decide which reactive unit X will qualify for binding to a functional group of an analyte of interest.

In embodiments of the first aspect of the present invention, the analyte molecule comprises a functional group selected from the group consisting of carbonyl group, diene group, hydroxyl group, amine group, imine group, thiol group, diol group, phenolic group, expoxid group, disulfide group, and azide group, each of which is capable of forming a covalent bond with reactive unit X of compound of formula A. Further, it is also contemplated within the scope of the present invention that a functional group present on an analyte molecule would be first converted into another group that is more readily available for reaction with reactive unit X of compounds of formula A.

In embodiments of the first aspect of the present invention, the analyte molecule is selected from the group consisting of steroids, ketosteroids, secosteroids, amino acids, peptides, proteins, carbohydrates, fatty acids, lipids, nucleosides, nucleotides, nucleic acids and other biomolecules including small molecule metabolites and cofactors as well as therapeutic drugs, drugs of abuse, toxins or metabolites thereof.

In embodiments of the first aspect of the present invention, the analyte molecule comprises a carbonyl group as functional group which is selected from the group consisting of a carboxylic acid group, aldehyde group, keto group, a masked aldehyde, masked keto group, ester group, amide group, and anhydride group.

In embodiments of the first aspect of the present invention, wherein the carbonyl group is an amide group, the skilled person is well-aware that the amide group as such is a stable group, but that it can be hydrolized to convert the amide group into an carboxylic acid group and an amino group. Hydrolysis of the amide group may be achieved via acid/base catalysed reaction or by enzymatic process either of which is well-known to the skilled person. In embodiments of the first aspect of the present invention, wherein the carbonyl group is a masked aldehyde group or a masked keto group, the respective group is either a hemiacetal group or acetal group, in particular a cyclic hemiacetal group or acetal group. In embodiments of the first aspect of the present invention, the acetal group, is converted into an aldehyde or keto group before reaction with the compound of formula A.

In embodiments of the first aspect of the present invention, the carbonyl group is a keto group. In embodiments of the first aspect of the present invention, the keto group may be transferred into an intermediate imine group before reacting with the reactive unit of compounds of formula A. In embodiments of the first aspect of the present invention, the analyte molecule comprising one or more keto groups is a ketosteroid. In particular embodiments of the first aspect of the present invention, the ketosteroid is selected from the group consisting of testosterone, epitestosterone, dihydrotestosterone (DHT), desoxymethyltestosterone (DMT), tetrahydrogestrinone (THG), aldosterone, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17-OH pregnenolone, 17-OH progesterone, 17-OH progesterone, androsterone, epiandrosterone, and delta 4 androstenedione) 11-desoxycortisol corticosterone, 21-deoxycortisol, 11-deoxycorticosterone, allopregnanolone, and aldosterone.

In embodiments of the first aspect of the present invention, the carbonyl group is a carboxyl group. In embodiments of the first aspect of the present invention, the carboxyl group reacts directly with the compound of formula A or it is converted into an activated ester group before reaction with the compound of formula A. In embodiments of the first aspect of the present invention, the analyte molecule comprising one or more carboxyl groups is selected from the group consisting of Δ8-Tetrahydrocannabinol-acid, Benzoylecgonin, Salicylic acid, 2-hydroxybenzoic acid, Gabapentin, Pregabalin, Valproic acid, Vancomycin, Methotrexat, Mycophenolic acid, Montelukast, Repaglinide, Furosemide, Telmisartan, Gemfibrozil, Diclorofenac, Ibuprofen, Indomethacin, Zomepirac, Isoxepac, and Penicilin. In embodiments of the first aspect of the present invention, the analyte molecule comprising one or more carboxyl groups is an amino acid selected from the group consisting of arginine, lysine, aspartic acid, glutamic acid, glutamine, asparagine, histidine, serine, threonine, tyrosine, cysteine, tryptophan, alanine, isoleucine, leucine, methionine, phenyalanine, valine, proline, and glycine.

In embodiments of the first aspect of the present invention, the carbonyl group is an aldehyde group. In embodiments of the first aspect of the present invention, the aldehyde group may be transferred into an intermediate imine group before reacting with the reactive unit of compounds of formula A. In embodiments of the first aspect of the present invention, the analyte molecule comprising one or more aldehyde groups is selected from the group consisting of Pyridoxal, N-Acetyl-D-glucosamine, Alcaftadine, Streptomycin, Josamycin.

In embodiments of the first aspect of the present invention, the carbonyl group is an carbonyl ester group. In embodiments of the first aspect of the present invention, the analyte molecule comprising one or more ester groups is selected from the group consisting of Cocaine, Heroin, Ritalin, Aceclofenac, Acetycholine, Amcinonide, Amiloxate, amylocaine, Anileridine, Aranidipine, and Artesunate, Pethidine.

In embodiments of the first aspect of the present invention, the carbonyl group is an anhydride group. In embodiments of the first aspect of the present invention, the analyte molecule comprising one or more anhydride groups is selected from the group consisting of Cantharidin, Succinic Anhydride, Trimellitic Anhydride, and Maleic Anhydride.

In embodiments of the first aspect of the present invention, the analyte molecule comprises one or more diene groups, in particular to conjugated diene groups, as functional group. In embodiments of the first aspect of the present invention, the analyte molecule comprising one or more diene groups is a secosteroid. In embodiments, the secosteroid is selected from the group consisting of Cholecalciferol (Vitamin D3), Ergocalciferol (Vitamin D2), Calcidiol, Calcitriol, Tachysterol, Lumisterol und Tacalcitol. In particular, the secosteroid is Vitamin D, in particular Vitamin D2 or D3 or derivates thereof. In particular embodiments, the secosteroid is selected from the group consisting of Vitamin D2, Vitamin D3, 25-Hydroxy Vitamin D2, 25-Hydroxy Vitamin D3, 3-Epi-25-Hydroxy Vitamin D2, 3-Epi-25-Hydroxy Vitamin D3, 1,25-Dihydroxy Vitamin D2, 1,25-Dihydroxy Vitamin D3, 24,25-Dihydroxy Vitamin D2, and 24,25-Dihydroxy Vitamin D3, Vitamin A, Tretinoin, Isotretinoin, Alitretinoin, Natamycin, Sirolimus, Amphotericin B, Nystatin, Everolimus, Temsirolimus, Fidaxomicin.

In embodiments of the first aspect of the present invention, the analyte molecule comprises one or more hydroxyl group as functional group. In embodiments of the first aspect of the present invention, the analyte molecule comprises a single hydroxyl group or two hydroxyl groups. In embodiments wherein more than one hydroxyl group is present, the two hydroxyl groups may be positioned adjacent to each other (1,2 diol) or may be separated by 1, 2, or 3 C-atoms (1,3-diol, 1,4-diol, 1,5-diol, respectively). In particular embodiments of the first aspect, the analyte molecule comprises an 1,2 diol group. In embodiments, wherein only one hydroxyl group is present, said analyte is selected from the group consisting of primary alcohol, secondary alcohol and tertiary alcohol. In embodiments of the first aspect of the present invention, wherein the analyte molecule comprises one or more hydroxyl groups, the analyte is selected from the group consisting of Benzyl alcohol, Menthol, L-Carnitine, Pyridoxine, Metronidazole, Isosorbide mononitrate, Guaifenesin, Clavulanate, Migitol, Zalcitabine, Isoprenaline, Aciclovir, Methocarbamol, Tramadol, Venlafaxine, Atropine, Clofedanol, alpha-Hydroxyalprazolam, Alpha-Hydroxytriazolam, Lorazepam, Oxazepam, Tamazepam, Ethylglucuronide, Ethylmorphine, Morphine, Morphine-3-glucuronide, Buprenorphine, Codeine, Dihydrocodeine, p-Hydroxypropoxyphene, O-desmethyltramadol, Dihydroquinidine, Quinidine. In embodiments of the first aspect of the present invention, wherein the analyte molecule comprises more than one hydroxyl groups, the analyte is selected from the group consisting of Vitamin C, Glucosamine, Mannitol, Tetrahydrobiopterin, Cytarabine, Azacitidine, Ribavirin, Floxuridine, Gemcitadine, Streptozocin, Adenosine, Vibarabine, Cladribine, Estriol, Trifluridine, Clofarabine, Nadolol, Zanamivir, Lactulose, Adenosine monophosphate, Idoxuridine, Regadenoson, Lincomycin, Clindanycin, Canaglifozin, Tobramycin, Netilmicin, Kanamycin, Ticagrelor, Epirubicin, Doxorubicin, Arbekacin, Steptomycin, Quabain, Amikacin, Neomycin, Framycetin, Paromomycin, Erythromycin, Clarithromycin, Azithromycin, Vindesine, Digitoxin, Digoxin, Metrizamide, Acetyldigitoxin, Deslanoside, Fludaradine, Clofarabine, Gemcitabine, Cytarabine, Capecitabine, Vidarabine, Trifluridine, Idoxuridine, and Plicamycin.

In embodiments of the first aspect of the present invention, the analyte molecule comprises one or more thiol group (including but not limited to alkyl-thiol and thiol-ary groups) as functional group. In embodiments of the first aspect of the present invention, the analyte molecule comprising one or more thiol groups is selected from the group consisting of Thiomandelic acid, DL-Captopril, DL-Thiorphan, N-Acetylcysteine, D-Penicillamine, Glutathione, L-Cysteine, Zefenoprilat, Tiopronin, Dimercaprol, Succimer.

In embodiments of the first aspect of the present invention, the analyte molecule comprises one or more disulfide group as functional group. In embodiments of the first aspect of the present invention, the analyte molecule comprising one or more disulfide groups is selected from the group consisting of Glutathione Disulfide, Dipyrithione, Selenium Sulfide, Disulfiram, Lipoic Acid, L-Cystine, Fursultiamine, Octreotide, Desmopressin, Vapreotide, Terlipressin, Linaclotide, Peginesatide.

In embodiments of the first aspect of the present invention, the analyte molecule comprises one or more epoxide group as functional group. In embodiments of the first aspect of the present invention, the analyte molecule comprising one or more epoxide groups is selected from the group consisting of Carbamazepine 10,11 epoxide, Carfilzomib, Furosemide epoxide, and Fosfomycin, Sevelamer, Cerulenin, Scopolamine, Tiotropium, Methylscopolamine bromide, Eplerenone, Mupirocin, Natamycin, Carfilzomib, Troleandomycin.

In embodiments of the first aspect of the present invention, the analyte molecule comprises one or more phenol groups as functional group. In particular embodiments of the first aspect of the present invention, analyte molecules comprising one or more phenol groups are steroids or steroid-like compounds. In embodiments of the first aspect of the present invention, the analyte molecule comprising one or more phenol groups is a steroid or a steroid-like compound having an A-ring which is $sp^2$ hybridized and an OH group at the 3-position of the A-ring. In particular embodiments of the first aspect of the present invention, the steroid or steroid-like analyte molecule is selected from the group consisting of estrogen, estrogen-like compounds, estrone (E1), estradiol (E2), 17a-estradiol, 17p-estradiol, estriol (E3), 16-epiestriol, 17-epiestriol, and 16, 17-epiestriol, and/or metabolites thereof. In embodiments, the metabolites is selected from the group consisting of estriol, 16-epiestriol (16-epiE3), 17-epiestriol (17-epiE3), 16,17-epiestriol (16,17-epiE3), 16-ketoestradiol (16-ketoE2), 16a-hydroxyestrone (16a-OHEl), 2-methoxyestrone (2-MeOEl), 4-methoxyestrone (4-MeOEl), 2-hydroxyestrone-3-methyl ether (3-MeOE1), 2-methoxyestradiol (2-MeOE2), 4-methoxyestradiol (4-MeOE2), 2-hydroxyestrone (20HE1), 4-hydroxyestrone (4-01E1), 2-hydroxyestradiol (2-OHE2), estrone (E1), estrone sulfate (Els), 17a-estradiol (E2a), 17p-estradiol (E2b), estradiol sulfate (E2s), equilin (EQ), 17a-dihydroequilin (EQa), 17p-dihydroequilin (EQb), Eqilenin (EN), 17-dihydroequilenin (ENa) 17β-dihydroequilenin (ENb), A8,9-dehydroestrone (dEl), A8,9-dehydroestrone sulfate (dEls), A9-Tetrahydrocannabinol, Mycophenolic acid.

In embodiments of the first aspect of the present invention, the analyte molecule comprises an amine group as functional group. In embodiments of the first aspect of the present invention, the amine group is an alkyl-amine or an aryl-amine group. In embodiments of the first aspect of the present invention, the analyte comprising one or more amine groups is selected from the group consisting of proteins and peptides. In embodiments of the first aspect of the present invention, the analyte molecule comprising an amine group is selected from the group consisting of 3,4-Methylendioxyamphetamin, 3,4-Methylendioxy-N-ethylamphetamin, 3,4-Methylenedioxymethamphetamine, Amphetamin, Methamphetamin, N-methyl-1,3-benzodioxolylbutanamine, 7-Aminoclonazepam, 7-aminoflunitrazepam, 3,4-Dimethylmethcathinone, 3-Fluoromethcathinone, 4-Methoxymethcathinone, 4-Methylethcathinone, 4-Methylmethcathinone, Amfepramone, Butylone, Ethcathinone, Flephedrone, Methcathinone, Methylone, Methylendioxypyrovaleron, Benzoylecgonine, Dehydronorketamine, Ketamine, Norketamine, Methadone, Normethadone, 6-Acetylmorphine, Diacetylmorphine, Morphine, Norhydrocodone, Oxycodone, Oxymorphone, Phencyclidine, Norpropoxyphene, Amitriptyline, Clomipramine, Dothiepin; Doxepin, Imipramine, Nortriptyline, Trimipramine, Fentanyl, Glycylxylidide, Lidocaine, Monoethylglycylxylidide, N-Acetyl Procainamide, Procainamide, Pregabalin, 2-Methylamino-1-(3,4-methylendioxyphenyl)butan, 2-Amino-1-(3,4-methylendioxyphenyl)butan, Normeperidine, 0-Destramadol, Tramadol, Lidocaine, N-Acetyl Procainamide, Procainamide, Gabapentin, Lamotrigine, Theophyllin, Amikacin, Gentamicin, Tobramycin, Vancomycin, Methotrexat, Gabapentin, Sisomicin, and 5-Methylcytosine.

In embodiments of the first aspect of the present invention, the analyte molecule is a carbohydrate or substance having a carbohydrate moiety, e.g. a glycoprotein or a nucleoside. In embodiments of the first aspect of the present invention, the analyte molecule is a monosaccharide, in particular selected from the group consisting of ribose, desoxyribose, arabinose, ribulose, glucose, mannose, galactose, fucose, fructose, N-acetylglucosamine, N-acetylgalactosamine, neuraminic acid, N-acetylneurominic acid, etc. In embodiments, the analyte molecule is an oligosaccharide, in particular selected from the group consisting of a disaccharide, trisaccharid, tetrasaccharide, polysaccharide. In embodiments of the first aspect of the present invention, the disaccharide is selected from the group consisting of sucrose, maltose and lactose. In embodiments of the first aspect of the present invention, the analyte molecule is a substance comprising above described mono-, di-, tri-, tetra-, oligo- or polysaccharide moiety.

In embodiments of the first aspect of the present invention, the analyte molecule comprises an azide group as functional group which is selected from the group consisting of alkyl or aryl azide. In embodiments of the first aspect of the present invention, the analyte molecule comprising one or more azide groups is selected from the group consisting of Zidovudine and Azidocillin.

Such analyte molecules may be present in biological or clinical samples such as body liquids, e.g. blood, serum, plasma, urine, saliva, spinal fluid, etc., tissue or cell extracts, etc. In embodiments of the first aspect of the present invention, the analyte molecule(s) are present in a biological or clinical sample selected from the group consisting of blood, serum, plasma, urine, saliva, spinal fluid, and a dried blood spot. In some embodiments of the first aspect of the present invention, the analyte molecules may be present in a sample which is a purified or partially purified sample, e.g. a purified or partially purified protein mixture or extract.

In embodiments of the first aspect of the present invention, the reactive unit X is selected from the group consisting of carbonyl reactive unit, diene reactive unit, hydroxyl reactive unit, amino reactive unit, an imine reactive unit, a thiol reactive unit, a diol reactive unit, a phenol reactive unit, epoxide reactive unit, a disulfide reactive unit, and a azido reactive unit.

In embodiments of the first aspect of the present invention, the reactive unit X is a carbonyl reactive unit, which is capable of reacting with any type of molecule having a carbonyl group. In embodiments of the first aspect of the present invention, the carbonyl reactive unit is selected from the group consisting of carboxyl reactive unit, keto reactive unit, aldehyde reactive unit, anhydride reactive unit, carbonyl ester reactive unit, and imide reactive unit. In embodiments of the first aspect of the present invention, the carbonyl-reactive unit may have either a super-nucleophilic N atom strengthened by the a-effect through an adjacent O or N atom NH2-N/O or a dithiol molecule. In embodiments of the first aspect of the present invention, the carbonyl-reactive unit is selected from the group:

(i) a hydrazine unit, e.g. a $H_2N—NH—$, or $H_2N—NR^1—$ unit, wherein $R^1$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, (ii) a hydrazide unit, in particular a carbo-hydrazide or sulfo-hydrazide unit, in particular a $H_2N—NH—C(O)—$, or $H_2N—NR^2—C(O)—$ unit, wherein $R^2$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, (iii) a hydroxylamino unit, e.g. a $H_2N—O—$ unit, and (iv) a dithiol unit, particularly a 1,2-dithiol or 1,3-dithiol unit.

In embodiments of the first aspect of the present invention, wherein the carbonyl reactive unit is a carboxyl reactive unit, the carboxyl reactive units reacts with carboxyl groups on an analyte molecule. In embodiment of the first aspect of the present invention, the carboxyl reactive unit is selected from the group consisting of a diazo unit, an alkylhalide, amine, and hydrazine unit.

In embodiments of the first aspect of the present invention, the reactive unit X is a diene reactive unit, which is capable of reacting with an analyte comprising a diene group. In embodiments of the first aspect of the present invention, the diene reactive unit is selected from the group consisting of Cookson-type reagents, e.g. 1,2,4-triazolin-3,5-diones, which are capable to act as a dienophile.

In embodiments of the first aspect of the present invention, the reactive unit X is a hydroxyl reactive unit, which is capable of reacting with an analyte comprising a hydroxyl group. In embodiments of the first aspect of the present invention, the hydroxyl reactive units is selected from the group consisting of sulfonylchlorides, activated carboxylic esters (NHS, or imidazolide), and fluoro aromates/heteroaromates capable for nucleophilic substitution of the fluorine (T. Higashi J Steroid Biochem Mol Biol. 2016 September; 162:57-69). In embodiments of the first aspect of the present invention, the reactive unit X is a diol reactive unit which reacts with an diol group on an analyte molecule. In embodiments of the first aspect of the present invention, wherein the reactive unit is a 1,2 diol reactive unit, the 1,2 diol reactive unit comprises boronic acid. In further embodiments, diols can be oxidised to the respective ketones or aldehydes and then reacted with ketone/aldehyde-reactive units X.

In embodiments of the first aspect of the present invention, the amino reactive unit reacts with amino groups on an analyte molecule. In embodiments of the first aspect of the present invention, the amino-reactive unit is selected from the group consisting of active ester group such as N-hydroxy succinimide (NHS) ester or sulfo-NHS ester, pentafluoro phenyl ester, cabonylimidazole ester, quadratic acid esters, a hydroxybenzotriazole (HOBt) ester, 1-hydroxy-7-azabenzotriazole (HOAt) ester, and a sulfonylchloride unit.

In embodiments of the first aspect of the present invention, the thiol reactive unit reacts with an thiol group on an analyte molecule. In embodiments of the first aspect of the present invention, the thiole reactive unit is selected from the group consisting of haloacetyl group, in particular selected from the group consisting of Br/I-CH2-C(=O)— unit, acrylamide/ester unit, unsaturated imide unit such as maleimide, methylsulfonyl phenyloxadiazole and sulfonylchloride unit.

In embodiments of the first aspect of the present invention, the phenol reactive unit reacts with phenol groups on an analyte molecule. In embodiments of the first aspect of the present invention, the phenol-reactive unit is selected from the group consisting of active ester unit such as N-hydroxy succinimide (NHS) ester or sulfo-NHS ester, pentafluoro phenyl ester, carbonylimidazole ester, quadratic acid esters, a hydroxybenzotriazole (HOBt) ester, 1-hydroxy-7-azabenzotriazole (HOAt) ester, and a sulfonylchloride unit. Phenol groups present on an analyte molecule can be reacted with triazole dione via a reaction (H. Ban et al J. Am. Chem. Soc., 2010, 132 (5), pp 1523-1525) or by diazotization or alternatively by ortho nitration followed by reduction to an amine which could then be reacted with an amine reactive reagent.

In embodiments of the first aspect of the present invention, the reactive unit X is a epoxide reactive unit, which is capable of reacting with an analyte comprising a epoxide group. In embodiments of the first aspect of the present invention, the epoxide reactive unit is selected from the group consisting of amino, thiol, super-nucleophilic N atom strengthened by the a-effect through an adjacent 0 or N atom NH2-N/O molecule. In embodiments of the first aspect of the present invention, the epoxide reactive unit is selected from the group:

(i) a hydrazine unit, e.g. a $H_2N$—NH—, or $H_2N$—$NR^1$— unit, wherein $R^1$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, (ii) a hydrazide unit, in particular a carbo-hydrazide or sulfo-hydrazide unit, in particular a $H_2N$—NH—C (O)—, or $H_2N$—$NR^2$—C(O)— unit, wherein $R^2$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, and (iii) a hydroxylamino unit, e.g. a $H_2N$—O— unit.

In embodiments of the first aspect of the present invention, the reactive unit X is a disulfide reactive unit, which is capable of reacting with an analyte comprising a disulfide group. In embodiments of the first aspect of the present invention, the disulfide reactive unit is selected from the group consisting of thiol. In further embodiments, disulfide group can be reduced to the respective thiol group and then reacted with thiol reactive units X.

In embodiments of the first aspect of the present invention, the reactive unit X is a azido reactive unit which reacts with azido groups on an analyte molecule. In embodiments of the first aspect of the present invention, the azido-reactive unit reacts with azido groups through azide-alkyne cycloaddition. In embodiments of the first aspect of the present invention, the azido-reactive unit is selected from the group consisting of alkyne (alkyl or aryl), linear alkyne or cyclic alkyne. The reaction between the azido and the alkyne can proceed with or without the use of a catalyst. In further embodiments of the first aspect of the present invention the azido group can be reduced to the respective amino group and then reacted with amino reactive units X.

The compounds of formula A comprise a neutral loss unit Y. The neutral loss unit Y is able to loose a moiety (a neutral entity) having no charge. The neutral loss unit Y is capable of fragmentation, i.e. under conditions of MS, e.g. when subjected to collision-induced dissociation (CID), for example in triple quadrupole MS, whereby a neutral entity is released. The lost neutral entity is a single atom or a plurality of atoms. After release of the neutral entity, the remainder of neutral loss unit Y still remains neutral. Typically, but not necessarily, one neutral entity is released. In particular embodiments of the first aspect of the present invention, two neutral entity are released.

In embodiments of the first aspect of the present invention, the neutral loss unit Y releases at least one neutral entity upon ionization. The neutral entity is a low molecular weight neutral entity, in particular in a range of 10-100 Da, in particular 20-80 Da, in particular 25-65 Da. In particular, the neutral entity has a molecular weight of 100 Da or less, in particular of 80 Da or less, in particular of 70 Da or less, in particular of 50 Da or less, in particular of 30 Da or less.

In embodiments of the first aspect of the present invention, the neutral entity is selected from the group consisting of $N_2$, NO, $NO_2$, $S_2$, SO, $SO_2$, CO, $CO_2$. In particular embodiments, the neutral entity is $N_2$.

In embodiments of the first aspect of the present invention, the loss of the neutral entity leads to a reduction of the mass/charge ratio (m/z) by −28 Da (in case $N_2$ or CO is lost), −30 Da (in case NO is lost), −44 Da (in case $CO_2$ is lost), −46 Da (in case $NO_2$ is lost), −48 Da (in case SO is lost), −64 Da (in case $S_2$ or $SO_2$ is lost), or −87 Da (in case N2 and Trimethylamin are lost).

In embodiments of the first aspect of the present invention, one neutral entity is released. In embodiments of the first aspect of the present invention, two neutral entities are released. In particular, the second released neutral entity is different from the first released neutral entity. The release of the second neutral entity occurs concurrently or subsequently to the release of the first neutral entity. In particular, the release of the second neutral entity occurs concurrently to the release of the first neutral entity, i.e. both neutral entity are released at once, i.e in one single fragmentation event.

In embodiments of the first aspect of the present invention, the neutral loss unit Y comprises or consists of a cyclic moiety which is capable of fragmentation. In embodiments of the first aspect of the present invention, the neutral loss unit Y comprises or consists of a 4-, 5- or 6-membered heterocyclic moiety, particularly a 4-, 5-, 6-membered heterocyclic moiety having at least 2 heteroatoms adjacent to each other, in particular two N atoms adjacent to each other. In embodiment of the first aspect of the present invention, the neutral loss unit Y comprises or consists of triazole, tetrazole, tetrazine, oxadiazole, thiadiazole moiety or a hydrogenated derivative thereof. In embodiments of the first aspect of the present invention, the neutral loss unit Y comprises or consists a 1,2,3-triazole, 1,2,4-triazole moiety, 1,4,5-triazole, 3,4,5-triazole moiety, a 1,2,3,4-tetrazole, 2,3,4,5-tetrazole or a 2,3,5,6 tetrazole moiety, or a 1,2,4,5 tetrazine moiety. In embodiments of the first aspect of the present invention, the neutral loss unit Y comprises or consists a 1,2,3-triazole or 1,2,4-triazol moiety, or a 1,2,3,4-tetrazole moiety, or a 1,2,4,5 tetrazine moiety.

In embodiments of the first aspect of the present invention, the charged unit Z is permanently charged, in particular under neutral conditions, in particular at a pH value of 6-8.

In embodiments of the first aspect of the present invention, the charged unit Z is positively or negatively charged, preferably positively charged.

In embodiments of the first aspect of the present invention, the charged unit Z comprises or consists of (i) at least one positively charged moiety.

or (ii) at least one negatively charged moiety.

In embodiments of the first aspect of the present invention, the charged unit Z is a positively charged unit. In embodiments of the first aspect of the present invention, the positively charged unit Z, is choosen in a manner that the resulting compound of formula A has a pKa of 10 or higher, more particularly has a pKa of 12 or higher. In embodiments of the first aspect of the present invention, the positively charged unit Z is selected from the group consisting of primary, secondary, tertiary or quaternary ammonium, sulfonium, imidazolium, pyridinium, or a phosphonium. In particular embodiments of the first aspect, the positively charged moiety is tri-methyl-ammonium, N,N-dimethyl-piperidinium or N-alkyl-quinuclidinium.

In embodiments of the first aspect of the present invention, the charged unit Z is a negatively charged unit. In embodiments of the first aspect of the present invention, the negatively charged unit Z is choosen in a manner that the resulting compound of formula A has a pKb of 10 or higher, more particularly has a pKb of 12 or higher. In embodiments of the first aspect of the present invention, the negatively charged unit Z is selected from the group consisting of a phosphate, sulphate, sulphonate or carboxylate.

In embodiments of the first aspect of the present invention, the linker L1 and L2 are independently of each other linear linker. In embodiments of the first aspect, the linear linker L1 and L2 are independently of each other a single bond between two functional units of the compound of formula A, or comprise 1 to 10 C-atoms, in particular 1 to 6 C-atoms, in particular 1, 2, or 3 C-atoms. In embodiments of the first aspect, the linear linker L1 and L2 comprises independently of each other 1 or more heteroatoms, in particular N, O or S. In embodiments of the first aspect of the present invention, the linker L1 and L2 are independently of each other substituted or unsubstituted, in particular the linker L1 and L2 are unsubstituted. In embodiments of the first aspect of the present invention, the linker L1 and/or L2 is not protonatable. In embodiments of the first aspect of the present invention, the linear linker L1 and/or L2 comprises a stabilizing unit. In embodiments of the first aspect of the present invention, the stabilizing unit prevents the loss of the charged unit Z during the fragmentation event. In embodiments of the first aspect of the present invention, the stabilizing unit prevents the loss of the charged unit Z by destabilizing the potentially formed carbo-kation. In embodiments of the first aspect of the present invention, the stabilising unit is separated by one C atom from the charged unit Z. In embodiments of the first aspect of the present invention, the stabilising unit comprises at least one heteroatom. In embodiments of the first aspect of the present invention, the stabilising unit is selected from the group consisting of CO, or isoelectrical analogons thereof such as SO or SO2. In embodiments of the first aspect, the linear linker L1 is a single bond connecting the reactive unit and the neutral loss unit, and the linker L2 is 1 or 2 C-atoms, optionally comprising one or two heteroatoms, in particular 1 or 2 O-atoms, connecting the neutral loss unit and the positively charged unit of the compound of formula A. In embodiments of the first aspect, the linear linker L1 comprises 1 C-atom connecting the reactive unit and the neutral loss unit, and the linker L2 comprises 1 or 2 C-atoms and 1 O-atom connecting the neutral loss unit and the positively charged unit of the compound of formula A. In embodiments of the first aspect, the linear linker L1 comprises 3 C-atoms and one O-atom connecting the reactive unit and the neutral loss unit, and the linker L2 comprises 1 C-atom and 1 O-atom connecting the neutral loss unit and the positively charged unit of the compound of formula A. In embodiments of the first aspect, the linear linker L1 comprises 6 C-atoms and one 0-atom connecting the reactive unit and the neutral loss unit, and the linker L2 comprises 2 C-atoms and 1 O-atom connecting the neutral loss unit and the positively charged unit of the compound of formula A. In embodiments of the first aspect, the linear linker L1 comprises 7 C-atoms and 1 O-atom connecting the reactive unit and the neutral loss unit, and the linker L2 is a single bond connecting the neutral loss unit and the positively charged unit of the compound of formula A.

In embodiments of the first aspect of the present invention, the compound has a structure of formula A, wherein the reactive unit X is a carbonyl-reactive unit, neutral loss unit Y is a 5-membered heterocyclic unit, and the charged unit Z is a permanently positively charged unit.

In embodiments of the first aspect of the present invention, the compound has a structure of formula A, wherein the reactive unit X is a diene reactive unit, the neutral loss unit Y is a 5-membered heterocyclic unit, and the charged unit Z is a permanently positively charged unit.

In embodiments of the first aspect of the present invention, the compound has a structure of formula A, wherein the reactive unit X is a hydrazine unit, the neutral loss unit Y is a 5-membered heterocyclic moiety comprising at least 3 heteroatoms, and the charged unit Z is a tertiary ammonium group.

In embodiments of the first aspect of the present invention, the compound has a structure of formula A, wherein the reactive unit X is a hydrazide unit, the neutral loss unit Y is a 5-membered heterocyclic unit comprising at least 3 heteroatoms, and the charged unit Z is a tertiary ammonium group.

In embodiments of the first aspect of the present invention, the compound has a structure of formula A, wherein the reactive unit X is a hydrazine unit, the neutral loss unit Y is a 5-membered heterocyclic moiety comprising at least 3 heteroatoms, and the charged unit Z is a piperidine unit.

In embodiments of the first aspect of the present invention, the compound has a structure of formula A, wherein the reactive unit X is a hydrazide unit, the neutral loss unit Y is a 5-membered heterocyclic unit comprising at least 3 heteroatoms, and the charged unit Z is a piperidine unit.

In embodiments of the first aspect of the present invention, the compound has a structure of formula A, wherein the reactive unit X is a hydrazine unit, the neutral loss unit Y is a 5-membered heterocyclic moiety comprising at least 3 heteroatoms, and the charged unit Z is a pyridine unit.

In embodiments of the first aspect of the present invention, the compound has a structure of formula A, wherein the reactive unit X is a hydrazide unit, the neutral loss unit Y is a 5-membered heterocyclic unit comprising at least 3 heteroatoms, and the charged unit Z is a pyridine unit.

In embodiments of the first aspect of the present invention, the compound has a structure of formula A, wherein the reactive unit X is a Cookson-type reagent, the neutral loss unit Y is a 5-membered heterocyclic unit comprising at least 3 heteroatoms, and the charged unit Z is a tertiary ammonium group.

In embodiments of the first aspect of the present invention, the compound has a structure of formula A, wherein the reactive unit X is a Cookson-type reagent, the neutral loss unit Y is a 5-membered heterocyclic unit comprising at least 3 heteroatoms, and the charged unit Z is a piperidine unit.

In embodiments of the first aspect of the present invention, the compound has a structure of formula A, wherein the reactive unit X is a Cookson-type reagent, the neutral loss unit Y is a 5-membered heterocyclic unit comprising at least 3 heteroatoms, and the charged unit Z is a pyridine unit.

In embodiments of the first aspect of the present invention, the compound has a structure of formula A, wherein the reactive unit X is $H_2N$—NH—, the neutral loss unit Y is 1,2,3-triazole, 1,2,4-triazol, 1,2,3,4-tetrazole, or 1,2,4,5-tetrazine, and the charged unit Z is a tertiary ammonium unit.

In embodiments of the first aspect of the present invention, the compound has a structure of formula A, wherein the reactive unit X is $H_2N—NH—$, the neutral loss unit Y is 1,2,3-triazole, 1,2,4-triazol, 1,2,3,4-tetrazole, or 1,2,4,5-tetrazine, and the charged unit Z is a piperidine unit.

In embodiments of the first aspect of the present invention, the compound has a structure of formula A, wherein the reactive unit X is $H_2N—NH—$, the neutral loss unit Y is 1,2,3-triazole, 1,2,4-triazol, 1,2,3,4-tetrazole, or 1,2,4,5-tetrazine, and the charged unit Z is a pyridine unit.

In embodiments of the first aspect of the present invention, the compound has a structure of formula A, wherein the reactive unit X is $H_2N—O—C—$, the neutral loss unit Y is 1,2,3-triazole, 1,2,4-triazol, 1,2,3,4-tetrazole, or 1,2,4,5-tetrazine, and the charged unit Z is a dimethyl-piperidine or quinuclidine unit.

In embodiments of the first aspect of the present invention, the compound has a structure of formula A, wherein the reactive unit X is 1,2,4-triazolin-3,5-dione, the neutral loss unit Y is 1,2,3-triazole, 1,2,4-triazol, 1,2,3,4-tetrazole, or 1,2,4,5-tetrazine, and the charged unit Z is a dimethyl-piperidine or quinuclidine moiety.

In embodiments of the first aspect of the present invention, the compound of formula A is selected from the group consisting of (i) Label 1

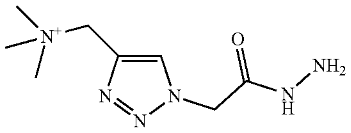

(ii) Label 2

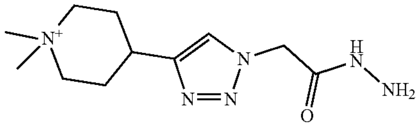

and (iii) Label 3

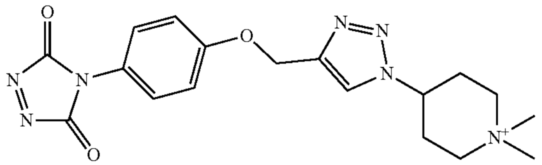

Further examples of the compound of formula A are the following (iv) Label 4

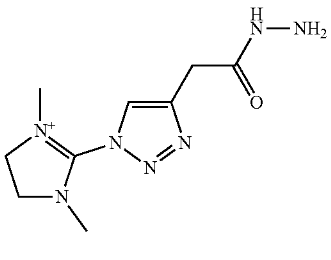

-continued (v) Label 5

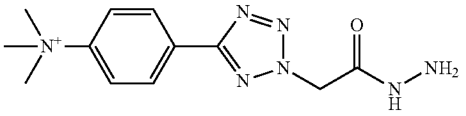

(vi) Label 6

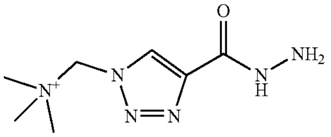

(vii) Label 7

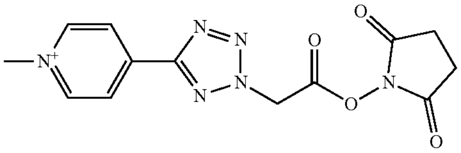

(viii) Label 8

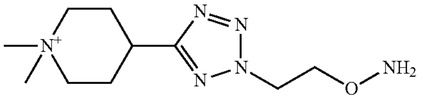

(ix) Label 9

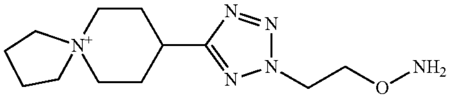

(x) Label 10

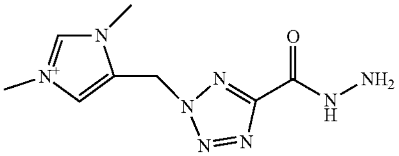

(xi) Label 11

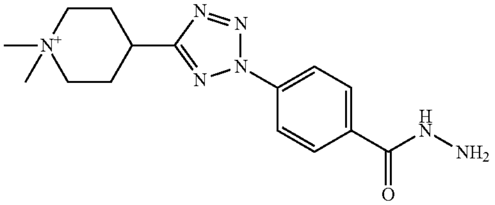

(xii) Label 12

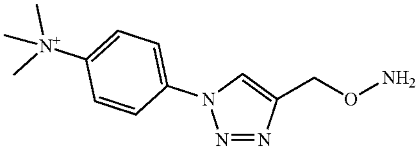

In a second aspect, the present invention relates to a composition comprising the compound of formula A as disclosed in detail above with regard to first aspect of the present invention.

In a third aspect, the present invention relates to a kit comprising the compound of formula A as disclosed in detail herein above with regard to first aspect of the present invention or the composition of the second aspect of the present invention as disclosed in detail herein above.

In a fourth aspect, the present invention relates to an adduct formed by the reaction of an analyte molecule and the compound A of the first aspect of the present invention as disclosed herein above, wherein the analyte molecule and compound A of the first aspect of the present invention are covalently linked to each other. In embodiments, the adduct has a structure of formula A':

T-X'-L1-Y-L2-Z wherein
T is an analyte molecule
X' is a moiety resulting from the chemical reaction of a reactive unit X of compound of formula A with an analyte molecule T,
L1 and L2 are independently of each other substituted or unsubstituted linker, in particular linear linker,
Y is a neutral loss unit, and
Z is a charged unit comprising at least one permanently charged moiety, in particular one permanently charged moiety,
including any salt thereof.

In embodiments of the fourth aspect of the present invention, the adduct of formula A' comprises X' resulting from the formation of a covalent bond between the reactive unit X of compound of formula A with a functional group present in the analyte molecule T. Depending on the reactive unit X of the compound of formula A, and the functional group of the analyte molecule T, the skilled person is well able to determine the covalent bond formed between the two.

In embodiments of the fourth aspect of the present invention, the analyte molecule comprises a functional group selected from the group consisting of carbonyl group, diene group, hydroxyl group, amine group, imine group, thiol group, diol group, phenolic group, expoxid group, disulfide group, and azide group, each of which is capable of forming a covalent bond with reactive unit X of compound of formula A. Further, it is also contemplated within the scope of the present invention that a functional group present on an analyte molecule would be first converted into another group that is more readily available for reaction with reactive unit X of compounds of formula A.

In embodiments of the fourth aspect of the present invention, the analyte molecule is selected from the group consisting of steroids, ketosteroids, secosteroids, amino acids, peptides, proteins, carbohydrates, fatty acids, lipids, nucleosides, nucleotides, nucleic acids and other biomolecules including small molecule metabolites and cofactors as well as therapeutic drugs, drugs of abuse, toxins or metabolites thereof.

In embodiments of the fourth aspect of the present invention, the analyte molecule comprises a carbonyl group as functional group which is selected from the group consisting of a carboxylic acid group, aldehyde group, keto group, a masked aldehyde, masked keto group, ester group, amide group, and anhydride group.

In embodiments of the fourth aspect of the present invention, wherein the carbonyl group is an amide group, the skilled person is well-aware that the amide group as such is a stable group, but that it can be hydrolized to convert the amide group into an carboxylic acid group and an amino group. Hydrolysis of the amide group may be achieved via acid/base catalysed reaction or by enzymatic process either of which is well-known to the skilled person. In embodiments of the fourth aspect of the present invention, wherein the carbonyl group is a masked aldehyde group or a masked keto group, the respective group is either a hemiacetal group or acetal group, in particular a cyclic hemiacetal group or acetal group. In embodiments of the fourth aspect of the present invention, the acetal group, is converted into an aldehyde or keto group before reaction with the compound of formula A.

In embodiments of the fourth aspect of the present invention, the carbonyl group is a keto group. In embodiments of the fourth aspect of the present invention, the keto group may be transferred into an intermediate imine group before reacting with the reactive unit of compounds of formula A. In embodiments of the fourth aspect of the present invention, the analyte molecule comprising one or more keto groups is a ketosteroid. In particular embodiments of the fourth aspect of the present invention, the ketosteroid is selected from the group consisting of testosterone, epitestosterone, dihydrotestosterone (DHT), desoxymethyltestosterone (DMT), tetrahydrogestrinone (THG), aldosterone, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17-OH pregnenolone, 17-OH progesterone, 17-OH progesterone, androsterone, epiandrosterone, and delta 4 androstenedione) 11-desoxycortisol corticosterone, 21-deoxycortisol, 11-deoxycorticosterone, allopregnanolone, and aldosterone.

In embodiments of the fourth aspect of the present invention, the carbonyl group is a carboxyl group. In embodiments of the fourth aspect of the present invention, the carboxyl group reacts directly with the compound of formula A or it is converted into an activated ester group before reaction with the compound of formula A. In embodiments of the fourth aspect of the present invention, the analyte molecule comprising one or more carboxyl groups is selected from the group consisting of A8-Tetrahydrocannabinol-acid, Benzoylecgonin, Salicylic acid, 2-hydroxybenzoic acid, Gabapentin, Pregabalin, Valproic acid, Vancomycin, Methotrexat, Mycophenolic acid, Montelukast, Repaglinide, Furosemide, Telmisartan, Gemfibrozil, Diclorofenac, Ibuprofen, Indomethacin, Zomepirac, Isoxepac, and Penicilin. In embodiments of the fourth aspect of the present invention, the analyte molecule comprising one or more carboxyl groups is an amino acid selected from the group consisting of arginine, lysine, aspartic acid, glutamic acid, glutamine, asparagine, histidine, serine, threonine, tyrosine, cysteine, tryptophan, alanine, isoleucine, leucine, methionine, phenyalanine, valine, proline, and glycine.

In embodiments of the fourth aspect of the present invention, the carbonyl group is an aldehyde group. In embodiments of the fourth aspect of the present invention, the aldehyde group may be transferred into an intermediate imine group before reacting with the reactive unit of compounds of formula A. In embodiments of the fourth aspect of the present invention, the analyte molecule comprising one or more aldehyde groups is selected from the group consisting of Pyridoxal, N-Acetyl-D-glucosamine, Alcaftadine, Streptomycin, Josamycin.

In embodiments of the fourth aspect of the present invention, the carbonyl group is an carbonyl ester group. In embodiments of the fourth aspect of the present invention, the analyte molecule comprising one or more ester groups is selected from the group consisting of Cocaine, Heroin, Ritalin, Aceclofenac, Acetycholine, Amcinonide, Amiloxate, amylocaine, Anileridine, Aranidipine, and Artesunate, Pethidine.

In embodiments of the fourth aspect of the present invention, the carbonyl group is an anhydride group. In embodiments of the fourth aspect of the present invention, the analyte molecule comprising one or more anhydride groups is selected from the group consisting of Cantharidin, Succinic Anhydride, Trimellitic Anhydride, and Maleic Anhydride.

In embodiments of the fourth aspect of the present invention, the analyte molecule comprises one or more diene groups, in particular to conjugated diene groups, as functional group. In embodiments of the fourth aspect of the present invention, the analyte molecule comprising one or more diene groups is a secosteroid. In embodiments, the secosteroid is selected from the group consisting of Cholecalciferol (Vitamin D3), Ergocalciferol (Vitamin D2), Calcidiol, Calcitriol, Tachysterol, Lumisterol und Tacalcitol. In particular, the secosteroid is Vitamin D, in particular Vitamin D2 or D3 or derivates thereof. In particular embodiments, the secosteroid is selected from the group consisting of Vitamin D2, Vitamin D3, 25-Hydroxy Vitamin D2, 25-Hydroxy Vitamin D3, 3-Epi-25-Hydroxy Vitamin D2, 3-Epi-25-Hydroxy Vitamin D3, 1,25-Dihydroxy Vitamin D2, 1,25-Dihydroxy Vitamin D3, 24,25-Dihydroxy Vitamin D2, and 24,25-Dihydroxy Vitamin D3, Vitamin A, Tretinoin, Isotretinoin, Alitretinoin, Natamycin, Sirolimus, Amphotericin B, Nystatin, Everolimus, Temsirolimus, Fidaxomicin.

In embodiments of the fourth aspect of the present invention, the analyte molecule comprises one or more hydroxyl group as functional group. In embodiments of the fourth aspect of the present invention, the analyte molecule comprises a single hydroxyl group or two hydroxyl groups. In embodiments wherein more than one hydroxyl group is present, the two hydroxyl groups may be positioned adjacent to each other (1,2 diol) or may be separated by 1, 2, or 3 C-atoms (1,3-diol, 1,4-diol, 1,5-diol, respectively). In particular embodiments of the fourth aspect, the analyte molecule comprises an 1,2 diol group. In embodiments, wherein only one hydroxyl group is present, said analyte is selected from the group consisting of primary alcohol, secondary alcohol and tertiary alcohol. In embodiments of the fourth aspect of the present invention, wherein the analyte molecule comprises one or more hydroxyl groups, the analyte is selected from the group consisting of Benzyl alcohol, Menthol, L-Carnitine, Pyridoxine, Metronidazole, Isosorbide mononitrate, Guaifenesin, Clavulanate, Migitol, Zalcitabine, Isoprenaline, Aciclovir, Methocarbamol, Tramadol, Venlafaxine, Atropine, Clofedanol, alpha-Hydroxyalprazolam, Alpha-Hydroxytriazolam, Lorazepam, Oxazepam, Tamazepam, Ethylglucuronide, Ethylmorphine, Morphine, Morphine-3-glucuronide, Buprenorphine, Codeine, Dihydrocodeine, p-Hydroxypropoxyphene, O-desmethyltramadol, Dihydroquinidine, Quinidine. In embodiments of the fourth aspect of the present invention, wherein the analyte molecule comprises more than one hydroxyl groups, the analyte is selected from the group consisting of Vitamin C, Glucosamine, Mannitol, Tetrahydrobiopterin, Cytarabine, Azacitidine, Ribavirin, Floxuridine, Gemcitadine, Streptozocin, Adenosine, Vibarabine, Cladribine, Estriol, Trifluridine, Clofarabine, Nadolol, Zanamivir, Lactulose, Adenosine monophosphate, Idoxuridine, Regadenoson, Lincomycin, Clindamycin, Canaglifozin, Tobramycin, Netilmicin, Kanamycin, Ticagrelor, Epirubicin, Doxorubicin, Arbekacin, Steptomycin, Quabain, Amikacin, Neomycin, Framycetin, Paromomycin, Erythromycin, Clarithromycin, Azithromycin, Vindesine, Digitoxin, Digoxin, Metrizamide, Acetyldigitoxin, Deslanoside, Fludaradine, Clofarabine, Gemcitabine, Cytarabine, Capecitabine, Vidarabine, Trifluridine, Idoxuridine, and Plicamycin.

In embodiments of the fourth aspect of the present invention, the analyte molecule comprises one or more thiol group (including but not limited to alkyl-thiol and thiol-ary groups) as functional group. In embodiments of the fourth aspect of the present invention, the analyte molecule comprising one or more thiol groups is selected from the group consisting of Thiomandelic acid, DL-Captopril, DL-Thiorphan, N-Acetylcysteine, D-Penicillamine, Glutathione, L-Cysteine, Zefenoprilat, Tiopronin, Dimercaprol, Succimer.

In embodiments of the fourth aspect of the present invention, the analyte molecule comprises one or more disulfide group as functional group. In embodiments of the fourth aspect of the present invention, the analyte molecule comprising one or more disulfide groups is selected from the group consisting of Glutathione Disulfide, Dipyrithione, Selenium Sulfide, Disulfiram, Lipoic Acid, L-Cystine, Fursultiamine, Octreotide, Desmopressin, Vapreotide, Terlipressin, Linaclotide, Peginesatide.

In embodiments of the fourth aspect of the present invention, the analyte molecule comprises one or more epoxide group as functional group. In embodiments of the fourth aspect of the present invention, the analyte molecule comprising one or more epoxide groups is selected from the group consisting of Carbamazepine 10,11 epoxide, Carfilzomib, Furosemide epoxide, and Fosfomycin, Sevelamer, Cerulenin, Scopolamine, Tiotropium, Methylscopolamine bromide, Eplerenone, Mupirocin, Natamycin, Carfilzomib, Troleandomycin.

In embodiments of the fourth aspect of the present invention, the analyte molecule comprises one or more phenol groups as functional group. In particular embodiments of the fourth aspect of the present invention, analyte molecules comprising one or more phenol groups are steroids or steroid-like compounds. In embodiments of the fourth aspect of the present invention, the analyte molecule comprising one or more phenol groups is a steroid or a steroid-like compound having an A-ring which is $sp^2$ hybridized and an OH group at the 3-position of the A-ring. In particular embodiments of the fourth aspect of the present invention, the steroid or steroid-like analyte molecule is selected from the group consisting of estrogen, estrogen-like compounds, estrone (E1), estradiol (E2), 17a-estradiol, 17p-estradiol, estriol (E3), 16-epiestriol, 17-epiestriol, and 16, 17-epiestriol, and/or metabolites thereof. In embodiments, the metabolites is selected from the group consisting of estriol, 16-epiestriol (16-epiE3), 17-epiestriol (17-epiE3), 16,17-epiestriol (16,17-epiE3), 16-ketoestradiol (16-ketoE2), 16a-hydroxyestrone (16a-OHEl), 2-methoxyestrone (2-MeOEl), 4-methoxyestrone (4-MeOEl), 2-hydroxyestrone-3-methyl ether (3-MeOEl), 2-methoxyestradiol (2-MeOE2), 4-methoxyestradiol (4-MeOE2), 2-hydroxyestrone (20HE1), 4-hydroxyestrone (4-OHE1), 2-hydroxyestradiol (2-OHE2), estrone (E1), estrone sulfate (Els), 17a-estradiol (E2a), 17p-estradiol (E2b), estradiol sulfate (E2s), equilin (EQ), 17a-dihydroequilin (EQa), 17p-dihydroequilin (EQb), Eqilenin (EN), 17-dihydroequilenin (ENa) 17p-dihydroequilenin (ENb), A8,9-dehydroestrone (dEl), A8,9-dehydroestrone sulfate (dEls), A9-Tetrahydrocannabinol, Mycophenolic acid.

In embodiments of the fourth aspect of the present invention, the analyte molecule comprises an amine group as functional group. In embodiments of the fourth aspect of the present invention, the amine group is an alkyl-amine or an aryl-amine group. In embodiments of the fourth aspect of the present invention, the analyte comprising one or more amine groups is selected from the group consisting of proteins and peptides. In embodiments of the fourth aspect of the present invention, the analyte molecule comprising an amine group is selected from the group consisting of 3,4-Methylendioxyamphetamin, 3,4-Methylendioxy-N-ethylamphetamin, 3,4-Methylenedioxymethamphetamine, Amphetamin, Methamphetamin, N-methyl-1,3-benzodioxolylbutanamine, 7-Aminoclonazepam, 7-aminoflunitrazepam, 3,4-Dimethylmetheathinone, 3-Fluorometheathinone, 4-Methoxymethcathinone, 4-Methylethcathinone, 4-Methylmethcathinone, Amfepramone, Butylone, Ethcathinone, Flephedrone, Methcathinone, Methylone, Methylendioxypyrovaleron, Benzoylecgonine, Dehydronorketamine, Ketamine, Norketamine, Methadone, Normethadone, 6-Acetylmorphine, Diacetylmorphine, Morphine, Norhydrocodone, Oxycodone, Oxymorphone, Phencyclidine, Norpropoxyphene, Amitriptyline, Clomipramine, Dothiepin, Doxepin, Imipramine, Nortriptyline, Trimipramine, Fentanyl, Glycylxylidide, Lidocaine, Monoethylglycylxylidide, N-Acetyl Procainamide, Procainamide, Pregabalin, 2-Methylamino-1-(3,4-methylendioxyphenyl)butan, 2-Amino-1-(3,4-methylendioxyphenyl)butan, Normeperidine, 0-Destramadol, Tramadol, Lidocaine, N-Acetyl Procainamide, Procainamide, Gabapentin, Lamotrigine, Theophyllin, Amikacin, Gentamicin, Tobramycin, Vancomycin, Methotrexat, Gabapentin, Sisomicin, and 5-Methylcytosine.

In embodiments of the fourth aspect of the present invention, the analyte molecule is a carbohydrate or substance having a carbohydrate moiety, e.g. a glycoprotein or a nucleoside. In embodiments of the fourth aspect of the present invention, the analyte molecule is a monosaccharide, in particular selected from the group consisting of ribose, desoxyribose, arabinose, ribulose, glucose, mannose, galactose, fucose, fructose, N-acetylglucosamine, N-acetylgalactosamine, neuraminic acid, N-acetylneurominic acid, etc. In embodiments, the analyte molecule is an oligosaccharide, in particular selected from the group consisting of a disaccharide, trisaccharid, tetrasaccharide, polysaccharide. In embodiments of the fourth aspect of the present invention, the disaccharide is selected from the group consisting of sucrose, maltose and lactose. In embodiments of the fourth aspect of the present invention, the analyte molecule is a substance comprising above described mono-, di-, tri-, tetra-, oligo- or polysaccharide moiety.

In embodiments of the fourth aspect of the present invention, the analyte molecule comprises an azide group as functional group which is selected from the group consisting of alkyl or aryl azide. In embodiments of the fourth aspect of the present invention, the analyte molecule comprising one or more azide groups is selected from the group consisting of Zidovudine and Azidocillin.

Such analyte molecules may be present in biological or clinical samples such as body liquids, e.g. blood, serum, plasma, urine, saliva, spinal fluid, etc., tissue or cell extracts, etc. In embodiments of the fourth aspect of the present invention, the analyte molecule(s) are present in a biological or clinical sample selected from the group consisting of blood, serum, plasma, urine, saliva, spinal fluid, and a dried blood spot. In some embodiments of the fourth aspect of the present invention, the analyte molecules may be present in a sample which is a purified or partially purified sample, e.g. a purified or partially purified protein mixture or extract.

In embodiments of the fourth aspect of the present invention, the reactive unit X is selected from the group consisting of carbonyl reactive unit, diene reactive unit, hydroxyl reactive unit, amino reactive unit, an imine reactive unit, a thiol reactive unit, a diol reactive unit, a phenol reactive unit, epoxide reactive unit, a disulfide reactive unit, and a azido reactive unit.

In embodiments of the fourth aspect of the present invention, the reactive unit X is a carbonyl reactive unit, which is capable of reacting with any type of molecule having a carbonyl group. In embodiments of the fourth aspect of the present invention, the carbonyl reactive unit is selected from the group consisting of carboxyl reactive unit, keto reactive unit, aldehyde reactive unit, anhydride reactive unit, carbonyl ester reactive unit, and imide reactive unit. In embodiments of the fourth aspect of the present invention, the carbonyl-reactive unit may have either a super-nucleophilic N atom strengthened by the a-effect through an adjacent O or N atom NH2-N/O or a dithiol molecule. In embodiments of the fourth aspect of the present invention, the carbonyl-reactive unit is selected from the group:

(i) a hydrazine unit, e.g. a $H_2N$—NH—, or $H_2N$—$NR^1$— unit, wherein $R^1$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, (ii) a hydrazide unit, in particular a carbo-hydrazide or sulfo-hydrazide unit, in particular a $H_2N$—NH—C(O)—, or $H_2N$—$NR^2$—C(O)— unit, wherein $R^2$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, (iii) a hydroxylamino unit, e.g. a $H_2N$—O— unit, and (iv) a dithiol unit, particularly a 1,2-dithiol or 1,3-dithiol unit.

In embodiments of the fourth aspect of the present invention, wherein the carbonyl reactive unit is a carboxyl reactive unit, the carboxyl reactive units reacts with carboxyl groups on an analyte molecule. In embodiment of the fourth aspect of the present invention, the carboxyl reactive unit is selected from the group consisting of a diazo unit, an alkylhalide, amine, and hydrazine unit.

In embodiments of the fourth aspect of the present invention, the reactive unit X is a diene reactive unit, which is capable of reacting with an analyte comprising a diene group. In embodiments of the fourth aspect of the present invention, the diene reactive unit is selected from the group consisting of Cookson-type reagents, e.g. 1,2,4-triazolin-3,5-diones, which are capable to act as a dienophile.

In embodiments of the fourth aspect of the present invention, the reactive unit X is a hydroxyl reactive unit, which is capable of reacting with an analyte comprising a hydroxyl group. In embodiments of the fourth aspect of the present invention, the hydroxyl reactive units is selected from the group consisting of sulfonylchlorides, activated carboxylic esters (NHS, or imidazolide), and fluoro aromates/heteroaromates capable for nucleophilic substitution of the fluorine (T. Higashi J Steroid Biochem Mol Biol. 2016 September; 162:57-69). In embodiments of the fourth aspect of the present invention, the reactive unit X is a diol reactive unit which reacts with an diol group on an analyte molecule. In embodiments of the fourth aspect of the present invention, wherein the reactive unit is a 1,2 diol reactive unit, the 1,2 diol reactive unit comprises boronic acid. In further embodiments, diols can be oxidised to the respective ketones or aldehydes and then reacted with ketone/aldehyde-reactive units X.

In embodiments of the fourth aspect of the present invention, the amino reactive unit reacts with amino groups on an analyte molecule. In embodiments of the fourth aspect of the present invention, the amino-reactive unit is selected from the group consisting of active ester group such as N-hydroxy succinimide (NHS) ester or sulfo-NHS ester, pentafluoro phenyl ester, cabonylimidazole ester, quadratic acid esters, a hydroxybenzotriazole (HOBt) ester, 1-hydroxy-7-azabenzotriazole (HOAt) ester, and a sulfonylchloride unit.

In embodiments of the fourth aspect of the present invention, the thiol reactive unit reacts with an thiol group on an analyte molecule. In embodiments of the fourth aspect of the present invention, the thiole reactive unit is selected from the group consisting of haloacetyl group, in particular selected from the group consisting of Br/I-CH2-C(═O)— unit, acrylamide/ester unit, unsaturated imide unit such as maleimide, methylsulfonyl phenyloxadiazole and sulfonylchloride unit.

In embodiments of the fourth aspect of the present invention, the phenol reactive unit reacts with phenol groups on an analyte molecule. In embodiments of the fourth aspect of the present invention, the phenol-reactive unit is selected from the group consisting of active ester unit such as N-hydroxy succinimide (NHS) ester or sulfo-NHS ester, pentafluoro phenyl ester, carbonylimidazole ester, quadratic acid esters, a hydroxybenzotriazole (HOBt) ester, 1-hydroxy-7-azabenzotriazole (HOAt) ester, and a sulfonylchloride unit. Phenol groups present on an analyte molecule can be reacted with triazole dione via a reaction (H. Ban et al J. Am. Chem. Soc., 2010, 132 (5), pp 1523-1525) or by diazotization or alternatively by ortho nitration followed by reduction to an amine which could then be reacted with an amine reactive reagent.

In embodiments of the fourth aspect of the present invention, the reactive unit X is a epoxide reactive unit, which is capable of reacting with an analyte comprising a epoxide group. In embodiments of the fourth aspect of the present invention, the epoxide reactive unit is selected from the group consisting of amino, thiol, super-nucleophilic N atom strengthened by the a-effect through an adjacent O or N atom NH2-N/O molecule. In embodiments of the fourth aspect of the present invention, the epoxide reactive unit is selected from the group:

(i) a hydrazine unit, e.g. a $H_2N$—NH—, or $H_2N$—$NR^1$— unit, wherein $R^1$ is aryl, aryl containing 1 or more heteroatoms or Cia alkyl, particularly $C_1$ or $C_2$ alkyl, optionally substituted e.g. with halo, hydroxyl, and/or $C_{1-3}$ alkoxy, (ii) a hydrazide unit, in particular a carbo-hydrazide or sulfo-hydrazide unit, in particular a $H_2N$—NH—C(O)—, or $H_2N$—$NR^2$—C(O)— unit, wherein $R^2$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, and (iii) a hydroxylamino unit, e.g. a $H_2N$—O— unit.

In embodiments of the fourth aspect of the present invention, the reactive unit X is a disulfide reactive unit, which is capable of reacting with an analyte comprising a disulfide group. In embodiments of the fourth aspect of the present invention, the disulfide reactive unit is selected from the group consisting of thiol. In further embodiments, disulfide group can be reduced to the respective thiol group and then reacted with thiol reactive units X.

In embodiments of the fourth aspect of the present invention, the reactive unit X is a azido reactive unit which reacts with azido groups on an analyte molecule. In embodiments of the fourth aspect of the present invention, the azido-reactive unit reacts with azido groups through azide-alkyne cycloaddition. In embodiments of the fourth aspect of the present invention, the azido-reactive unit is selected from the group consisting of alkyne (alkyl or aryl), linear alkyne or cyclic alkyne. The reaction between the azido and the alkyne can proceed with or without the use of a catalyst. In further embodiments of the fourth aspect of the present invention the azido group can be reduced to the respective amino group and then reacted with amino reactive units X.

The compounds of formula A comprise a neutral loss unit Y. The neutral loss unit Y is able to loose a moiety (a neutral entity) having no charge. The neutral loss unit Y is capable of fragmentation, i.e. under conditions of MS, e.g. when subjected to collision-induced dissociation (CID), for example in triple quadrupole MS, whereby a neutral entity is released. The lost neutral entity is a single atom or a plurality of atoms. After release of the neutral entity, the remainder of neutral loss unit Y still remains neutral. Typically, but not necessarily, one neutral entity is released. In particular embodiments of the fourth aspect of the present invention, two neutral entity are released.

In embodiments of the fourth aspect of the present invention, the neutral loss unit Y releases at least one neutral entity upon ionization. The neutral entity is a low molecular weight neutral entity, in particular in a range of 10-100 Da, in particular 20-80 Da, in particular 25-65 Da. In particular, the neutral entity has a molecular weight of 100 Da or less, in particular of 80 Da or less, in particular of 70 Da or less, in particular of 50 Da or less, in particular of 30 Da or less.

In embodiments of the fourth aspect of the present invention, the neutral entity is selected from the group consisting of $N_2$, NO, $NO_2$, $S_2$, SO, $SO_2$, CO, $CO_2$. In particular embodiments, the neutral entity is $N_2$.

In embodiments of the fourth aspect of the present invention, the loss of the neutral entity leads to a reduction of the mass/charge ratio (m/z) by −28 Da (in case $N_2$ or CO is lost), −30 Da (in case NO is lost), −44 Da (in case $CO_2$ is lost), −46 Da (in case $NO_2$ is lost), −48 Da (in case SO is lost), −64 Da (in case $S_2$ or $SO_2$ is lost), or −87 Da (in case N2 and Trimethylamin are lost).

In embodiments of the fourth aspect of the present invention, one neutral entity is released. In embodiments of the fourth aspect of the present invention, two neutral entities are released. In particular, the second released neutral entity is different from the first released neutral entity. The release of the second neutral entity occurs concurrently or subsequently to the release of the first neutral entity. In particular, the release of the second neutral entity occurs concurrently to the release of the first neutral entity, i.e. both neutral entity are released at once, i.e in one single fragmentation event.

In embodiments of the fourth aspect of the present invention, the neutral loss unit Y comprises or consists of a cyclic moiety which is capable of fragmentation.

In embodiments of the fourth aspect of the present invention, the neutral loss unit Y comprises or consists of a 4-, 5- or 6-membered heterocyclic moiety, particularly a 4-, 5-, 6-membered heterocyclic moiety having at least 2 heteroatoms adjacent to each other, in particular two N atoms adjacent to each other. In embodiment of the fourth aspect of the present invention, the neutral loss unit Y comprises or consists of triazole, tetrazole, tetrazine, oxadiazole, thiadiazole moiety or a hydrogenated derivative thereof. In embodiments of the fourth aspect of the present invention, the neutral loss unit Y comprises or consists a 1,2,3-triazole, 1,2,4-triazole moiety, 1,4,5-triazole, 3,4,5-triazole moiety, a 1,2,3,4-tetrazole, 2,3,4,5-tetrazole or a 2,3,5,6 tetrazole moiety, or a 1,2,4,5 tetrazine moiety. In embodiments of the fourth aspect of the present invention, the neutral loss unit Y comprises or consists a 1,2,3-triazole or 1,2,4-triazol moiety, or a 1,2,3,4-tetrazole moiety, or a 1,2,4,5 tetrazine moiety.

In embodiments of the fourth aspect of the present invention, the charged unit Z is permanently charged, in particular under neutral conditions, in particular at a pH value of 6-8.

In embodiments of the fourth aspect of the present invention, the charged unit Z is positively or negatively charged, preferably positively charged.

In embodiments of the fourth aspect of the present invention, the charged unit Z comprises or consists of (i) at least one positively charged moiety.

or (ii) at least one negatively charged moiety.

In embodiments of the fourth aspect of the present invention, the charged unit Z is a positively charged unit. In embodiments of the fourth aspect of the present invention, the positively charged unit Z, is choosen in a manner that the resulting compound of formula A has a pKa of 10 or higher, more particularly has a pKa of 12 or higher. In embodiments of the fourth aspect of the present invention, the positively charged unit Z is selected from the group consisting of primary, secondary, tertiary or quaternary ammonium, sulfonium, imidazolium, pyridinium, or a phosphonium. In particular embodiments of the fourth aspect, the positively charged moiety is tri-methyl-ammonium, N,N-dimethyl-piperidinium or N-alkyl-quinuclidinium.

In embodiments of the fourth aspect of the present invention, the charged unit Z is a negatively charged unit. In embodiments of the fourth aspect of the present invention, the negatively charged unit Z is choosen in a manner that the resulting compound of formula A has a pKb of 10 or higher, more particularly has a pKb of 12 or higher. In embodiments of the fourth aspect of the present invention, the negatively charged unit Z is selected from the group consisting of a phosphate, sulphate, sulphonate or carboxylate.

In embodiments of the fourth aspect of the present invention, the linker L1 and L2 are independently of each other linear linker. In embodiments of the fourth aspect, the linear linker L1 and L2 are independently of each other a single bond between two functional units of the compound of formula A, or comprise 1 to 10 C-atoms, in particular 1 to 6 C-atoms, in particular 1, 2, or 3 C-atoms. In embodiments of the fourth aspect, the linear linker L1 and L2 comprises independently of each other 1 or more heteroatoms, in particular N, O or S. In embodiments of the fourth aspect of the present invention, the linker L1 and L2 are independently of each other substituted or unsubstituted, in particular the linker L1 and L2 are unsubstituted. In embodiments of the fourth aspect of the present invention, the linker L1 and/or L2 is not protonatable. In embodiments of the fourth aspect of the present invention, the linear linker L1 and/or L2 comprises a stabilizing unit. In embodiments of the fourth aspect of the present invention, the stabilizing unit prevents the loss of the charged unit Z during the fragmentation event. In embodiments of the fourth aspect of the present invention, the stabilizing unit prevents the loss of the charged unit Z by destabilizing the potentially formed carbokation. In embodiments of the fourth aspect of the present invention, the stabilising unit is separated by one C atom from the charged unit Z. In embodiments of the fourth aspect of the present invention, the stabilising unit comprises at least one heteroatom. In embodiments of the fourth aspect of the present invention, the stabilising unit is selected from the group consisting of CO, or isoelectrical analogons thereof such as SO or SO2. In embodiments of the fourth aspect, the linear linker L1 is a single bond connecting the reactive unit and the neutral loss unit, and the linker L2 is 1 or 2 C-atoms, optionally comprising one or two heteroatoms, in particular 1 or 2 O-atoms, connecting the neutral loss unit and the positively charged unit of the compound of formula A. In embodiments of the fourth aspect, the linear linker L1 comprises 1 C-atom connecting the reactive unit and the neutral loss unit, and the linker L2 comprises 1 or 2 C-atoms and 1 O-atom connecting the neutral loss unit and the positively charged unit of the compound of formula A. In embodiments of the fourth aspect, the linear linker L1 comprises 3 C-atoms and one O-atom connecting the reactive unit and the neutral loss unit, and the linker L2 comprises 1 C-atom and 1 O-atom connecting the neutral loss unit and the positively charged unit of the compound of formula A. In embodiments of the fourth aspect, the linear linker L1 comprises 6 C-atoms and one O-atom connecting the reactive unit and the neutral loss unit, and the linker L2 comprises 2 C-atoms and 1 O-atom connecting the neutral loss unit and the positively charged unit of the compound of formula A. In embodiments of the fourth aspect, the linear linker L1 comprises 7 C-atoms and 1 O-atom connecting the reactive unit and the neutral loss unit, and the linker L2 is a single bond connecting the neutral loss unit and the positively charged unit of the compound of formula A.

In embodiments of the fourth aspect of the present invention, the compound has a structure of formula A, wherein the reactive unit X is a carbonyl-reactive unit, neutral loss unit Y is a 5-membered heterocyclic unit, and the charged unit Z is a permanently positively charged unit.

In embodiments of the fourth aspect of the present invention, the adduct has a structure of formula A', wherein X' results from the reaction of a diene reactive unit X with an analyte molecule T, the neutral loss unit Y is a 5-membered heterocyclic unit, and the charged unit Z is a permanently positively charged unit.

In embodiments of the fourth aspect of the present invention, the adduct has a structure of formula A', wherein X' results from the reaction of a hydrazine unit X with an analyte molecule T, the neutral loss unit Y is a 5-membered heterocyclic moiety comprising at least 3 heteroatoms, and the charged unit Z is a tertiary ammonium group.

In embodiments of the fourth aspect of the present invention, the adduct has a structure of formula A', wherein X' results from the reaction of a hydrazide unit X with an analyte molecule T, the neutral loss unit Y is a 5-membered heterocyclic unit comprising at least 3 heteroatoms, and the charged unit Z is a tertiary ammonium group.

In embodiments of the fourth aspect of the present invention, the adduct has a structure of formula A', wherein X' results from the reaction of a hydrazine unit X with an analyte molecule T, the neutral loss unit Y is a 5-membered heterocyclic moiety comprising at least 3 heteroatoms, and the charged unit Z is a piperidine unit.

In embodiments of the fourth aspect of the present invention, the adduct has a structure of formula A', wherein X' results from the reaction of a hydrazide unit X with an analyte molecule T, the neutral loss unit Y is a 5-membered heterocyclic unit comprising at least 3 heteroatoms, and the charged unit Z is a piperidine unit.

In embodiments of the fourth aspect of the present invention, the adduct has a structure of formula A', wherein X' results from the reaction of a hydrazine unit X with an analyte molecule T, the neutral loss unit Y is a 5-membered heterocyclic moiety comprising at least 3 heteroatoms, and the charged unit Z is a pyridine unit.

In embodiments of the fourth aspect of the present invention, the adduct has a structure of formula A', wherein X' results from the reaction of a hydrazone unit X with an analyte molecule T, the neutral loss unit Y is a 5-membered heterocyclic unit comprising at least 3 heteroatoms, and the charged unit Z is a pyridine unit.

In embodiments of the fourth aspect of the present invention, the adduct has a structure of formula A', wherein X' results from the reaction of a Cookson-type reagent with an analyte molecule T, the neutral loss unit Y is a 5-membered heterocyclic unit comprising at least 3 heteroatoms, and the charged unit Z is a tertiary ammonium group.

In embodiments of the fourth aspect of the present invention, the adduct has a structure of formula A', wherein X' results from the reaction of a Cookson-type reagent with an analyte molecule T, the neutral loss unit Y is a 5-membered heterocyclic unit comprising at least 3 heteroatoms, and the charged unit Z is a piperidine unit.

In embodiments of the fourth aspect of the present invention, the adduct has a structure of formula A', wherein X' results from the reaction of a Cookson-type reagent with an analyte molecule T, the neutral loss unit Y is a 5-membered heterocyclic unit comprising at least 3 heteroatoms, and the charged unit Z is a pyridine unit.

In embodiments of the fourth aspect of the present invention, the adduct has a structure of formula A', wherein X' results from the reaction of $H_2N$—NH— with an analyte molecule T, the neutral loss unit Y is 1,2,3-triazole, 2,3,4,5-tetrazole, or 2,3,5,6 tetrazole, and the charged unit Z is a tertiary ammonium unit.

In embodiments of the fourth aspect of the present invention, the adduct has a structure of formula A', wherein X' results from the reaction of $H_2N$—NH— with an analyte molecule T, the neutral loss unit Y is 1,2,3-triazole, 1,2,4-triazol, 1,2,3,4-tetrazole, or 1,2,4,5-tetrazine, and the charged unit Z is a piperidine unit.

In embodiments of the fourth aspect of the present invention, the adduct has a structure of formula A', wherein X' results from the reaction of $H_2N$—NH— with an analyte molecule T, the neutral loss unit Y is 1,2,3-triazole, 1,2,4-triazol, 1,2,3,4-tetrazole, or 1,2,4,5-tetrazine, and the charged unit Z is a pyridine unit.

In embodiments of the fourth aspect of the present invention, the adduct has a structure of formula A', wherein X' results from the reaction of $H_2N$—O—C— with an analyte molecule T, the neutral loss unit Y is 1,2,3-triazole, 1,2,4-triazol, 1,2,3,4-tetrazole, or 1,2,4,5-tetrazine, and the charged unit Z is a dimethyl-piperidine or quinuclidine unit.

In embodiments of the fourth aspect of the present invention, the adduct has a structure of formula A', wherein X' results from the reaction of 1,2,4-triazolin-3,5-dione with an analyte molecule T, the neutral loss unit Y is 1,2,3-triazole, 2,3,4,5-tetrazole, or 2,3,5,6, and the charged unit Z is a dimethyl-piperidine or quinuclidine moiety.

In embodiments, the adduct of formula A' is selected from the group consisting of (i) Adduct 1

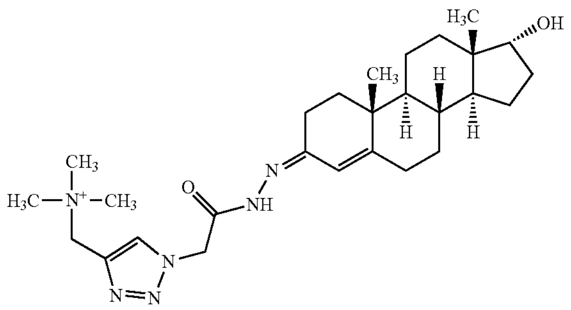

-continued (ii) Adduct 2

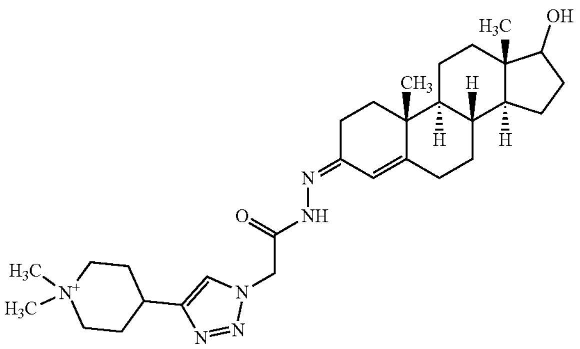

(iii) Adduct 3

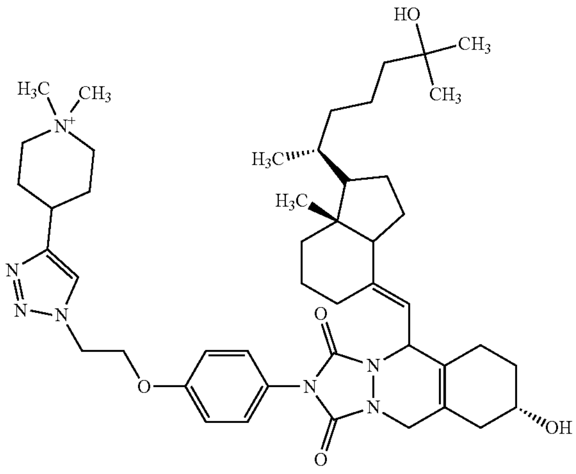

In a fifth aspect, the present invention relates to the use of a compound of formula A:

X-L1-Y-L2-Z wherein

X is a reactive unit,

L1 and L2 are independently of each other substituted or unsubstituted linker, in particular linear linker, Y is a neutral loss unit, Z is a charged unit comprising at least one permanently charged moiety, in particular one permanently charged moiety, including any salt thereof, or of a composition or kit comprising at least one compound of formula A, for the mass spectrometric determination of an analyte molecule, wherein the mass spectrometric determination particularly comprises a tandem mass spectrometric determination, more particularly in a triple quadrupole device.

In embodiments of the fifth aspect of the present invention, the use of a compound of formula A comprises the use as a derivatization reagent. In embodiments of the fifth aspect of the present invention, the compound of formula A is used to increase the sensitivity of MS measurement. In embodiments, the compound of formula A is used to detect the analyte of interest at a lower level of detection, in particular at a lower level of quantification.

In embodiments of the fifth aspect of the present invention, the compound of formula A according to the present invention comprises a reactive unit X which is capable of reacting with an analyte molecule. The reactive unit X is capable of reacting with an analyte molecule such that a covalent bond between the compound of formula A and the analyte molecule is formed. In embodiments of the fifth aspect of the present invention, the reactive unit X forms a covalent bond with the compound of formula A. In particular, the covalent bond is formed between the reactive unit X of compound of formula A and a functional group present in the analyte molecule.

Depending on the functional groups present in the analyte molecule to be determined, the skilled person will select an appropriate reactive unit X for compound of formula A. It is within common knowledge to decide which reactive unit X will qualify for binding to a functional group of an analyte of interest.

In embodiments of the fifth aspect of the present invention, the analyte molecule comprises a functional group selected from the group consisting of carbonyl group, diene group, hydroxyl group, amine group, imine group, thiol group, diol group, phenolic group, expoxid group, disulfide group, and azide group, each of which is capable of forming a covalent bond with reactive unit X of compound of formula A.

Further, it is also contemplated within the scope of the present invention that a functional group present on an analyte molecule would be first converted into another group that is more readily available for reaction with reactive unit X of compounds of formula A.

In embodiments of the fifth aspect of the present invention, the analyte molecule is selected from the group consisting of steroids, ketosteroids, secosteroids, amino acids, peptides, proteins, carbohydrates, fatty acids, lipids, nucleosides, nucleotides, nucleic acids and other biomolecules including small molecule metabolites and cofactors as well as therapeutic drugs, drugs of abuse, toxins or metabolites thereof.

In embodiments of the fifth aspect of the present invention, the analyte molecule comprises a carbonyl group as functional group which is selected from the group consisting of a carboxylic acid group, aldehyde group, keto group, a masked aldehyde, masked keto group, ester group, amide group, and anhydride group.

In embodiments of the fifth aspect of the present invention, wherein the carbonyl group is an amide group, the skilled person is well-aware that the amide group as such is a stable group, but that it can be hydrolized to convert the amide group into an carboxylic acid group and an amino group. Hydrolysis of the amide group may be achieved via acid/base catalysed reaction or by enzymatic process either of which is well-known to the skilled person. In embodiments of the fifth aspect of the present invention, wherein the carbonyl group is a masked aldehyde group or a masked keto group, the respective group is either a hemiacetal group or acetal group, in particular a cyclic hemiacetal group or acetal group. In embodiments of the fifth aspect of the present invention, the acetal group, is converted into an aldehyde or keto group before reaction with the compound of formula A.

In embodiments of the fifth aspect of the present invention, the carbonyl group is a keto group. In embodiments of the fifth aspect of the present invention, the keto group may be transferred into an intermediate imine group before reacting with the reactive unit of compounds of formula A. In embodiments of the fifth aspect of the present invention, the analyte molecule comprising one or more keto groups is a ketosteroid. In particular embodiments of the fifth aspect of the present invention, the ketosteroid is selected from the group consisting of testosterone, epitestosterone, dihydrotestosterone (DHT), desoxymethyltestosterone (DMT), tetrahydrogestrinone (THG), aldosterone, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17-OH pregnenolone, 17-OH progesterone, 17-OH progesterone, androsterone, epiandrosterone, and delta 4 androstenedione) 11-desoxycortisol corticosterone, 21-deoxycortisol, 11-deoxycorticosterone, allopregnanolone, and aldosterone.

In embodiments of the fifth aspect of the present invention, the carbonyl group is a carboxyl group. In embodiments of the fifth aspect of the present invention, the carboxyl group reacts directly with the compound of formula A or it is converted into an activated ester group before reaction with the compound of formula A. In embodiments of the fifth aspect of the present invention, the analyte molecule comprising one or more carboxyl groups is selected from the group consisting of Δ8-Tetrahydrocannabinol-acid, Benzoylecgonin, Salicylic acid, 2-hydroxybenzoic acid, Gabapentin, Pregabalin, Valproic acid, Vancomycin, Methotrexat, Mycophenolic acid, Montelukast, Repaglinide, Furosemide, Telmisartan, Gemfibrozil, Diclorofenac, Ibuprofen, Indomethacin, Zomepirac, Isoxepac, and Penicilin. In embodiments of the fifth aspect of the present invention, the analyte molecule comprising one or more carboxyl groups is an amino acid selected from the group consisting of arginine, lysine, aspartic acid, glutamic acid, glutamine, asparagine, histidine, serine, threonine, tyrosine, cysteine, tryptophan, alanine, isoleucine, leucine, methionine, phenyalanine, valine, proline, and glycine.

In embodiments of the fifth aspect of the present invention, the carbonyl group is an aldehyde group. In embodiments of the fifth aspect of the present invention, the aldehyde group may be transferred into an intermediate imine group before reacting with the reactive unit of compounds of formula A. In embodiments of the fifth aspect of the present invention, the analyte molecule comprising one or more aldehyde groups is selected from the group consisting of Pyridoxal, N-Acetyl-D-glucosamine, Alcaftadine, Streptomycin, Josamycin.

In embodiments of the fifth aspect of the present invention, the carbonyl group is an carbonyl ester group. In embodiments of the fifth aspect of the present invention, the analyte molecule comprising one or more ester groups is selected from the group consisting of Cocaine, Heroin, Ritalin, Aceclofenac, Acetycholine, Amcinonide, Amiloxate, amylocaine, Anileridine, Aranidipine, and Artesunate, Pethidine.

In embodiments of the fifth aspect of the present invention, the carbonyl group is an anhydride group. In embodiments of the fifth aspect of the present invention, the analyte molecule comprising one or more anhydride groups is selected from the group consisting of Cantharidin, Succinic Anhydride, Trimellitic Anhydride, and Maleic Anhydride.

In embodiments of the fifth aspect of the present invention, the analyte molecule comprises one or more diene groups, in particular to conjugated diene groups, as functional group. In embodiments of the fifth aspect of the present invention, the analyte molecule comprising one or more diene groups is a secosteroid. In embodiments, the secosteroid is selected from the group consisting of Cholecalciferol (Vitamin D3), Ergocalciferol (Vitamin D2), Calcidiol, Calcitriol, Tachysterol, Lumisterol und Tacalcitol. In particular, the secosteroid is Vitamin D, in particular Vitamin D2 or D3 or derivates thereof. In particular embodiments, the secosteroid is selected from the group consisting of Vitamin D2, Vitamin D3, 25-Hydroxy Vitamin D2, 25-Hydroxy Vitamin D3, 3-Epi-25-Hydroxy Vitamin D2, 3-Epi-25-Hydroxy Vitamin D3, 1,25-Dihydroxy Vitamin D2, 1,25-Dihydroxy Vitamin D3, 24,25-Dihydroxy Vitamin D2, and 24,25-Dihydroxy Vitamin D3, Vitamin A, Tretinoin, Isotretinoin, Alitretinoin, Natamycin, Sirolimus, Amphotericin B, Nystatin, Everolimus, Temsirolimus, Fidaxomicin.

In embodiments of the fifth aspect of the present invention, the analyte molecule comprises one or more hydroxyl group as functional group. In embodiments of the fifth aspect of the present invention, the analyte molecule comprises a single hydroxyl group or two hydroxyl groups. In embodiments wherein more than one hydroxyl group is present, the two hydroxyl groups may be positioned adjacent to each other (1,2 diol) or may be separated by 1, 2, or 3 C-atoms (1,3-diol, 1,4-diol, 1,5-diol, respectively). In particular embodiments of the fifth aspect, the analyte molecule comprises an 1,2 diol group. In embodiments, wherein only one hydroxyl group is present, said analyte is selected from the group consisting of primary alcohol, secondary alcohol and tertiary alcohol. In embodiments of the fifth aspect of the present invention, wherein the analyte molecule comprises one or more hydroxyl groups, the analyte is selected from the group consisting of Benzyl alcohol, Menthol, L-Carnitine, Pyridoxine, Metronidazole, Isosorbide mononitrate, Guaifenesin, Clavulanate, Migitol, Zalcitabine, Isoprenaline, Aciclovir, Methocarbamol, Tramadol, Venlafaxine, Atropine, Clofedanol, alpha-Hydroxyalprazolam, Alpha-Hydroxytriazolam, Lorazepam, Oxazepam, Tamazepam, Ethylglucuronide, Ethylmorphine, Morphine, Morphine-3-glucuronide, Buprenorphine, Codeine, Dihydrocodeine, p-Hydroxypropoxyphene, 0-desmethyltramadol, Dihydroquinidine, Quinidine. In embodiments of the fifth aspect of the present invention, wherein the analyte molecule comprises more than one hydroxyl groups, the analyte is selected from the group consisting of Vitamin C, Glucosamine, Mannitol, Tetrahydrobiopterin, Cytarabine, Azacitidine, Ribavirin, Floxuridine, Gemcitadine, Streptozocin, Adenosine, Vibarabine, Cladribine, Estriol, Trifluridine, Clofarabine, Nadolol, Zanamivir, Lactulose, Adenosine monophosphate, Idoxuridine, Regadenoson, Lincomycin, Clindamycin, Canaglifozin, Tobramycin, Netilmicin, Kanamycin, Ticagrelor, Epirubicin, Doxorubicin, Arbekacin, Steptomycin, Quabain, Amikacin, Neomycin, Framycetin, Paromomycin, Erythromycin, Clarithromycin, Azithromycin, Vindesine, Digitoxin, Digoxin, Metrizamide, Acetyldigitoxin, Deslanoside, Fludaradine, Clofarabine, Gemcitabine, Cytarabine, Capecitabine, Vidarabine, Trifluridine, Idoxuridine, and Plicamycin.

In embodiments of the fifth aspect of the present invention, the analyte molecule comprises one or more thiol group (including but not limited to alkyl-thiol and thiol-ary groups) as functional group. In embodiments of the fifth aspect of the present invention, the analyte molecule comprising one or more thiol groups is selected from the group consisting of Thiomandelic acid, DL-Captopril, DL-Thiorphan, N-Acetylcysteine, D-Penicillamine, Glutathione, L-Cysteine, Zefenoprilat, Tiopronin, Dimercaprol, Succimer.

In embodiments of the fifth aspect of the present invention, the analyte molecule comprises one or more disulfide group as functional group. In embodiments of the fifth aspect of the present invention, the analyte molecule comprising one or more disulfide groups is selected from the group consisting of Glutathione Disulfide, Dipyrithione, Selenium Sulfide, Disulfiram, Lipoic Acid, L-Cystine, Fursultiamine, Octreotide, Desmopressin, Vapreotide, Terlipressin, Linaclotide, Peginesatide.

In embodiments of the fifth aspect of the present invention, the analyte molecule comprises one or more epoxide group as functional group. In embodiments of the fifth aspect of the present invention, the analyte molecule comprising one or more epoxide groups is selected from the group consisting of Carbamazepine 10,11 epoxide, Carfilzomib, Furosemide epoxide, and Fosfomycin, Sevelamer, Cerulenin, Scopolamine, Tiotropium, Methylscopolamine bromide, Eplerenone, Mupirocin, Natamycin, Carfilzomib, Troleandomycin.

In embodiments of the fifth aspect of the present invention, the analyte molecule comprises one or more phenol groups as functional group. In particular embodiments of the fifth aspect of the present invention, analyte molecules comprising one or more phenol groups are steroids or steroid-like compounds. In embodiments of the fifth aspect of the present invention, the analyte molecule comprising one or more phenol groups is a steroid or a steroid-like compound having an A-ring which is $sp^2$ hybridized and an OH group at the 3-position of the A-ring. In particular embodiments of the fifth aspect of the present invention, the steroid or steroid-like analyte molecule is selected from the group consisting of estrogen, estrogen-like compounds, estrone (E1), estradiol (E2), 17a-estradiol, 17p-estradiol, estriol (E3), 16-epiestriol, 17-epiestriol, and 16, 17-epiestriol, and/or metabolites thereof. In embodiments, the metabolites is selected from the group consisting of estriol, 16-epiestriol (16-epiE3), 17-epiestriol (17-epiE3), 16,17-epiestriol (16,17-epiE3), 16-ketoestradiol (16-ketoE2), 16a-hydroxyestrone (16a-OHEl), 2-methoxyestrone (2-MeOEI), 4-methoxyestrone (4-MeOEl), 2-hydroxyestrone-3-methyl ether (3-MeOEl), 2-methoxyestradiol (2-MeOE2), 4-methoxyestradiol (4-MeOE2), 2-hydroxyestrone (20HE1), 4-hydroxyestrone (4-OHE1), 2-hydroxyestradiol (2-OHE2), estrone (E1), estrone sulfate (Els), 17a-estradiol (E2a), 17p-estradiol (E2b), estradiol sulfate (E2s), equilin (EQ), 17a-dihydroequilin (EQa), 17p-dihydroequilin (EQb), Eqilenin (EN), 17-dihydroequilenin (ENa) 17p-dihydroequilenin (ENb), A8,9-dehydroestrone (dEl), A8,9-dehydroestrone sulfate (dEls), A9-Tetrahydrocannabinol, Mycophenolic acid.

In embodiments of the fifth aspect of the present invention, the analyte molecule comprises an amine group as functional group. In embodiments of the fifth aspect of the present invention, the amine group is an alkyl-amine or an aryl-amine group. In embodiments of the fifth aspect of the present invention, the analyte comprising one or more amine groups is selected from the group consisting of proteins and peptides.

In embodiments of the fifth aspect of the present invention, the analyte molecule comprising an amine group is selected from the group consisting of 3,4-Methylendioxyamphetamin, 3,4-Methylendioxy-N-ethylamphetamin, 3,4-Methylenedioxymethamphetamine, Amphetamin, Methamphetamin, N-methyl-1,3-benzodioxolylbutanamine, 7-Aminoclonazepam, 7-aminoflunitrazepam, 3,4-Dimethylmethcathinone, 3-Fluoromethcathinone, 4-Methoxymethcathinone, 4-Methylethcathinone, 4-Methylmethcathinone, Amfepramone, Butylone, Ethcathinone, Flephedrone, Methcathinone, Methylone, Methylendioxypyrovaleron, Benzoylecgonine, Dehydronorketamine, Ketamine, Norketamine, Methadone, Normethadone, 6-Acetylmorphine, Diacetylmorphine, Morphine, Norhydrocodone, Oxycodone, Oxymorphone, Phencyclidine, Norpropoxyphene, Amitriptyline, Clomipramine, Dothiepin, Doxepin, Imipramine, Nortriptyline, Trimipramine, Fentanyl, Glycylxylidide, Lidocaine, Monoethylglycylxylidide, N-Acetyl Procainamide, Procainamide, Pregabalin, 2-Methylamino-1-(3,4-methylendioxyphenyl)butan, 2-Amino-1-(3,4-methylendioxyphenyl)butan, Normeperidine, 0-Destramadol, Tramadol, Lidocaine, N-Acetyl Procainamide, Procainamide, Gabapentin, Lamotrigine, Theophyllin, Amikacin, Gentamicin, Tobramycin, Vancomycin, Methotrexat, Gabapentin, Sisomicin, and 5-Methylcytosine.

In embodiments of the fifth aspect of the present invention, the analyte molecule is a carbohydrate or substance having a carbohydrate moiety, e.g. a glycoprotein or a nucleoside. In embodiments of the fifth aspect of the present invention, the analyte molecule is a monosaccharide, in particular selected from the group consisting of ribose, desoxyribose, arabinose, ribulose, glucose, mannose, galactose, fucose, fructose, N-acetylglucosamine, N-acetylgalactosamine, neuraminic acid, N-acetylneurominic acid, etc. In embodiments, the analyte molecule is an oligosaccharide, in particular selected from the group consisting of a disaccharide, trisaccharid, tetrasaccharide, polysaccharide. In embodiments of the fifth aspect of the present invention, the disaccharide is selected from the group consisting of sucrose, maltose and lactose. In embodiments of the fifth aspect of the present invention, the analyte molecule is a substance comprising above described mono-, di-, tri-, tetra-, oligo- or polysaccharide moiety.

In embodiments of the fifth aspect of the present invention, the analyte molecule comprises an azide group as functional group which is selected from the group consisting of alkyl or aryl azide. In embodiments of the fifth aspect of the present invention, the analyte molecule comprising one or more azide groups is selected from the group consisting of Zidovudine and Azidocillin.

Such analyte molecules may be present in biological or clinical samples such as body liquids, e.g. blood, serum, plasma, urine, saliva, spinal fluid, etc., tissue or cell extracts, etc. In embodiments of the fifth aspect of the present invention, the analyte molecule(s) are present in a biological or clinical sample selected from the group consisting of blood, serum, plasma, urine, saliva, spinal fluid, and a dried blood spot. In some embodiments of the fifth aspect of the present invention, the analyte molecules may be present in a sample which is a purified or partially purified sample, e.g. a purified or partially purified protein mixture or extract.

In embodiments of the fifth aspect of the present invention, the reactive unit X is selected from the group consisting of carbonyl reactive unit, diene reactive unit, hydroxyl reactive unit, amino reactive unit, an imine reactive unit, a thiol reactive unit, a diol reactive unit, a phenol reactive unit, epoxide reactive unit, a disulfide reactive unit, and a azido reactive unit.

In embodiments of the fifth aspect of the present invention, the reactive unit X is a carbonyl reactive unit, which is capable of reacting with any type of molecule having a carbonyl group. In embodiments of the fifth aspect of the present invention, the carbonyl reactive unit is selected from the group consisting of carboxyl reactive unit, keto reactive unit, aldehyde reactive unit, anhydride reactive unit, carbonyl ester reactive unit, and imide reactive unit. In embodiments of the fifth aspect of the present invention, the carbonyl-reactive unit may have either a super-nucleophilic N atom strengthened by the α-effect through an adjacent O or N atom NH2-N/O or a dithiol molecule. In embodiments of the fifth aspect of the present invention, the carbonyl-reactive unit is selected from the group:

(i) a hydrazine unit, e.g. a $H_2N$—NH—, or $H_2N$—$NR^1$— unit, wherein $R^1$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, (ii) a hydrazide unit, in particular a carbo-hydrazide or sulfo-hydrazide unit, in particular a $H_2N$—NH—C(O)—, or $H_2N$—$NR^2$—C(O)— unit, wherein $R^2$ is aryl, aryl containing 1 or more heteroatoms or Cia alkyl, particularly $C_1$ or $C_2$ alkyl, optionally substituted e.g. with halo, hydroxyl, and/or $C_{1-3}$ alkoxy, (iii) a hydroxylamino unit, e.g. a $H_2N$—O— unit, and (iv) a dithiol unit, particularly a 1,2-dithiol or 1,3-dithiol unit.

In embodiments of the fifth aspect of the present invention, wherein the carbonyl reactive unit is a carboxyl reactive unit, the carboxyl reactive units reacts with carboxyl groups on an analyte molecule. In embodiment of the fifth aspect of the present invention, the carboxyl reactive unit is selected from the group consisting of a diazo unit, an alkylhalide, amine, and hydrazine unit.

In embodiments of the fifth aspect of the present invention, the reactive unit X is a diene reactive unit, which is capable of reacting with an analyte comprising a diene group. In embodiments of the fifth aspect of the present invention, the diene reactive unit is selected from the group consisting of Cookson-type reagents, e.g. 1,2,4-triazolin-3,5-diones, which are capable to act as a dienophile.

In embodiments of the fifth aspect of the present invention, the reactive unit X is a hydroxyl reactive unit, which is capable of reacting with an analyte comprising a hydroxyl group. In embodiments of the fifth aspect of the present invention, the hydroxyl reactive units is selected from the group consisting of sulfonylchlorides, activated carboxylic esters (NHS, or imidazolide), and fluoro aromates/heteroaromates capable for nucleophilic substitution of the fluorine (T. Higashi J Steroid Biochem Mol Biol. 2016 September; 162:57-69). In embodiments of the fifth aspect of the present invention, the reactive unit X is a diol reactive unit which reacts with an diol group on an analyte molecule. In embodiments of the fifth aspect of the present invention, wherein the reactive unit is a 1,2 diol reactive unit, the 1,2 diol reactive unit comprises boronic acid. In further embodiments, diols can be oxidised to the respective ketones or aldehydes and then reacted with ketone/aldehyde-reactive units X.

In embodiments of the fifth aspect of the present invention, the amino reactive unit reacts with amino groups on an analyte molecule. In embodiments of the fifth aspect of the present invention, the amino-reactive unit is selected from the group consisting of active ester group such as N-hydroxy succinimide (NHS) ester or sulfo-NHS ester, pentafluoro phenyl ester, cabonylimidazole ester, quadratic acid esters, a hydroxybenzotriazole (HOBt) ester, 1-hydroxy-7-azabenzotriazole (HOAt) ester, and a sulfonylchloride unit.

In embodiments of the fifth aspect of the present invention, the thiol reactive unit reacts with an thiol group on an analyte molecule. In embodiments of the fifth aspect of the present invention, the thiole reactive unit is selected from the group consisting of haloacetyl group, in particular selected from the group consisting of Br/I-CH2-C(═O)— unit, acrylamide/ester unit, unsaturated imide unit such as maleimide, methylsulfonyl phenyloxadiazole and sulfonylchloride unit.

In embodiments of the fifth aspect of the present invention, the phenol reactive unit reacts with phenol groups on an analyte molecule. In embodiments of the fifth aspect of the present invention, the phenol-reactive unit is selected from the group consisting of active ester unit such as N-hydroxy succinimide (NHS) ester or sulfo-NHS ester, pentafluoro phenyl ester, carbonylimidazole ester, quadratic acid esters, a hydroxybenzotriazole (HOBt) ester, 1-hydroxy-7-azabenzotriazole (HOAt) ester, and a sulfonylchloride unit. Phenol groups present on an analyte molecule can be reacted with triazole dione via a reaction (H. Ban et al J. Am. Chem. Soc., 2010, 132 (5), pp 1523-1525) or by diazotization or alternatively by ortho nitration followed by reduction to an amine which could then be reacted with an amine reactive reagent.

In embodiments of the fifth aspect of the present invention, the reactive unit X is a epoxide reactive unit, which is capable of reacting with an analyte comprising a epoxide group. In embodiments of the fifth aspect of the present invention, the epoxide reactive unit is selected from the group consisting of amino, thiol, super-nucleophilic N atom strengthened by the α-effect through an adjacent O or N atom NH2-N/O molecule. In embodiments of the fifth aspect of the present invention, the epoxide reactive unit is selected from the group:

(i) a hydrazine unit, e.g. a $H_2N$—NH—, or $H_2N$—$NR^1$— unit, wherein $R^1$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, (ii) a hydrazide unit, in particular a carbo-hydrazide or sulfo-hydrazide unit, in particular a $H_2N$—NH—C(O)—, or $H_2N$—$NR^2$—C(O)— unit, wherein $R^2$ is aryl, aryl containing 1 or more heteroatoms or $C_{1-4}$ alkyl, particularly $C_1$ or $C_2$ alkyl, optionally substituted e.g. with halo, hydroxyl, and/or $C_{1-3}$ alkoxy, and (iii) a hydroxylamino unit, e.g. a $H_2N$—O— unit.

In embodiments of the fifth aspect of the present invention, the reactive unit X is a disulfide reactive unit, which is capable of reacting with an analyte comprising a disulfide group. In embodiments of the fifth aspect of the present invention, the disulfide reactive unit is selected from the group consisting of thiol. In further embodiments, disulfide group can be reduced to the respective thiol group and then reacted with thiol reactive units X.

In embodiments of the fifth aspect of the present invention, the reactive unit X is a azido reactive unit which reacts with azido groups on an analyte molecule. In embodiments of the fifth aspect of the present invention, the azido-reactive unit reacts with azido groups through azide-alkyne cycloaddition. In embodiments of the fifth aspect of the present invention, the azido-reactive unit is selected from the group consisting of alkyne (alkyl or aryl), linear alkyne or cyclic alkyne. The reaction between the azido and the alkyne can proceed with or without the use of a catalyst. In further embodiments of the fifth aspect of the present invention the azido group can be reduced to the respective amino group and then reacted with amino reactive units X.

The compounds of formula A comprise a neutral loss unit Y. The neutral loss unit Y is able to loose a moiety (a neutral entity) having no charge. The neutral loss unit Y is capable of fragmentation, i.e. under conditions of MS, e.g. when subjected to collision-induced dissociation (CID), for example in triple quadrupole MS, whereby a neutral entity is released. The lost neutral entity is a single atom or a plurality of atoms. After release of the neutral entity, the remainder of neutral loss unit Y still remains neutral. Typically, but not necessarily, one neutral entity is released. In particular embodiments of the fifth aspect of the present invention, two neutral entity are released.

In embodiments of the first aspect of the present invention, the neutral loss unit Y releases at least one neutral entity upon ionization. The neutral entity is a low molecular weight neutral entity, in particular in a range of 10-100 Da, in particular 20-80 Da, in particular 25-65 Da. In particular, the neutral entity has a molecular weight of 100 Da or less, in particular of 80 Da or less, in particular of 70 Da or less, in particular of 50 Da or less, in particular of 30 Da or less.

In embodiments of the first aspect of the present invention, the neutral entity is selected from the group consisting of $N_2$, NO, $NO_2$, $S_2$, SO, $SO_2$, CO, $CO_2$. In particular embodiments, the neutral entity is $N_2$.

In embodiments of the first aspect of the present invention, the loss of the neutral entity leads to a reduction of the mass/charge ratio (m/z) by −28 Da (in case $N_2$ or CO is lost), −30 Da (in case NO is lost), −44 Da (in case $CO_2$ is lost), −46 Da (in case $NO_2$ is lost), −48 Da (in case SO is lost), −64 Da (in case $S_2$ or $SO_2$ is lost), or −87 Da (in case N2 and Trimethylamin are lost).

In embodiments of the fifth aspect of the present invention, one neutral entity is released. In embodiments of the fifth aspect of the present invention, two neutral entities are released. In particular, the second released neutral entity is different from the first released neutral entity. The release of the second neutral entity occurs concurrently or subsequently to the release of the first neutral entity. In particular, the release of the second neutral entity occurs concurrently to the release of the first neutral entity, i.e. both neutral entity are released at once, i.e in one single fragmentation event.

In embodiments of the fifth aspect of the present invention, the neutral loss unit Y comprises or consists of a cyclic moiety which is capable of fragmentation. In embodiments of the fifth aspect of the present invention, the neutral loss unit Y comprises or consists of a 4-, 5- or 6-membered heterocyclic moiety, particularly a 4-, 5-, 6-membered heterocyclic moiety having at least 2 heteroatoms adjacent to each other, in particular two N atoms adjacent to each other. In embodiment of the fifth aspect of the present invention, the neutral loss unit Y comprises or consists of triazole, tetrazole, tetrazine, oxadiazole, thiadiazole moiety or a hydrogenated derivative thereof. In embodiments of the fifth aspect of the present invention, the neutral loss unit Y comprises or consists a 1,2,3-triazole, 1,2,4-triazole moiety, 1,4,5-triazole, 3,4,5-triazole moiety, a 1,2,3,4-tetrazole, 2,3,4,5-tetrazole or a 2,3,5,6 tetrazole moiety, or a 1,2,4,5 tetrazine moiety. In embodiments of the fifth aspect of the present invention, the neutral loss unit Y comprises or consists a 1,2,3-triazole or 1,2,4-triazol moiety, or a 1,2,3,4-tetrazole moiety, or a 1,2,4,5 tetrazine moiety.

In embodiments of the fifth aspect of the present invention, the charged unit Z is permanently charged, in particular under neutral conditions, in particular at a pH value of 6-8.

In embodiments of the fifth aspect of the present invention, the charged unit Z is positively or negatively charged, preferably positively charged.

In embodiments of the fifth aspect of the present invention, the charged unit Z comprises or consists of (i) at least one positively charged moiety.

or (ii) at least one negatively charged moiety.

In embodiments of the fifth aspect of the present invention, the charged unit Z is a positively charged unit. In embodiments of the fifth aspect of the present invention, the positively charged unit Z, is choosen in a manner that the resulting compound of formula A has a pKa of 10 or higher, more particularly has a pKa of 12 or higher. In embodiments of the fifth aspect of the present invention, the positively charged unit Z is selected from the group consisting of primary, secondary, tertiary or quaternary ammonium, sulfonium, imidazolium, pyridinium, or a phosphonium. In particular embodiments of the fifth aspect, the positively charged moiety is tri-methyl-ammonium, N,N-dimethyl-piperidinium or N-alkyl-quinuclidinium.

In embodiments of the fifth aspect of the present invention, the charged unit Z is a negatively charged unit. In embodiments of the fifth aspect of the present invention, the negatively charged unit Z is choosen in a manner that the resulting compound of formula A has a pKb of 10 or higher, more particularly has a pKb of 12 or higher. In embodiments of the fifth aspect of the present invention, the negatively charged unit Z is selected from the group consisting of a phosphate, sulphate, sulphonate or carboxylate.

In embodiments of the fifth aspect of the present invention, the linker L1 and L2 are independently of each other linear linker. In embodiments of the fifth aspect, the linear linker L1 and L2 are independently of each other a single bond between two functional units of the compound of formula A, or comprise 1 to 10 C-atoms, in particular 1 to 6 C-atoms, in particular 1, 2, or 3 C-atoms. In embodiments of the fifth aspect, the linear linker L1 and L2 comprises independently of each other 1 or more heteroatoms, in particular N, O or S. In embodiments of the fifth aspect of the present invention, the linker L1 and L2 are independently of each other substituted or unsubstituted, in particular the linker L1 and L2 are unsubstituted. In embodiments of the fifth aspect of the present invention, the linker L1 and/or L2 is not protonatable. In embodiments of the fifth aspect of the present invention, the linear linker L1 and/or L2 comprises a stabilizing unit. In embodiments of the fifth aspect of the present invention, the stabilizing unit prevents the loss of the charged unit Z during the fragmentation event. In embodiments of the fifth aspect of the present invention, the stabilizing unit prevents the loss of the charged unit Z by destabilizing the potentially formed carbo-kation. In embodiments of the fifth aspect of the present invention, the stabilising unit is separated by one C atom from the charged unit Z. In embodiments of the fifth aspect of the present invention, the stabilising unit comprises at least one heteroatom. In embodiments of the fifth aspect of the present invention, the stabilising unit is selected from the group consisting of CO, or isoelectrical analogons thereof such as SO or SO2. In embodiments of the fifth aspect, the linear linker L1 is a single bond connecting the reactive unit and the neutral loss unit, and the linker L2 is 1 or 2 C-atoms, optionally comprising one or two heteroatoms, in particular 1 or 2 O-atoms, connecting the neutral loss unit and the positively charged unit of the compound of formula A. In embodiments of the fifth aspect, the linear linker L1 comprises 1 C-atom connecting the reactive unit and the neutral loss unit, and the linker L2 comprises 1 or 2 C-atoms and 1 O-atom connecting the neutral loss unit and the positively charged unit of the compound of formula A. In embodiments of the fifth aspect, the linear linker L1 comprises 3 C-atoms and one O-atom connecting the reactive unit and the neutral loss unit, and the linker L2 comprises 1 C-atom and 1 O-atom connecting the neutral loss unit and the positively charged unit of the compound of formula A. In embodiments of the fifth aspect, the linear linker L1 comprises 6 C-atoms and one O-atom connecting the reactive unit and the neutral loss unit, and the linker L2 comprises 2 C-atoms and 1 O-atom connecting the neutral loss unit and the positively charged unit of the compound of formula A. In embodiments of the fifth aspect, the linear linker L1 comprises 7 C-atoms and 1 O-atom connecting the reactive unit and the neutral loss unit, and the linker L2 is a single bond connecting the neutral loss unit and the positively charged unit of the compound of formula A.

In embodiments of the fifth aspect of the present invention, the compound has a structure of formula A, wherein the reactive unit X is a carbonyl-reactive unit, neutral loss unit Y is a 5-membered heterocyclic unit, and the charged unit Z is a permanently positively charged unit.

In embodiments of the fifth aspect of the present invention, the compound has a structure of formula A, wherein the reactive unit X is a diene reactive unit, the neutral loss unit Y is a 5-membered heterocyclic unit, and the charged unit Z is a permanently positively charged unit.

In embodiments of the fifth aspect of the present invention, the compound has a structure of formula A, wherein the reactive unit X is a hydrazine unit, the neutral loss unit Y is a 5-membered heterocyclic moiety comprising at least 3 heteroatoms, and the charged unit Z is a tertiary ammonium group.

In embodiments of the fifth aspect of the present invention, the compound has a structure of formula A, wherein the reactive unit X is a hydrazide unit, the neutral loss unit Y is a 5-membered heterocyclic unit comprising at least 3 heteroatoms, and the charged unit Z is a tertiary ammonium group.

In embodiments of the fifth aspect of the present invention, the compound has a structure of formula A, wherein the reactive unit X is a hydrazine unit, the neutral loss unit Y is a 5-membered heterocyclic moiety comprising at least 3 heteroatoms, and the charged unit Z is a piperidine unit.

In embodiments of the fifth aspect of the present invention, the compound has a structure of formula A, wherein the reactive unit X is a hydrazide unit, the neutral loss unit Y is a 5-membered heterocyclic unit comprising at least 3 heteroatoms, and the charged unit Z is a piperidine unit.

In embodiments of the fifth aspect of the present invention, the compound has a structure of formula A, wherein the reactive unit X is a hydrazine unit, the neutral loss unit Y is a 5-membered heterocyclic moiety comprising at least 3 heteroatoms, and the charged unit Z is a pyridine unit.

In embodiments of the fifth aspect of the present invention, the compound has a structure of formula A, wherein the reactive unit X is a hydrazide unit, the neutral loss unit Y is a 5-membered heterocyclic unit comprising at least 3 heteroatoms, and the charged unit Z is a pyridine unit.

In embodiments of the fifth aspect of the present invention, the compound has a structure of formula A, wherein the reactive unit X is a Cookson-type reagent, the neutral loss unit Y is a 5-membered heterocyclic unit comprising at least 3 heteroatoms, and the charged unit Z is a tertiary ammonium group.

In embodiments of the fifth aspect of the present invention, the compound has a structure of formula A, wherein the reactive unit X is a Cookson-type reagent, the neutral loss unit Y is a 5-membered heterocyclic unit comprising at least 3 heteroatoms, and the charged unit Z is a piperidine unit.

In embodiments of the fifth aspect of the present invention, the compound has a structure of formula A, wherein the reactive unit X is a Cookson-type reagent, the neutral loss unit Y is a 5-membered heterocyclic unit comprising at least 3 heteroatoms, and the charged unit Z is a pyridine unit.

In embodiments of the fifth aspect of the present invention, the compound has a structure of formula A, wherein the reactive unit X is $H_2N$—NH—, the neutral loss unit Y is 1,2,3-triazole, 1,2,4-triazol, 1,2,3,4-tetrazole, or 1,2,4,5-tetrazine, and the charged unit Z is a tertiary ammonium unit.

In embodiments of the fifth aspect of the present invention, the compound has a structure of formula A, wherein the reactive unit X is $H_2N$—NH—, the neutral loss unit Y is 1,2,3-triazole, 1,2,4-triazol, 1,2,3,4-tetrazole, or 1,2,4,5-tetrazine, and the charged unit Z is a piperidine unit.

In embodiments of the fifth aspect of the present invention, the compound has a structure of formula A, wherein the reactive unit X is $H_2N$—NH—, the neutral loss unit Y is 1,2,3-triazole, 1,2,4-triazol, 1,2,3,4-tetrazole, or 1,2,4,5-tetrazine, and the charged unit Z is a pyridine unit.

In embodiments of the fifth aspect of the present invention, the compound has a structure of formula A, wherein the reactive unit X is $H_2N$—O—C—, the neutral loss unit Y is 1,2,3-triazole, 1,2,4-triazol, 1,2,3,4-tetrazole, or 1,2,4,5-tetrazine, and the charged unit Z is a dimethyl-piperidine or quinuclidine unit.

In embodiments of the fifth aspect of the present invention, the compound has a structure of formula A, wherein the reactive unit X is 1,2,4-triazolin-3,5-dione, the neutral loss unit Y is 1,2,3-triazole, 1,2,4-triazol, 1,2,3,4-tetrazole, or 1,2,4,5-tetrazine, and the charged unit Z is a dimethyl-piperidine or quinuclidine moiety.

In embodiments of the fifth aspect of the present invention, the compound of formula A is selected from the group consisting of (i) Label 1

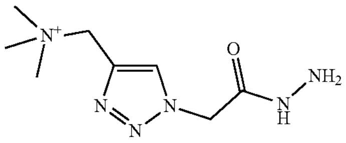

(ii) Label 2

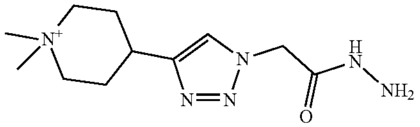

and (iii) Label 3

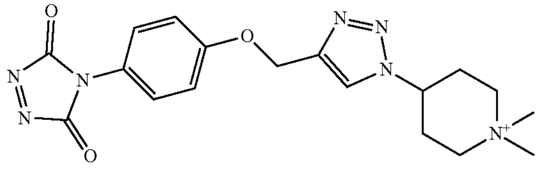

Further examples of the compound of formula A are the following (iv) Label 4

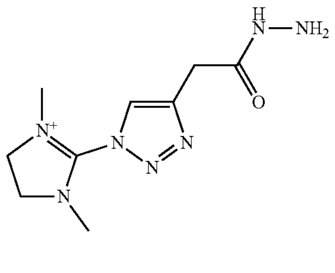

-continued (v) Label 5

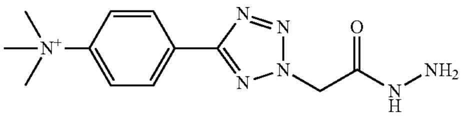

(vi) Label 6

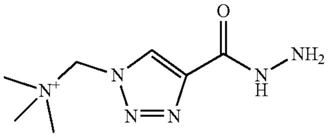

(vii) Label 7

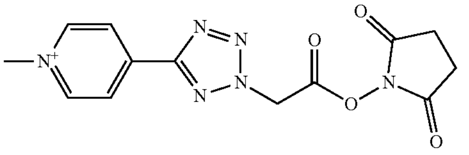

(viii) Label 8

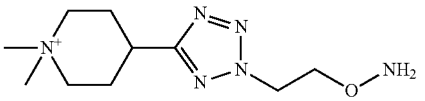

(ix) Label 9

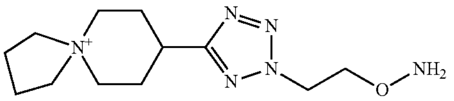

(x) Label 10

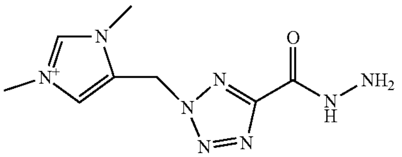

(xi) Label 11

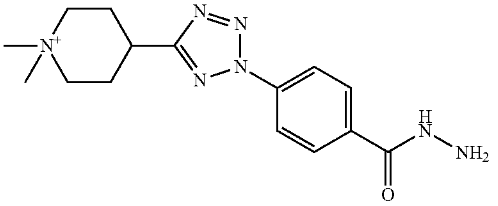

(xii) Label 12

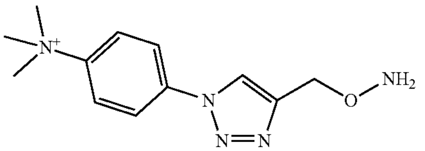

In a sixth aspect, the present invention relates to a method for the mass spectrometric determination of an analyte molecule comprising the steps:

(a) reacting the analyte molecule with a compound of formula A as disclosed herein above with regard to the first aspect of the present invention, whereby a covalent adduct of the analyte molecule and the compound of formula A is formed, and (b) subjecting the adduct of step (a) to a mass spectrometric analysis, Step (a) may occur at different stages within the sample preparation workflow prior to mass spectrometric determination. The samples comprising an analyte molecule may be pre-treated and/or enriched by various methods. The pre-treatment method is dependent upon the type of sample, such as blood (fresh or dried), plasma, serum, urine, or saliva, whereas the enrichment method is dependent on the analyte of interest. It is well known to the skilled person which pre-treatment sample is suitable for which sample type. It is also well-known to the skilled person which enrichment method is suitable for which analyte of interest.

In embodiments of the sixth aspect of the present invention, step (a) of the present method for the mass spectrometric determination of an analyte molecule takes place i) subsequent to a pre-treatment step of the sample, ii) subsequent to a first enrichment of the sample, or iii) subsequent to a second enrichment of the sample.

In embodiments of the sixth aspect of the present invention, wherein the sample is a whole blood sample, it is assigned to one of two pre-defined sample pre-treatment (PT) workflows, both comprising the addition of an internal standard (ISTD) and a hemolysis reagent (HR) followed by a pre-defined incubation period (Inc), where the difference between the two workflows is the order in which the internal standard (ISTD) and a hemolysis reagent (HR) are added. In embodiments water is added as a hemolysis reagents, in particular in an amount of 0.5:1 to 20:1 mL water/mL sample, in particular in an amount of 1:1 to 10:1 mL water/mL sample, in particular in an amount of 2:1 to 5:1 mL water/mL sample.

In embodiments of the sixth aspect of the present invention, wherein the sample is a urine sample, it is assigned to one of other two pre-defined sample PT workflows, both comprising the addition of an internal standard and an enzymatic reagent followed by a pre-defined incubation period, where the difference between the two workflows is the order in which the internal standard and a enzymatic reagent are added. An enzymatic reagent is typically a reagent used for glucuronide cleavage or protein cleavage or any pre-processing of analyte or matrix. In an additional step a derivatization reagent such as compounds of the present invention as disclosed herein above or below, is added followed by an incubation period.

In embodiments of the sixth aspect of the present invention, the enzymatic reagent in selected from the group consisting of glucuronidase, (partial) exo- or endo-deglycoslation enzymes, or exo- or endo preoteases. In embodiments, glucoronidase is added in amount of 0.5-10 mg/ml, in particular in an amount of 1 to 8 mg/ml, in particular in an amount of 2 to 5 mg/ml.

In embodiments of the sixth aspect of the present invention, wherein the sample is plasma or serum it is assigned to another pre-defined PT workflow including only the addition of an internal standard (ISTD) followed by a pre-defined incubation time.

It is well-known to the skilled person which incubation time and temperature to choose for a sample treatment, chemical reaction or method step considered and as named herein above or below. In particular, the skilled person knows that incubation time and temperature depend upon each other, in that e.g. a high temperature typically leads to a shorter incubation period and vise versa. In embodiments of the sixth aspect of the invention, the incubation temperature is in a range of 4 to 45° C., in particular in a range of 10-40° C., in particular at 20-37° C. In embodiments, the incubation time is in the range of 30 sec to 120 min, in particular 30 sec to 1 min, 30 sec to 5 min, 30 sec to 10 min, 1 min to 10 min, or 1 min to 20 min, 10 min to 30 min, 30 min to 60 min, or 60 min to 120 min. In particular embodiments, the incubation time is a multiple of 36 sec.

Accordingly, the embodiments of the present method, step a) takes place subsequent to either of the above disclosed pre-treatment process of the sample.

In embodiment of the sixth aspect of the present invention, wherein the reaction of the compound of formula (A) and the analyte molecule in step a) takes place before any enrichment process, the compound of formula (A) is added to the pre-treated sample of interest. Accordingly, the adduct of the analyte molecule and the compound of formula (I) is is formed after the pre-treatment and prior to the first enrichment process. The adduct is thus, subjected to the first enrichment process and to the second enrichment process before being subjected to the mass spectrometric analysis of step b).

The pre-treated sample may be further subjected to an analyte enrichment workflow. The analyte enrichment workflow may include one or more enrichment methods. Enrichment methods are well-known in the art and include but are not limited to chemical enrichment methods including but not limited to chemical precipitation, and enrichment methods using solid phases including but not limited to solid phase extraction methods, bead workflows, and chromatographic methods (e.g. gas or liquid chromatographie).

In embodiments of the sixth aspect of the present invention, a first enrichment workflow comprises the addition of of a solid phase, in particular of solid beads, carrying analyte-selective groups to the pre-treated sample. In embodiments of the sixth aspect of the present invention, a first enrichment workflow comprises the addition of magnetic or paramagnetic beads carrying analyte-selective groups to the pre-treated sample. In embodiments of the sixth aspect of the present invention, the addition of the magnetic beads comprises agitation or mixing. A pre-defined incubation period for capturing the analyte(s) of interest on the bead follows. In embodiments of the sixth aspect of the present invention, the workflow comprises a washing step (W1) after incubation with the magnetic beads. Depending on the analyte(s) one or more additional washing steps (W2) are performed. One washing step (W1, W2) comprises a series of steps including magnetic bead separation by a magnetic bead handling unit comprising magnets or electromagnets, aspiration of liquid, addition of a washing buffer, resuspension of the magnetic beads, another magnetic bead separation step and another aspiration of the liquid. Moreover washing steps may differ in terms of type of solvent (water/organic/salt/pH), apart from volume and number or combination of washing cycles. It is well-known to the skilled person how to choose the respective parameters. The last washing step (W1, W2) is followed by the addition of an elution reagent followed by resuspension of the magnetic beads and a pre-defined incubation period for releasing the analyte(s) of interest from the magnetic beads. The bound-free magnetic beads are then separated and the supernatant containing derivatized analyte(s) of interest is captured.

In embodiments of the sixth aspect of the present invention, a first enrichment workflow comprises the addition of magnetic beads carrying matrix-selective groups to the pre-treated sample. In embodiments of the sixth aspect of the present invention, the addition of the magnetic beads comprises agitation or mixing. A pre-defined incubation period for capturing the matrix on the bead follows. Here, the analyte of interest does not bind to the magnetic beads but remains in the supernatant. Thereafter, the magnetic beads are separated and the supernatant containing the enriched analyte(s) of interest is collected.

In embodiments of the sixth aspect of the present invention, the supernatant is subjected to a second enrichment workflow. Here, the supernatant is transferred to the LC station or is transferred to the LC station after a dilution step by addition of a dilution liquid. Different elution procedures/reagents may also be used, by changing e.g. the type of solvents (water/organic/salt/pH) and volume. The various parameters are well-known to the skilled person and easily chosen.

In embodiments of tie sixth aspect of the present invention, wherein step a) of the present method did not take place directly after the pre-treatment method, step a) may take place after the first enrichment workflow using magnetic beads as described herein above.

In embodiments of the sixth aspect of the present invention, wherein analyte specific magnetic beads are used, the compounds of formula (A) as disclosed herein above or below, is added to the sample of interest after the washing steps (W1, W2) are concluded either prior to, together with or subsequent with the elution reagent, which is followed by an incubation period (defined time and temperature).

In embodiments of the sixth aspect of the present invention, the bound-free magnetic beads are then separated and the supernatant containing the adduct of step a) is collected. In embodiments of the sixth aspect of the present invention, the supernatant containing the adduct of step a) is transferred to a second enrichment workflow, in particular either directly transferred to an LC station or after a dilution step by addition of a dilution liquid.

In embodiments of the sixth aspect of the present invention, wherein matrix-specific magnetic beads are used, the compounds of formula (A) as disclosed herein above or below, is added to the sample of interest before, simultaneously with or after the magnetic beads are separated. In embodiments of the sixth aspect of the present invention, the supernatant containing the adduct of step a) is transferred to a second enrichment workflow, in particular either directly to an LC station or after a dilution step by addition of a dilution liquid.

Accordingly, in embodiments of the sixth aspect of the present invention, wherein the reaction of the compound of formula (A) and the analyte molecule in step a) takes place subsequent to a first enrichment process, the compound of formula (A) is added to the sample of interest after the first enrichment process, in particular a first enrichment process using magnetic beads, is concluded. Accordingly, the sample is first pre-treated as described herein above, is then subjected to a first enrichment process, in particular using magnetic beads, carrying analyte selective groups as described herein above, and prior to, simultaneously with or subsequently to the elution from the beads, the compound of formula (A) is added. Accordingly, the adduct of the analyte molecule and the compound of formula (A) is formed after the first enrichment process and prior to the second enrichment process. The adduct is thus, subjected to the second enrichment process before being subjected to the mass spectrometric analysis of step b).

In another embodiment of the sixth aspect of the present invention, step (a) of the present method takes place after a second analyte enrichment workflow. In the second enrichment workflow, chromatographic seperation is used to further enrich the analyte of interest in the sample. In embodiments of the sixth aspect of the present invention, the chromatographic seperation is gas or liquid chromatography. Both methods are well known to the skilled person. In embodiments of the sixth aspect of the present invention, the liquid chromatographie is selected from the group consisting of HPLC, rapid LC, micro-LC, flow injection, and trap and elute.

In embodiments of the sixth aspect of the present invention, step a) of the present method takes place concurrent with or subsequent to the chromatographic seperation. In embodiment of the sixth aspect of the present invention, the compound of formula (A) is added to the column together with the elution buffer. In alternative embodiments, the compound of formula (A) is added post column.

In embodiments of the sixth aspect of the present invention, the first enrichment process includes the use of analyte selective magnetic beads. In embodiments of the sixth aspect of the present invention, the second enrichment process includes the use of chromatographic separation, in particular using liquid chromatography.

In embodiments, the mass spectrometric analysis step (b) comprises:

(i) subjecting an ion of the adduct to a first stage of mass spectrometric analysis, whereby the parent ion of the adduct is characterised according to its mass/charge (m/z) ratio, (ii) causing fragmentation of the adduct parent ion, whereby a first neutral entity, is released and a daughter ion of the adduct is generated, wherein the daughter ion of the adduct differs in its m/z ratio from the adduct parent ion, and (iii) subjecting the daughter ion of the adduct to a second stage of mass spectrometric analysis, whereby the daughter ion of the adduct is characterized according to its m/z ratio, and/or wherein (ii) may further comprise alternative fragmentation of the adduct ion, whereby a second neutral entity different from the first neutral entity is released and a second daughter ion of the adduct is generated, and wherein (iii) may further comprise subjecting the first and second daughter ions of the adduct to a second stage of mass spectrometric analysis, whereby the first and second daughter ions of the adduct are characterised according to their m/z ratios.

Accordingly, in embodiments of the sixth aspect of the present invention, wherein the reaction of the compound of formula (A) and the analyte molecule in step a) takes place subsequent to a second enrichment process, the compound of formula (A) is added to the sample of interest after the second enrichment process using chromatography, in particular liquid chromatography, is concluded. Accordingly, in this case, the sample is first pre-treated as described herein above, is then subjected to a first enrichment process, in particular using magnetic bead, as described herein above, followed by chromatographic separation, in particular using liquid chromatography, and subsequent to chromatographic separation the compound of formula (A) is added. Accordingly, the adduct of the analyte molecule and the compound of formula (A) is formed after the second enrichment process. The adduct is thus, not subjected to a enrichment process before being subjected to the mass spectrometric analysis of step b).

In further embodiments, the present invention relates to the following aspects:

1. Compound of formula A:

X-L1-Y-L2-Z wherein

X is a reactive unit, which is in particular capable of forming a covalent bond with an analyte molecule, L1 and L3 are independently of each other substituted or unsubstituted linker, in particular linear linker Y is a neutral loss unit, Z is a charged unit comprising at least one permanently charged moiety, in particular comprising one permanently charged moiety, including any salt thereof.

2. Compound of aspect 1, wherein the reactive unit X is selected from the group consisting of carbonyl reactive unit, diene reactive unit, hydroxyl reactive unit, amino reactive unit, an imine reactive unit, a thiol reactive unit, a diol reactive unit, a phenol reactive unit, epoxide reactive unit, a disulfide reactive unit, and a azide reactive unit.

3. Compound of any of the preceding aspects, wherein the reactive unit X is a carbonyl-reactive group, in particular wherein X is selected from the group consisting of
   (i) a hydrazine unit, in particular a H2N—NH—, or H2N-NR1- unit, wherein R1 is aryl or C1-4 alkyl, particularly C1 or C2 alkyl, optionally substituted,
   (ii) a hydrazide unit, in particular a carbo-hydrazide or a sulfohydrazide, in particular a H2N—NH—C(O)—, or H2N-NR2-C(O)— unit, wherein R2 is aryl or C1-4 alkyl, particularly C1 or C2 alkyl, optionally substituted,
   (iii) a hydroxylamino unit, in particular a H2N—O— unit, and
   (iv) a dithiol unit, particularly a 1,2-dithiol or 1,3-dithiol unit.
4. Compound of aspect 1 or 2, wherein the reactive unit X is a thiol-reactive group or is an amino-reactive group such as an active ester group, e.g. N-hydroxysuccinimide (NHS) ester or sulpho-NHS ester, a hydroxybenzotrialzole (HOBt) ester or 1-hydroxy-7-acabenzotriazole (HOAt) ester group.
5. Compound of any of the preceding aspects, wherein the neutral loss unit Y releases a neutral entity upon ionization.
6. Compound of any of the preceding aspects, wherein the charged unit Z is permanently charged.
7. Compound of any of the preceding aspects, wherein the linker L1 L2 independently of each other comprise 1 to 10 C-atoms, optionally comprising 1 or more heteroatoms.
8. Compound of any of the preceding aspects, wherein the reactive unit X is a carbonyl-reactive group, the neutral loss unit Y is a 5-membered heterocyclic moiety, the charge unit Z comprises one permanently positively charged moiety
9. Compound of any of the preceding aspects, wherein the reactive unit X is $H_2N$—NH—, the neutral loss unit Y is triazole or tetrazole, and the charge unit Z comprises a piperidine unit.
10. A composition comprising the compound of any of aspects 1-9.
11. A kit comprising the compound of any of aspects 1-9 or the composition of aspect 10.
12. A covalent adduct comprising an analyte molecule and the compound of any of aspects 1-9 covalently linked to each other, in particular wherein the covalent adduct is formed by chemical reaction of the analyte molecule and the compound of any of aspects 1-9.
13. Use of a compound of formula A:

X-L1-Y-L2-Z wherein

X is a reactive unit, which is in particular capable of forming a covalent bond with an analyte molecule L1 and L2 are independently of each other substituted or unsubstituted linker, in particular linear linker, Y is a neutral loss unit, Z is a charged unit comprising at least one permanently charged moiety, in particular comprising one permanently charged moiety, including any salt thereof, or of a composition or kit comprising at least one compound of formula A for the mass spectrometric determination of an analyte molecule, wherein the mass spectrometric determination particularly comprises a tandem mass spectrometric determination, more particularly in a triple quadrupole device.

14. A method for the mass spectrometric determination of an analyte molecule comprising the steps:
   (a) reacting the analyte molecule with a compound of formula A as defined in any one of claims 1-9, whereby a covalent adduct of the analyte molecule and the compound of formula A is formed, and
   (b) subjecting the adduct from step (a) to a mass spectrometric analysis, preferably wherein the mass spectrometric analysis step (b) comprises:
      (i) subjecting an ion of the adduct to a first stage of mass spectrometric analysis, whereby the ion of the adduct is characterised according to its mass/charge (m/z) ratio,
      (ii) causing fragmentation of the adduct ion, whereby a first neutral entity, particularly a low-molecular weight neutral entity is released and a daughter ion of the adduct is generated, wherein the daughter ion of the adduct differs in its m/z ratio from the adduct ion, and
      (iii) subjecting the daughter ion of the adduct to a second stage of mass spectrometric analysis, whereby the daughter ion of the adduct is characterized according to its m/z ratio, and/or wherein (ii) may further comprise alternative fragmentation of the adduct ion, whereby a second neutral entity different from the first neutral entity is released and a second daughter ion of the adduct is generated, and wherein (iii) may further comprise subjecting the first and second daughter ions of the adduct to a second stage of mass spectrometric analysis, whereby the first and second daughter ions of the adduct are characterised according to their m/z ratios.

EXAMPLES

The following examples are provided to illustrate, but not to limit the presently claimed invention.

Example 1: Synthesis of Label 1

1. Step: Synthesis of [1-(2-methoxy-2-oxo-ethyl) triazol-4-yl]methyl-trimethyl-ammonium; 2,2,2-trifluoroacetate

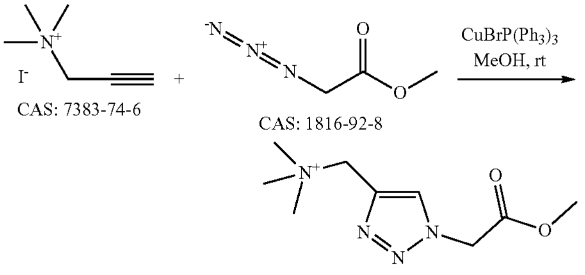

To a solution of N,N,N-trimethyl-propargyl-ammonium iodide (270 mg, 1.20 mmol) in 10 ml methanol was added methyl azidoacetate (117 μL, 138 mg, 1.20 mmol) under argon atmosphere. $CuBr(PPh_3)_3$ (112 mg, 0.12 mmol) was added and the suspension was stirred over night at room temperature. The reaction mixture was concentrated in vacuo and the crude product was purified by by HPLC prep to give 143 mg, 37% yield, of desired product as yellow solid, TFA salt.

HPLC method C-18 column:

0 min: 98% $H_2O$ 0.1% TFA, 2% $CH_3CN$ 0.1% TFA;

0-10 min: 98% $H_2O$ 0.1% TFA, 2% $CH_3CN$ 0.1% TFA;

10-60 min: 70% $H_2O$ 0.1% TFA; 30% $CH_3CN$ 0.1% TFA;

60-90 min: 20% $H_2O$ 0.1% TFA; 80% $CH_3CN$ 0.1% TFA;

$^1H$ NMR (400 MHz, METHANOL-$d_4$): δ ppm 3.18 (s, 9H) 3.82 (s, 3H) 4.74 (s, 2H) 5.45 (s, 2H) 8.43 (s, 1H).

$^{13}C$ NMR (101 MHz, METHANOL-$d_4$): δ ppm 51.96 (1 C) 53.55-53.66 (1 C), 61.28 (1 C), 131.03 (1 C), 137.16 (1 C), 169.06 (1 C).

HPLC-MS (m/z) [M]+ calcd 213.1351 found 213.4

2. Step: Synthesis of [1-(2-hydrazino-2-oxo-ethyl) triazol-4-yl]methyl-trimethyl-ammonium; 2,2,2-trifluoroacetate

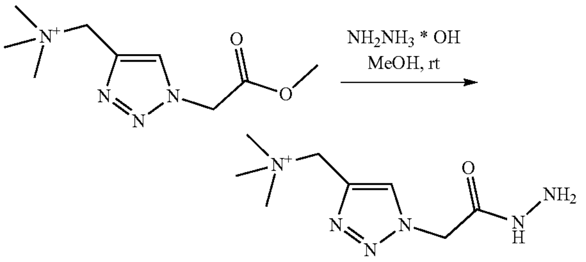

To a solution of the ester (91.3 mg, 280 μmol) in 10 ml methanol was added hydrazine monohydrate (~65%, 209 μL, 216 mg, 2.80 mmol) and the reaction mixture was stirred at room temperature for 4 h. The mixture was concentrated in vacuo and subjected to HPLC prep to give 59 mg, 48%, of the of desired product as colorless oil, TFA salt.

$^1H$ NMR (400 MHz, ACETONITRILE-$d_3$): δ ppm 3.05 (s, 9H) 4.55 (s, 2H) 5.16 (s, 2H) 8.22 (s, 1H).

$^{13}C$ NMR (101 MHz, ACETONITRILE-$d_3$): δ ppm 51.71 (1 C) 53.60 (1 C) 53.64 (1 C) 53.67 (1 C) 61.19 (1 C) 130.49 (1 C) 136.39 (1 C) 170.50 (1 C).

HPLC-MS (m/z) [M]+ calcd 213.14638 found 213.4

Example 2: Synthesis of Label 2

1.Step: Synthesis of 4-ethynyl-1,1-dimethyl-piperidin-1-ium; 2,2,2-trifluoroacetate

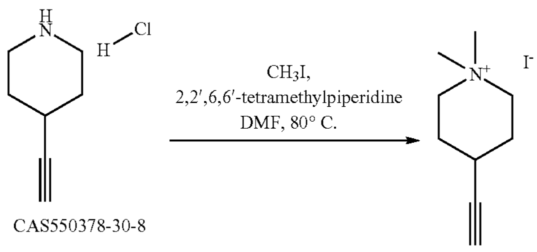

CAS550378-30-8

To a solution of 4-ethyl-piperidine hydrochloride (561 mg, 3.85 mmol) in 25 ml DMF was added 2,2',6,6'-tetramethylpiperidine (1.43 ml, 1.20 g, 8.47 mmol) and methyliodide (1.84 ml, 4.20 g, 19.3 mmol). The reaction mixture was refluxed for 8 h, cooled to room temperature and stirred for additional 16 h. The mixture was concentrated in vacuo and the obtained crude material was washed with acetone (3×). The remaining solid was dissolved at reflux in a minimal amount of methanol (~10 mL) and a 2-fold volume of acetone added. The solution was stored at 4° C. for 16 h. The yellow crystalline solids were collected, washed with acetone and dried in vacuo to yield 242 mg, 24% yield, of desired product as colorless oil.

$^1H$ NMR (400 MHz, DMSO-$d_6$): δ ppm 1.81-1.92 (m, 2H) 1.98-2.07 (m, 2H) 2.65-2.73 (m, 1H) 3.05 (d, J=2.38 Hz, 1H) 3.07 (d, J=1.76 Hz, 6H) 3.27-3.42 (m, 4H).

$^{13}C$ NMR (101 MHz, DMSO-$d_6$): δ ppm 23.64 (1 C) 25.61 (1 C) 53.1 (2 C) 60.18 (1C) 73.14 (1C) 85.28 (1C).

HPLC-MS (m/z) [M]+ calcd 138.1283 found 138.2

2. Step: Synthesis of Methyl 2-[4-(1,1-dimethylpiperidin-1-ium-4-yl)triazol-1-yl]acetate; 2,2,2-trifluoroacetate

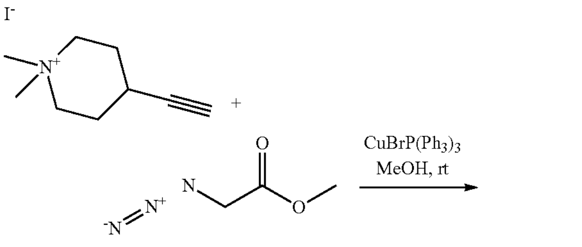

CAS: 1816-92-8

To a solution of the alkyne (265 mg, 1.00 mmol) in 10 ml methanol was added methyl azidoacetate (97.3 μL, 115 mg, 1.00 mmol) under argon atmosphere. $CuBr(PPh_3)_3$ (93 mg, 0.1 mmol) was added and the suspension was stirred over night at room temperature. The reaction mixture was concentrated in vacuo and the crude product was purified by HPLC prep to give 32 mg, 9%, of desired product as colorless oil, TFA salt.

$^1H$ NMR (400 MHz, METHANOL-$d_4$): δ ppm 2.18-2.29 (m, 4H) 3.11-3.19 (m, 1H) 3.20 (s, 3H) 3.23 (s, 3H) 3.48-3.64 (m, 4H) 3.73 (s, 1H) 3.80 (s, 3H) 5.33 (s, 2H) 7.93-7.95 (m, 1H).

$^{13}C$ NMR (101 MHz, METHANOL-$d_4$): δ ppm 27.20 (1 C) 31.38 (1 C) 50.01 (1 C) 51.75 (1 C) 53.48 (2 C) 63.21 (1 C) 124.50 (1 C) 150.50 (1 C) 169.10 (1 C).

HPLC-MS (m/z) [M]+ calcd 253.16645 found 253.4

3. Step: Synthesis of 2-[4-(1,1-dimethylpiperidin-1-ium-4-yl)triazol-1-yl]acetohydrazide; 2,2,2-trifluoroacetate

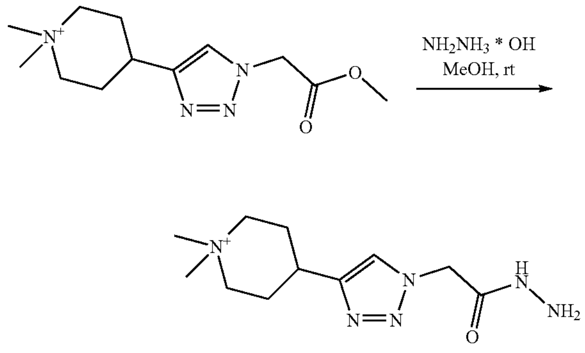

To a solution of the ester (110 mg, 300 μmol) in 10 ml methanol was added hydrazine monohydrate (~65%, 224 μL, 231 mg, 3.0 mmol) and the reaction mixture was stirred at room temperature for 4 h. The mixture was concentrated in vacuo and the crude product was purified by HPLC prep to give 111 mg, 77% yield, of desired product as colorless oil, TFA salt.

$^{1}$H NMR (400 MHz, METHANOL-$d_4$): δ ppm 2.16-2.29 (m, 4H) 3.15 (m, 1H) 3.20 (s, 3H) 3.24 (s, 3H) 3.47-3.65 (m, 4H) 5.22 (s, 2H) 7.97 (s, 1H).

$^{13}$C NMR (101 MHz, METHANOL-$d_4$): δ ppm 27.13 (1 C) 31.30 (1 C) 52.94 (2 C) 56.14 (1 C) 63.11 (1 C) 124.7 (1 C) 150.5 (1 C) 171.1 (1 C).

HPLC-MS (m/z) [M]+ calcd 253.1777 found 253.4

Example 3: Synthesis of Label 3

1.Step: Synthesis of 4-[4-[2-[4-(1,1-dimethylpiperidin-1-ium-4-yl)triazol-1-yl]ethoxy]phenyl]-1,2,4-triazolidine-3,5-dione; 2,2,2-trifluoroacetate

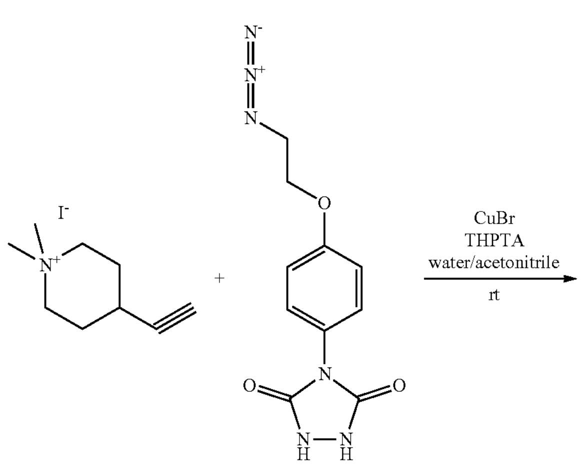

CAS: 1313211-52-7

-continued

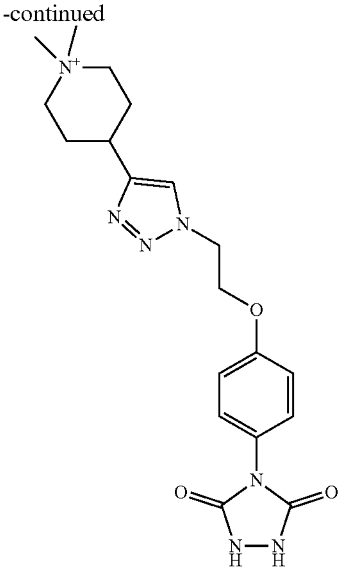

To a solution of 4-ethynyl-1,1-dimethyl-piperidin-1-ium iodide (151 mg, 570 μmol) and 4-(4-(2-azidoethoxy)phenyl)-1,2,4-triazolidine-3,5-dione (99.6 mg, 380 μmol) in 30 ml of 50% aq. acetonitrile was added a preformed Cu-THPTA complex (171 μmol in 1 mL 50% aq. acetonitrile). Of note, the Cu-THPTA complex was obtained by dissolving CuBr (24.4 mg, 171 gmol) and tris(3-hydroxypropyl-triazolylmethyl)amine (74.2 mg, 171 μmol) in 1 ml of 50% aq. acetonitrile under argon atmosphere. After 6 h, additional Cu-THPTA complex (114 gmol in 0.5 mL 50% aq. acetonitrile) was added and the reaction mixture was stirred overnight. The reaction mixture was concentrated in vacuo and the crude product was purified by RP-HPLC. Lyophilization afforded the product (62 mg, 32%, 1×TFA-salt) as colorless oil.

1H NMR (400 MHz, METHANOL-d4): δ [ppm]=2.17 (br s, 4H) 3.05-3.14 (m, 1H) 3.16 (s, 3H) 3.21 (s, 3H) 3.43-3.59 (m, 4H) 4.47 (t, J=4.89 Hz, 2H) 4.81 (t, J=4.83 Hz, 2H) 6.93-7.03 (m, 2H) 7.28-7.36 (m, 2H) 7.92-8.12 (m, 1H).

ESI-MS: m/z=400.4 (C19H26N7O3 [M]+, calc.: 400.2);

2.Step: Synthesis of 25-Hydroxy Vitamin D3-conjugate

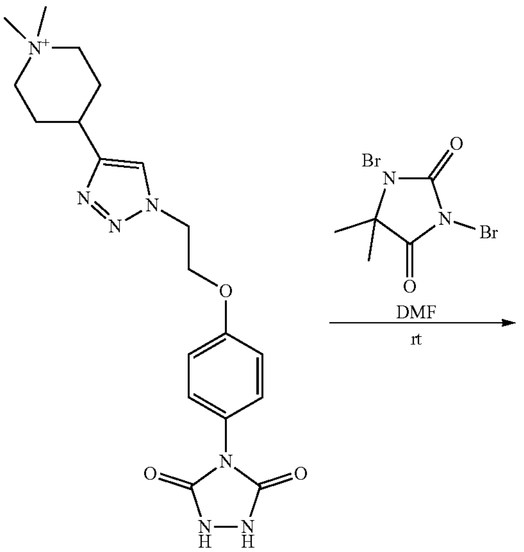

-continued

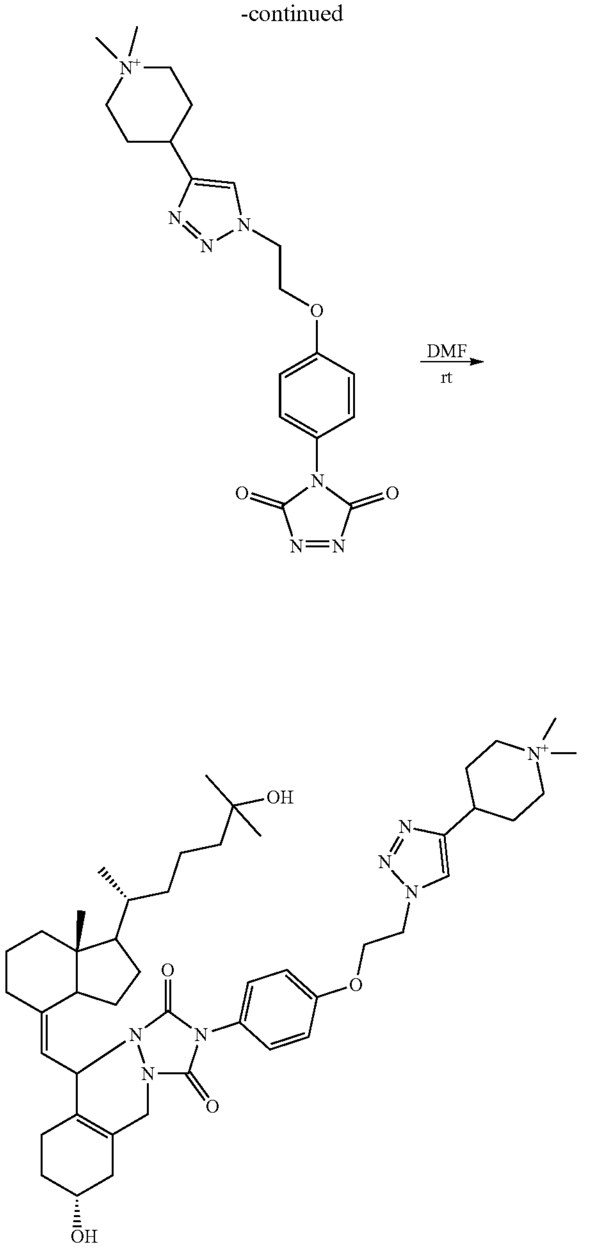

To a solution of 4-[4-[2-[4-(1,1-dimethylpiperidin-1-ium-4-yl)triazol-1-yl]ethoxy]phenyl]-1,2,4-triazolidine-3,5-dione; 2,2,2-trifluoroacetate (15.4 mg, 30 μmol) in 1.5 mL dry DMF was added 1,3-dibromo-5,5-dimethyl-hydantoin (9.43 mg, 33 μmol). The event of the oxidation reaction was indicated by an instant color change from colorless into red. After 60 min, 45 mg of 44% sulfuric acid coated silica was added and the suspension is stirred for 30 min. The solution was filtrated and added to 25-hydroxy vitamin D3 (13.0 mg, 30 gmol) to facilitate the conjugation reaction, which was indicated by an instant color change from red into yellow. The reaction mixture was concentrated in vacuo and the crude product was purified by RP-HPLC. Lyophilization afforded the product 25-hydroxy vitamin D3-conjugate (0.86 mg) as a colorless solid.

ESI-MS: m/z=798.6 (C46H68N7O5 [M]+, calc.: 798.5); MW=913.1 g/mol (C46H68N7O5·C2HF3O2).

Example 4: Preparation of Label 1-Testosterone Derivative and its Analysis Via MS

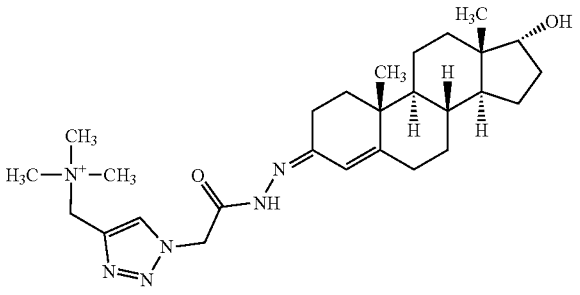

Testosterone was dissolved in MS-grade methanol to a final concentration of 1 mg/mL. Label 1 ([1-(2-hydrazino-2-oxo-ethyl)triazol-4-yl]methyl-trimethyl-ammonium; 2,2,2-trifluoro acetate) was dissolved in MS-grade methanol to a final concentration of 100 mg/mL. 10 μL of Testosterone was derivatized with 10 μL of Label 1 in 70 μL MS-grade methanol and 10 μL glacial acetic acid. The derivatization reaction was incubated in an Eppendorf Thermomixer at 45° C. and 1200 rpm for 2 hours. Yield=96%, calculated by LC-MS analysis based on the area of unlabeled Testosterone.

10 μL of the diluted (1:1000 in 80% methanol) derivatization reaction was analyzed by LC-MS full scan in the positive ion mode at collision energies of 5, 10, 15, 20, 30, 35, 40, 50 and 60 V, respectively.

For LC/MS analysis, samples were analyzed on a Xevo G2-XS-QTof LC-MS system (Waters) connected to a Waters Acquity H UPLC® Class HPLC. The chromatographic separation was performed at 45° C. using a C18-column (Acquity UPLC HSS T3 1.8 μm, 2.1×50 mm column, Waters) with 2 mM $NH_4Ac$, 0.1% formic acid in water (A) or in methanol (B) as mobile phase, with a flow of 450 L/min. A step gradient of 0-2 min 25% B, 2-6 min 25-99.9% B, 6-8 min 99.9% B, and 8-10 min 25% B was used. The optimized ESI source conditions were as follows: desolvation temperature 650° C., source temperature 150° C., cone gas flow 150 L/Hr, desolvation gas flow 800 L/Hr, Collision Gas flow 0.18 mL/min, source offset 80 V and capillary 3.5 V. The TOF-MS mass range was 50-1200 Da, data format centroid, scan time 0.2 sec, analyzer mode sensitivity, dynamic range normal, low mass resolution 15, high mass resolution 10. Data were acquired by MassLynx software (version 4.1, SCN 949) and evaluated with TargetLynx (version 4.1, SCN 909).

In the gas phase, the derivative Label 1-Testosterone undergoes a concerted neutral loss of the trimethylamine and $N_2$ from the triazole group (Δ 87 Da), the positive charge remains on the product ion as depicted in FIG. 1A.

Table 1 shows the calculated and measured m/z values for the precursor ion and product ion of Label 1-Testosterone derivative.

TABLE 1

| Calculated and measured m/z of precursor ion and product ion of Label 1-Testosterone derivative | | |
|---|---|---|
| | calculated | measured |
| Precursor ion [m/z] | 483.34 | 483.27 |
| Product ion [m/z] | 396.26 | 396.20 |
| Neutral loss [Da] | 87.08 | 87.07 |

The Label 1-Testosterone derivative was analyzed at different collision energies by full scan in the positive ion mode. The corresponding peak areas of the precursor ion and the product ion are shown in FIG. 1B. Maximal intensity of the product ion is obtained at a collision energy of 30 V. The corresponding MS spectrum is shown in FIG. 1C with the precursor ion m/z 483.2673 and the product ion m/z 396.1974.

Comparing the maximum peak area of the precursor ion of Label 1-Testosterone derivative at same analyte concentrations (0.1 μg/mL) with unlabeled $^{13}C_3$-Testosterone and Testosterone labeled with reagent A from Rahimoff et al. (2017) an increase in intensity of 7-fold is observed in both cases (FIG. 2). In addition, label 1 generates a 3-fold and 2-fold more intense precursor ion than Amplifex Keto reagent and Girard P reagent, respectively, at same analyte concentrations (0.1 μg/mL, FIG. 2).

Example 5: Preparation of Label 2-Testosterone Derivative and its Analysis Via

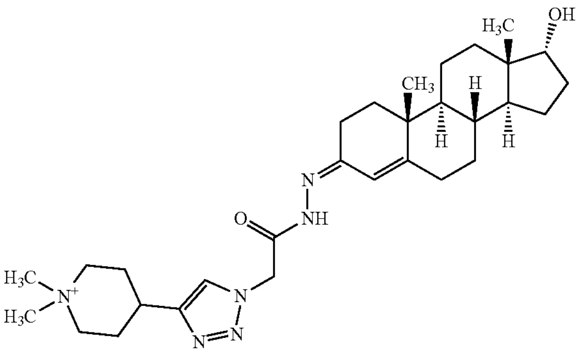

Testosterone was dissolved in MS-grade methanol to a final concentration of 1 mg/mL. Label 2 (2-[4-(1,1-dimethylpiperidin-1-ium-4-yl)triazol-1-yl]acetohydrazide; 2,2,2-trifluoroacetate) was dissolved in MS-grade methanol to a final concentration of 100 mg/mL. 10 μL of Testosterone was derivatized with 10 μL of label 2 in 70 μL MS-grade methanol and 10 μL glacial acetic acid. The derivatization reaction was incubated in an Eppendorf Thermomixer at 45° C. and 1200 rpm for 2 hours. Yield=96%, calculated by LC-MS analysis based on the area of unlabeled Testosterone.

10 μL of the diluted (1:1000 in 80% methanol) derivatization reaction was analyzed by LC-MS full scan in the positive ion mode at collision energies of 5, 10, 15, 20, 30, 35, 40, 50 and 60 V, respectively.

LC/MS analysis was performed as described above for Example 4.

In the gas phase, the derivative Label 2-Testosterone undergoes a neutral loss of $N_2$ from the triazole group (Δ 28 Da), the positive charge remains stable on the product ion in the 1,1-dimethylpiperidinium group as depicted in FIG. 3A.

Table 2 shows the calculated and measured m/z values for the precursor ion and product ion of Label 2-Testosterone derivative.

TABLE 2

| Calculated and measured m/z of precursor ion and product ion of Label 2-Testosterone derivative. | | |
|---|---|---|
| | calculated | measured |
| Precursor ion [m/z] | 523.38 | 523.29 |
| Product ion [m/z] | 495.37 | 495.28 |
| Neutral loss [Da] | 28.01 | 28.01 |

Comparing the maximum peak area of the precursor ion of Label 2-Testosterone derivative at same analyte concentrations (0.1 μg/mL) with unlabeled $^{13}C_3$-Testosterone and Testosterone labeled with reagent A from Rahimoff et al. 2017, an increase in intensity of 9-fold is observed (FIG. 3B). In addition, Label 1 generates a 4-fold and 3-fold more intense precursor ion than Amplifex Keto reagent and Girard P reagent, respectively, at same analyte concentrations (0.1 μg/mL).

Example 6: Analysis of Label 3-25-OH Vitamin D3 Derivative Via MS

The 25-OH-Vitamin D3 derivative was dissolved in MS-grade methanol to a final concentration of 0.1 μg/mL and analyzed by LC-MS full scan in the positive ion mode at collision energies of 5, 10, 15, 20, 30, 35, 40, 50 and 60 V, respectively.

On the LC column, 25-OH-Vitamin D3 derivatized with Label 3 gives a clean, single peak with 180-fold more intensity than underivatized 25-OH-Vitamin D3 (FIG. 4).

In the gas phase, the labeled 25-OH-Vitamin D3 undergoes a neutral loss of $N_2$ from the triazole group (Δ 28 Da), the positive charge remains stable on the product ion in the 1,1-dimethylpiperidinium group as depicted in FIG. 5A.

Table 3 shows the calculated and measured m/z values for the precursor ion and product ion of labeled 25-OH-Vitamin D3.

TABLE 3

| Calculated and measured m/z of precursor ion and product ion of labeled 25-OH-Vitamin D3. | | |
|---|---|---|
| | calculated | measured |
| Precursor ion [m/z] | 798.53 | 798.54 |
| Product ion [m/z] | 770.52 | 770.53 |
| Neutral loss [Da] | 28.01 | 28.01 |

Comparing the maximum peak area of the precursor ion of labeled 25-OH-Vitamin D3 at same analyte concentrations (0.1 μg/mL) with unlabeled 25-OH-Vitamin D3, an increase in intensity of 37-fold is observed (FIG. 5B).

The invention claimed is:

1. A method for the mass spectrometric determination of an analyte molecule comprising the steps:

(a) reacting the analyte molecule with a compound of formula A

X-L1-Y-L2-Z wherein

X is a reactive unit, which is capable of forming a covalent bond with an analyte molecule, L1 and L2 are independently of each other substituted or unsubstituted linker, Y is a neutral loss unit, Z is a charged unit comprising at least one permanently charged moiety, wherein the reactive unit X is $H_2N$—NH—, the neutral loss unit Y is triazole or tetrazole, and the charge unit Z comprises a piperidine unit, or wherein the compound is selected from the group consisting of:

Label 1

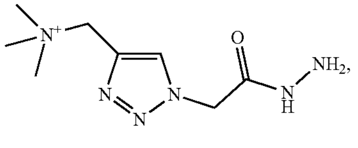

Label 2

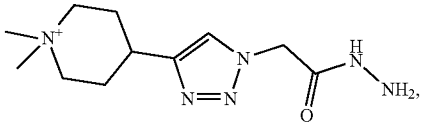

Label 3

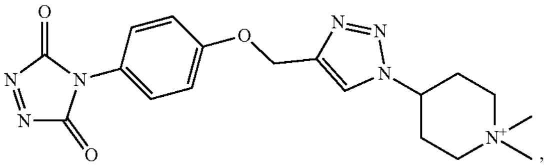

Label 4

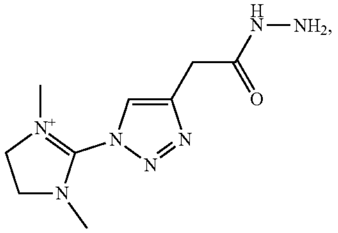

Label 5

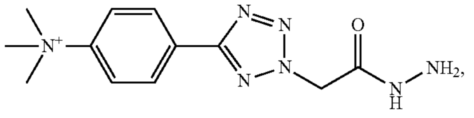

Label 6

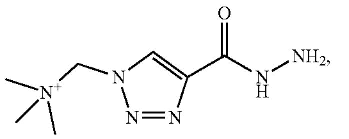

-continued

Label 7

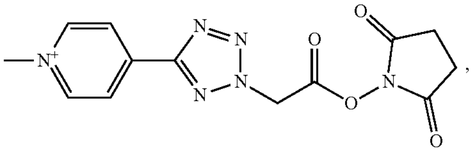

Label 8

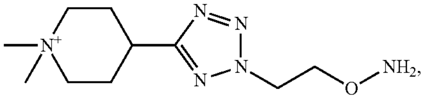

Label 9

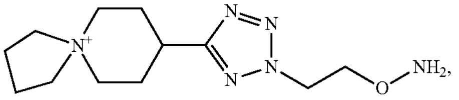

Label 10

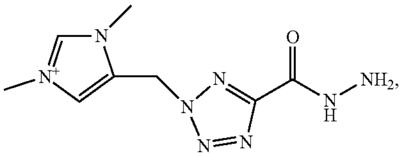

Label 11

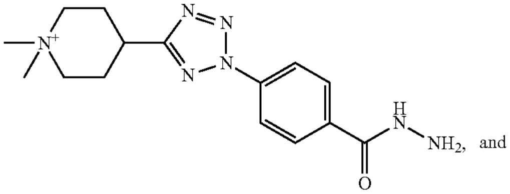

and

Label 12

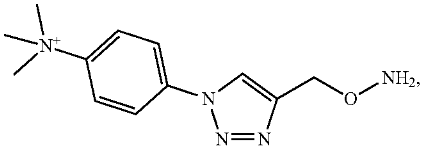

whereby a covalent adduct of the analyte molecule and the compound of formula A is formed by the chemical reaction of the reactive unit with the analyte molecule, and (b) subjecting the adduct from step (a) to a mass spectrometric analysis.

2. The method according to claim 1, wherein the mass spectrometric analysis step (b) comprises:

(i) subjecting an ion of the adduct to a first stage of mass spectrometric analysis, whereby the ion of the adduct is characterised according to its mass/charge (m/z) ratio, (ii) causing fragmentation of the adduct ion, whereby a first neutral entity, particularly a low-molecular weight neutral entity is released and a daughter ion of the adduct is generated, wherein the daughter ion of the adduct differs in its m/z ratio from the adduct ion, and (iii) subjecting the daughter ion of the adduct to a second stage of mass spectrometric analysis, whereby the daughter ion of the adduct is characterized according to its m/z ratio.

3. The method according to claim 2, wherein (ii) further comprises alternative fragmentation of the adduct ion, whereby a second neutral entity different from the first neutral entity is released and a second daughter ion of the adduct is generated, and wherein (iii) further comprises subjecting the first and second daughter ions of the adduct to a second stage of mass spectrometric analysis, whereby the first and second daughter ions of the adduct are characterized according to their m/z ratios.

4. The method according to claim 1, wherein the analyte molecule is present in a sample and the sample is blood, serum, plasma, synovial fluid, spinal fluid, urine, saliva, lymphatic fluid, dried blood spots, tissue extracts cell cultures or tissue cultures.

5. The method according to claim 4, wherein the sample is pre-treated and/or enriched.

6. The method according to claim 1, wherein the mass spectrometric analysis comprises a tandem mass spectrometric determination.

7. The method according to claim 1, wherein the mass spectrometric analysis comprises a tandem mass spectrometric determination in a triple quadrupole device.

8. The method according to claim 1, wherein the neutral loss unit Y releases a neutral entity upon ionization.

9. The method according to claim 1, wherein the linker L1 and L2 independently of each other comprise 1 to 10 C-atoms, optionally comprising 1 or more heteroatoms.

* * * * *